United States Patent [19]
Venkataraman et al.

[11] Patent Number: 6,157,899
[45] Date of Patent: Dec. 5, 2000

[54] PREDICTION OF RESPONSES TO DIFFERENT POWDERING TESTS ON A GALVANNEAL-COATED STEEL SUBSTRATE OR DIFFERENT TESTS ON OTHER SUBSTRATES, USING COMPUTER-BASED SYSTEMS AND METHODS

[75] Inventors: Rangarajan Venkataraman; Dennis D. Newhart, both of Bethlehem, Pa.

[73] Assignee: Bethlehem Steel Corporation

[21] Appl. No.: 09/175,956

[22] Filed: Oct. 21, 1998

[51] Int. Cl.⁷ ..................................................... G06F 17/00
[52] U.S. Cl. ........................... 702/182; 702/81; 702/181; 148/508
[58] Field of Search ................................... 702/182, 179, 702/181, 81, 84; 704/231, 232, 256; 148/508, 514

[56] References Cited

U.S. PATENT DOCUMENTS

| | | | |
|---|---|---|---|
| 5,381,513 | 1/1995 | Isuboka | 704/232 |
| 5,628,044 | 5/1997 | Cook et al. | 419/3 |
| 5,785,772 | 9/1998 | Deka | 148/508 |
| 5,903,459 | 5/1999 | Greenwood et al. | 702/182 |
| 5,987,398 | 11/1999 | Halverson et al. | 702/81 |
| 6,004,507 | 12/1999 | Moranolo | 420/586 |
| 6,041,287 | 3/2000 | Dister et al. | 702/182 |

OTHER PUBLICATIONS

Welcome to Cart, Version 1.1, Jul. 28, 1985, California Statistical Software, Inc., Lafayette, CA.
Salford Systems Introduces Cart Robust (No date) Decision–Tree Software for Data Mining (4 pages).
Fleet Uses Cart Data–Mining Technology to Understand Customer Characteristics and Habits (No date) (2 pages).
Cabela's Stablizes Catalog Mail–Model (No date) Segments with Cart Data–Mining Software (2 pages).

*Primary Examiner*—Marc S. Hoff
*Assistant Examiner*—Bryan Bui

[57] ABSTRACT

Computer-based systems and methods of determining product parameters, performing process control, and/or classifying products are provided. These computer-based systems and methods analyze previous responses to different iterations of one or more tests and, based on this analysis, predict responses to future tests. The predictions are based on a classification and regression tree analysis. Also provided are computer-based systems which are pre-programmed with the results of at least one such analysis and which perform product parameter determination, process control, and/or product classifications based upon those results. The methods and computer systems are particularly well-suited for use in the context of manufacturing galvanneal-coated steel products (e.g., strips, sheets, plates, rods, wires, and the like), though it is understood that the methods and computer systems are not limited to use on such semi-finished products or their methods of manufacture. To the contrary, these methods and computer systems can be successfully applied to processes of manufacturing any product irrespective of its form. Coated and uncoated products can be manufactured according to the subject methods and systems. The methods and systems also can be applied to the manufacturing of substrates other than steel (e.g., aluminum), regardless of whether those substrates are coated, uncoated, or semi-finished.

47 Claims, 32 Drawing Sheets

PREDICTION OF RESPONSES TO DIFFERENT POWDERING TESTS ON A GALVANNEAL-COATED STEEL SUBSTRATE OR DIFFERENT TESTS ON OTHER SUBSTRATES, USING COMPUTER-BASED SYSTEMS AND METHODS

BACKGROUND OF THE INVENTION

The present invention relates to computer-based systems and methods of determining product parameters, performing process control, and/or classifying products based on analysis and prediction of responses to different tests, such as powdering tests on a coated substrate.

Presently, there is a substantial demand for coated products. One example of such coated products is galvanneal-coated steel. The demand for galvanneal coated steel spans various industries, largely the automotive industry. Within each industry, there are various consumers who require tests of different characteristics of the galvanneal-coated steel. There are significant differences among the various customer tests which determine whether a batch of galvanneal-coated steel meets a particular consumer's requirements.

In general, excessive powdering of the galvanneal coating is undesirable. Different consumers, however, require a resistance to powdering under different circumstances and therefore in response to different testing conditions.

In the automotive industry, for example, some of the major automotive manufacturers determine whether a shipment of galvanneal-coated steel satisfies their requirements by subjecting the galvanneal-coated steel to a V-bend test and determining whether the amount of powdering, if any, as a result of the V-bend test remains below a predetermined value. Some make this determination based on the results of a 90-degree-bend test. Still others apply a reverse Olsen test to the galvanneal-coated steel, and then determine whether the amount of powdering remains below the same or a different predetermined value.

In conducting a V-bend test, the sheet of galvanneal-coated steel is subjected to a free bend over a punch with a radius of 0.04 inch. The punch contacts the sheet only at certain locations while the rest of the sheet deforms with no tool contact. A visual rating then is performed on the compression side of the bend after unbending, or, alternatively, the samples are cleaned and weighed and a mass loss due to powdering is recorded. The standard 90-degree bend test is similar to the V-bend test, except that the punch radius is 0.12 inch and that the punch contacts the galvanneal-coated steel at all locations.

According to the reverse Olsen test, by contrast, the sheet of steel is dimpled first on one side using a 0.87 inch diameter ball to a height of 0.35 inch, and then the sheet is turned over and reverse dimpled to a height of 0.25 inch. Powdering is evaluated based on a visual rating on the outside of the dome after reverse dimpling, or alternatively the entire sample may be cleaned and measured for powdering mass loss.

The same specimen of galvanneal-coated steel may have different powdering tendencies in each of the different tests. Typically, the V-bend and reverse Olsen tests are used for testing light gage automotive products (usually 0.04 inch and less), while the 90 degree bend test is used to test both light and heavy gage galvanneal-coated products. Despite the typical uses for each test, each consumer chooses a particular one or combination of the tests. Not every consumer's choice, however, coincides with what is typical. When ordering a galvanneal-coated product, the consumer also might specify certain characteristics in the galvanneal-coated steel. Examples of such characteristics are the coating weight, iron content, gage, grade and/or coating phase composition.

It is then left to the manufacturer to produce a galvanneal-coated product which, in addition to having the specified characteristics, satisfies the particular powdering test(s) used by the consumer.

Heretofore, manufacturing and product parameters have been determined on a trial-and-error basis. Process control and classification of the resulting products also have been performed on a similar basis. The typical trial-and-error methodology involves setting certain manufacturing and product parameters, producing galvanneal-coated steel using such parameters, and testing the resulting galvanneal-coated steel to determine whether it satisfies the requirements of the particular consumer. This process typically requires several iterations before a satisfactory result is achieved. A considerable amount of time and resources therefore are expended before manufacturing of the actual product can even begin.

While some experienced manufacturers may have hunches about how to set the manufacturing and product parameters to generate a product containing the desired characteristics and resistance to powdering, such hunches often prove to be unreliable. The "hunch" method also is impractical because, even if it were reliable in some instances, it is limited to experienced manufacturers. Manufacturers who lack experience are far less likely to achieve favorable results using the "hunch" method.

Despite the disadvantages of the trial-and-error and hunch methods, the absence of any reliable alternative techniques for determining which manufacturing and product parameters will satisfy certain tests, has made the trial-and-error and hunch methods the primary source of manufacturing and product parameters. Considerable resources and time therefore are being wasted before the manufacturing process can even begin.

Once manufacturing begins, there is little guidance on how often a product should be tested to determine whether it continues to satisfy the particular consumer's set of requirements. Testing therefore might be performed at an insufficient frequency to detect flaws, or, alternatively, if the manufacturer is cautious, the testing might be performed too frequently. Since testing can be an expensive and time consuming process, testing at a frequency which is higher than necessary is wasteful. There is consequently a need for a method of determining how often to test a product based on a prediction of whether a particular product will provide poor, marginal, or good powdering resistance, and what the probability is that the particular product will fall within each category of poor, marginal, or good.

If a product fails to satisfy a particular consumer's requirements, there is little guidance on which parameters to modify and how to modify those parameters in order to maximize the likelihood that the resulting product will satisfy the particular consumer's requirements. The existing trial-and-error and hunch-based techniques are wasteful, as indicated above. A need therefore exists in the art for a method of performing process control based on an analysis and prediction of galvanneal powdering in different powdering tests.

There is also a need for a method of classifying products based on an analysis and prediction of galvanneal powdering in different powdering tests. Such classifications could be used to determine which powdering tests a particular product has a higher probability of satisfying. This information, in turn, could be used to determine which tests ultimately are performed on the product and to which consumer(s) such products might be acceptable. In this regard, the classifications could be used to determine distribution channels of the product. Since the present methods involve trial-and-error or hunch-based techniques, the existing methods of determining which tests are performed may result in an excessive number of tests. Time and resources therefore tend to be wasted under the present manufacturing schemes.

In order to avoid such waste, Applicants have attempted to predict, based on desired product characteristics and the particular powdering tests which are to be conducted on the product, which combinations of manufacturing and product parameters will prove to be successful under each of the different tests. Initially, data from over 1000 powdering test runs was compiled into a database, along with data on the coating and steel properties of the tested product. The data was obtained from research lab notebooks which, in turn, were used over a multiple year period to document powdering tests on a plurality of different samples.

Attempts were made to identify trends in these different tests based on large sample populations. Traditional regression analyses of the data, however, proved unsuccessful because of significant scatter which was observed in most of the powdering data. There is little, if any, benefit to being able to predict a value for powdering mass loss in a test, if a large prediction error band accompanies it. The same is true for other databases where only a few of the factors contributing to the measured response are known and are under control.

Another problem with using traditional regression analysis on the data arises because of differences in how the powdering was quantified in each of the various powdering tests. A visual ranking based on standard charts, for example, is a fast and simple method of quantifying powdering loss. This approach, however, is flawed to some extent in that the tape which is used in the ranking process only picks up the powder on the surface. The severity of the powdering therefore can be underestimated. In addition, a considerable overlap in ratings is observed when plotted against critical galvanneal coating variables, making it difficult to predict a future response.

When the severity of powdering is quantified using a mass loss quantification technique, instead of the visual rating technique, the results are far more accurate. The improvement in accuracy stems from the fact that the actual mass lost because of powdering is what gets measured. This technique, however, is time consuming and there is considerable scatter in the measured mass loss from similar coatings. The considerable scatter, in turn, tends to negate the advantages of measuring the powdering so accurately.

The visual rating technique therefore lacks accuracy, and the mass loss technique lacks precision. In addition, correlations between visual rating schemes and mass loss measurements tend to be poor, suggesting that the different coating variables affect these results somewhat differently. Because of these difficulties in analyzing powdering test data, Applicants' prior attempts to develop methods to accurately predict powdering rating and mass loss have not been successful.

Since the existing techniques of basic trial-and-error or hunch-based parameter determination are less than satisfactory, there is a continuing need in the art of manufacturing galvanneal-coated steel, for a method of determining product parameters based on analysis and prediction of galvanneal powdering in different powdering tests.

A need also exists for a method of analyzing data on galvanneal powdering, and for predicting, based on such data, the quality of galvanneal powdering resistance which can be expected in response to different powdering tests, as a function of certain parameters. The need for such prediction capabilities extends not only into the determination of product parameters at the product development stage, prior to actual production, but also into process control during production.

Since some galvanneal-coated steel products will react differently depending on which powdering test is being performed, there also is a need in the art for a method of classifying such products based on a prediction of their responses to the different powdering tests.

SUMMARY OF THE INVENTION

A primary object of the present invention is to provide a computer-based system and method which are capable of overcoming the foregoing problems and satisfying the various needs in the art.

In order to achieve this and other objects, the present invention provides a method of determining a range of values for at least one variable product parameter of a product to be manufactured. The method comprises the steps of: providing a computer-readable database which contains product data on several previously manufactured products, as well as test result data for each of the previously manufactured products, the test result data including information on how the previously manufactured products performed when subjected to a first testing procedure; analyzing the product data and the test result data using a computer-implemented classification and regression tree analysis; generating, based on the computer-implemented classification and regression tree analysis, a binary decision tree having multiple decision result branches, each decision result branch being defined by a result of a binary decision on one of a plurality of product parameters; applying at least one desired value of a product parameter to the binary decision tree to eliminate from consideration any decision result branches which are inconsistent with the desired value(s); and determining the range based upon which path through the decision result branches which were not eliminated from consideration, yields a best probability that a product with the desired value(s) will respond favorably to the first testing procedure.

The present invention also provides a method of performing process control in a manufacturing process. The method comprises the steps of: providing a computer-readable database which contains product data on several previously manufactured products, as well as test result data for each of the previously manufactured products, the test result data including information on how the previously manufactured products performed when subjected to a first testing procedure; analyzing the product data and the test result data using a computer-implemented classification and regression tree analysis; generating, based on the computer-implemented classification and regression tree analysis, a binary decision tree having multiple decision result branches, each decision result branch being defined by a result of a binary decision on one of a plurality of parameters; applying values of product parameters to the binary decision tree to eliminate from consideration any decision result branches which are inconsistent with such values; determining at least one probability, based on the values of product parameters, that a product with such values of product parameters will respond favorably to the first testing procedure; and adjusting at least one step in the manufacturing process if the probability(ies) is (are) outside of an acceptable range.

According to another aspect of the present invention, a method of classifying a product is provided. The method comprises the steps of: providing a computer-readable database which contains product data on several previously manufactured products, as well as test result data for each of the previously manufactured products, the test result data including information on how the previously manufactured products performed when subjected to a first testing procedure; analyzing the product data and the test result data using a computer-implemented classification and regression tree analysis; generating, based on the computer-implemented classification and regression tree analysis, a binary decision tree having multiple decision result branches, each decision result branch being defined by a result of a binary decision on one of a plurality of parameters; applying values of product parameters associated with the product to the binary decision tree; determining at least one probability, based on the values of product parameters, that the product will respond favorably to the first testing procedure; and classifying the product as being good, marginal or poor, based on the probability(ies).

According to yet another aspect of the present invention, a method of classifying a product comprises the steps of: providing a computer-readable database which contains product data on several previously manufactured products, as well as test result data for each previously manufactured product, the test result data including information on how the previously manufactured products performed when subjected to a first testing procedure and information on how at least some of the previously manufactured products performed when subjected to at least a second testing procedure; analyzing the product data and the test result data using a computer-implemented classification and regression tree analysis; generating, for each of the first and at least a second testing procedures, a binary decision tree based on the computer-implemented classification and regression tree analysis, each binary decision tree having multiple decision result branches, each decision result branch being defined by a result of a binary decision on one of a plurality of parameters; applying values of product parameters associated with the product to each binary decision tree; determining, based on such values of product parameters as applied to each binary decision tree, probabilities of the product responding favorably when subjected to the first and at least a second powdering tests; and classifying the product based on which of the first and at least a second testing procedures the product is most likely to satisfy as determined by the probabilities associated with each binary decision tree.

Still another aspect of the present invention provides a computer system for use in determining product parameters. The computer system comprises a storage device, an input device, and a processor. The storage device contains a parameter selection program based on at least one binary decision tree derived from a classification and regression tree analysis of: a) product data on previously manufactured products, and b) test data on how such previously manufactured products respond to at least one testing procedure. The input device receives information indicative of at least one desired value of product parameter. The processor is connected at least indirectly to the storage device and the input device. The processor is adapted to perform the parameter selection program by applying the information to the binary decision tree(s) and generating an output signal indicative of at least one range of at least one other product parameter which, according to the binary decision tree(s), contains values of the other product parameter(s) which enhance a probability that a product with the desired value(s) of product parameter will respond favorably to the testing procedure(s).

Yet another aspect of the present invention provides a computer system for use in performing process control. The computer system comprises a storage device, an input device, a processor, and a control mechanism. The storage device contains a prediction program based on at least one binary decision tree derived from a classification and regression tree analysis of: a) product data on previously manufactured products, and b) test data on how such previously manufactured products respond to at least one testing procedure. The input device receives information indicative of at least one product parameter. The processor is connected at least indirectly to the storage device and the input device. The processor is adapted to perform the prediction program by applying the information to the binary decision tree(s) and generating an output signal indicative of at least one probability that a product with the product parameter(s) will respond favorably to the testing procedure(s). The control mechanism is connected at least indirectly to the processor and is responsive to the output signal. The control mechanism is adapted to adjust at least one step in a manufacturing process if the probability(ies) is (are) outside of an acceptable range.

Also provided by the present invention is a computer system for use in classifying products. The computer system includes a storage device, an input device, a processor, and a classification mechanism. The storage device contains a prediction program based on at least one binary decision tree derived from a classification and regression tree analysis of: a) a product data on previously manufactured products, and b) test data on how such previously manufactured products respond to at least one testing procedure. The input device receives information indicative of at least one product parameter. The processor is connected at least indirectly to the storage device and the input device. The processor is adapted to perform the prediction program by applying the information to the binary decision tree(s) and generating an output signal indicative of at least one probability that a product with the product parameter(s) will respond favorably to the testing procedure(s). The classification mechanism is responsive to the processor, and identifies the product as good, marginal, or poor based on the probability (ies).

The above and other objects and advantages will become more readily apparent when reference is made to the following description taken in conjunction with the accompanying drawings.

DESCRIPTION OF PREFERRED EMBODIMENTS

While the present invention will be described in the context of manufacturing galvanneal-coated steel products (e.g., strips, sheets, plates, rods, wires, and the like), it is understood that the present invention is not limited to use on such semi-finished products or their methods of manufacture. To the contrary, the present invention can be applied to processes of manufacturing any semi-finished steel product irrespective of its form. Coated and uncoated products can be manufactured according to the present invention. The present invention also applies to the manufacturing of substrates other than steel (e.g., aluminum), regardless of whether those substrates are coated, uncoated, or semi-finished.

Generally, the present invention provides computer-implemented based systems and methods of determining product parameters, performing process control, and/or classifying products. These computer-based systems and methods analyze previous responses to different iterations of one or more tests and, based on this analysis, predict responses to future tests.

Figure 1:
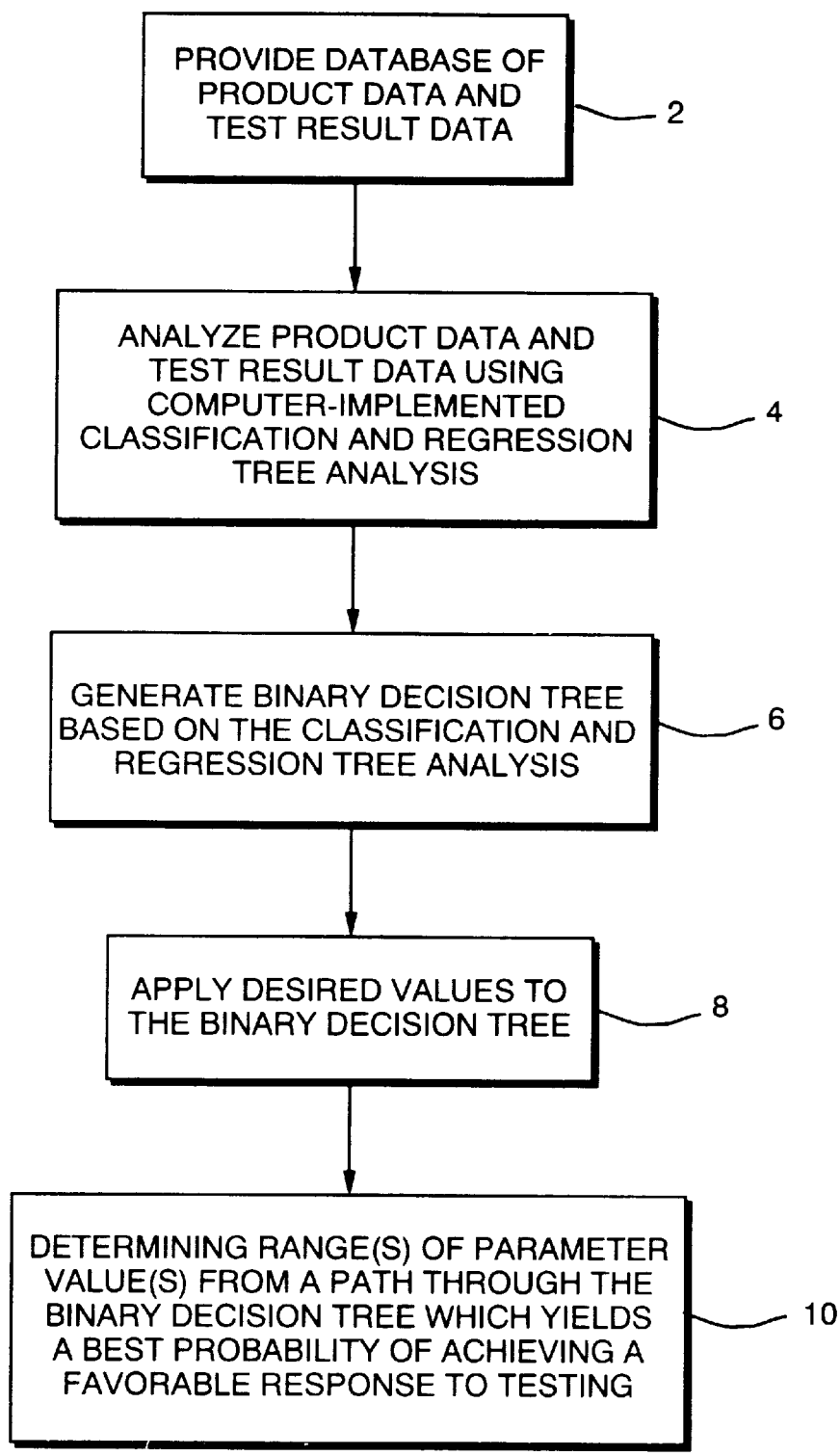
FIG. 1 is a flow chart of a method for determining product parameters according to a preferred implementation of the present invention.

During the product development stage of a manufacturing process, the computer-based system and method of determining product parameters become especially useful. As shown in FIG. 1, a preferred implementation of the method involves determining a range of values for at least one variable product parameter of a product to be manufactured.

As an initial step in the method, a computer-readable database is provided (step 2 in FIG. 1). The database contains historical product data on several previously manufactured products, as well as test result data for each of the previously manufactured products. The test result data includes information on how the previously manufactured products performed when subjected to a first testing procedure.

In the context of manufacturing galvanneal-coated steel, the test result data may include data indicative of how well the previously manufactured galvanneal-coated steel responded to testing. The testing itself may include tests of the coating's resistance to powdering, cracking, and/or the like. The test result data preferably is categorized as good, marginal, and poor. Preferably, the distinction between the good, marginal, and poor categories is made based on where each test result falls among the other test results. The test results within the top 25% of all test results, for example, are catagorized as good test results. The test results within the bottom 25% of all test results, are catagorized as poor results. The marginal catagory then is defined by the rest of the test results (i.e., the middle 50% of all test results). The present invention, of course, is not limited to the percentages described in this example. Other percentages can be used depending, for example, on the distribution of the data results.

In the context of manufacturing galvanneal-coated steel, the product data may include, among other things, the product's gage, coating weight, iron content, grade, coating phase composition, or combinations of such parameters. A correlation is provided in the computer-readable data-base between the test result data for each previously manufactured product and its parameters (i.e., the product data).

Once the computer-readable database has been established, the product data and test result data contained in the database are analyzed using a computer-implemented classification and regression tree analysis (step 4 in FIG. 1). This analysis can be performed using commercially available data mining software. An example of such software is available from Salford Systems of San Diego, Calif., and is marketed under the trademark CART™.

The CART™ software can be loaded into a conventional desk-top computer, and provides a Windows™-based interface between the user and the CART™ software. The CART™ software is compatible with several commercially available computer operating systems, including Windows 3.X, Windows 95, Windows NT, Mac OS, UNIX, IBM MVS and CMS. The CART™ software also is supported by several commercially available hardware systems, including Intel PCs, Sun, SGI, HP, Digital Alpha, VAX, and IBM S6000 machines. The CART™ software also includes a data-translation engine capable of providing data conversion from more than seventy file formats, including conventional statistical-analysis packages, such as SAS® and SPSS; conventional databases, such as Oracle and Informix; and conventional spreadsheets, such as Microsoft Excel and Lotus.

The computer-implemented classification and regression tree analysis therefore can be performed using the CART™ software and any one of several combinations of commercially available hardware, software, and/or firmware elements.

Based on the computer-implemented classification and regression tree analysis, a binary decision tree is generated (step 6 in FIG. 1). The binary decision tree has multiple decision result branches. Each decision result branch is defined by a result of a binary decision on one of a plurality of product parameters.

The multiple decision result branches include terminal branches and intermediate branches. Each intermediate branch is logically defined between two binary decisions. The terminal branches, by contrast, are followed logically by no other binary decisions.

If different testing procedures are used and such testing procedures can have different results on the same product, then a binary decision tree will be generated for each testing procedure. Thus, when powdering test results are used as the test result data, a separate binary decision tree is generated for each of the powdering test types. One binary decision tree will be generated for the V-bend test, another for the 90-degree-bend test, and still another for the reverse Olsen test.

In generating each binary decision tree, three probabilities are determined for each of the terminal branches. A first of the three probabilities corresponds to the probability of achieving a "good" test result when the product has a combination of parameter values which leads to that particular terminal branch. The second and third probabilities similarly represent the probabilities that "marginal" and "poor" test results, respectively, will be achieved by a product having a combination of parameter values which leads to the same terminal branch. All three of the probabilities are determined based on the aforementioned classification and regression tree analysis. While the use of three probabilities is preferred with galvanneal material, other products may satisfactorily implement the invention with at least two probabilities or more than three.

In defining each binary decision, the classification and regression tree analysis determines which of the various product parameters and values thereof achieve the largest differences between the first and third probabilities when those values and product parameters define the split between two groups of the test result data. The first binary decision then is defined at the particular value and based on the particular parameter which together provide the largest differences. Thus, if the analysis determines that the largest differences between the first and third probabilities is achieved by splitting the products into a first group of products having a gage greater than 0.058 inch and a second group having a gage equal to or less than 0.058, then the binary decision will be made at that value (0.058 inch) and based on that particular parameter (the gage). Subsequent binary decisions are defined using the same approach.

The terms "value" and "values" are used herein in their broadest sense and are not limited to numerical values. In the context of galvanneal-coated steel, for example, the grade of steel may be one parameter which appears in the binary decision tree. The binary decision on that parameter might be whether the grade is IF, interstitial free. The possible "values" in that case are "yes" and "no", not numerical values.

During product development, the end user specifies one or more values for certain parameter(s) of the product. Such values are referred to herein as "desired" values. The desired values then are applied to the binary decision tree (step 8 in FIG. 1). Any decision result branches which are inconsistent with the desired values are likely not to be successful and are initially eliminated from consideration.

Of the paths which remain through the binary decision tree, one path typically will yield a highest probability that a product with the desired value(s) will respond favorably to the particular testing procedure upon which the test result data is based. This path determines certain ranges of product parameter values (step 10 in FIG. 1). Products with parameter values within the particular ranges which are dictated by that path will have an enhanced probability of responding favorably to the testing procedure. Product development efforts therefore can be directed to products having parameters within those ranges. This represents a significant advance over the traditional trial-and-error/hunch-based approaches to product development.

The method of the present invention was carried out on product data and test result data generated over several years from galvanneal-coated products manufactured by Bethlehem Steel Corporation, Applicants' assignee. The testing procedures which were used included V-Bend tests, 90-Bend tests, and reverse Olsen tests. The tests were carried out using different data gathering techniques, including visual rating schemes, powdering width schemes, and mass loss rating schemes. The following table summarizes the attributes of the product data and test result data:

| CATAGORY | V-BEND TEST | 90-BEND TEST | REVERSE OLSEN (MASS LOSS) | REVERSE OLSEN (VISUAL RATING) |
|---|---|---|---|---|
| # data points analyzed | 671 | 400 | 185 | 288 |
| Range in gage for sample products (in inches) | 0.028–0.06 | 0.0367–0.079 | 0.029–0.04 | 0.029–0.051 |
| Coating Weight Range for sample products (in grams per meter$^2$) | 32.1–123.6 | 41.9–97.7 | 44.7–64 | 44.7–72.5 |
| Fe Weight % range for sample products | 0.39–17.9 | 8.1–14.5 | 2.5–12.2 | 5.3–12.7 |
| Source followed by the number of data points obtained from the source in parenthesis | Lab coated (397) Burns Harbor (191) Lackawanna (24) Sparrows Point (20) Competition (mostly A112 coated at USX) (56) | Lackawanna (290) Burns Harbor (110) | Burns Harbor | Burns Harbor (250) Competition (mostly A112 data points coated at USX) (38) |
| Grades with number of data points in parenthesis For the non-IF sample products, no further grade information was available. | A107-(213) Non-IF (124) 13612-(106) A106-(99) A112-(46) AW611-(37) A111-(28) Rephos non-IF-(8) A105-(4) IH207-(4) | 1102-(176) A603-(114) A106-(110) | A105-(89) A111-(62) A112-(32) A107-(2) | A105-(81) A111-(78) A112-(72) A107-(30) Non-IF-(14) B40pk-(11) A106-(2) |

Analysis of V-Bend Powdering Test Based on Mass Loss Rating Scheme

Figure 2A:
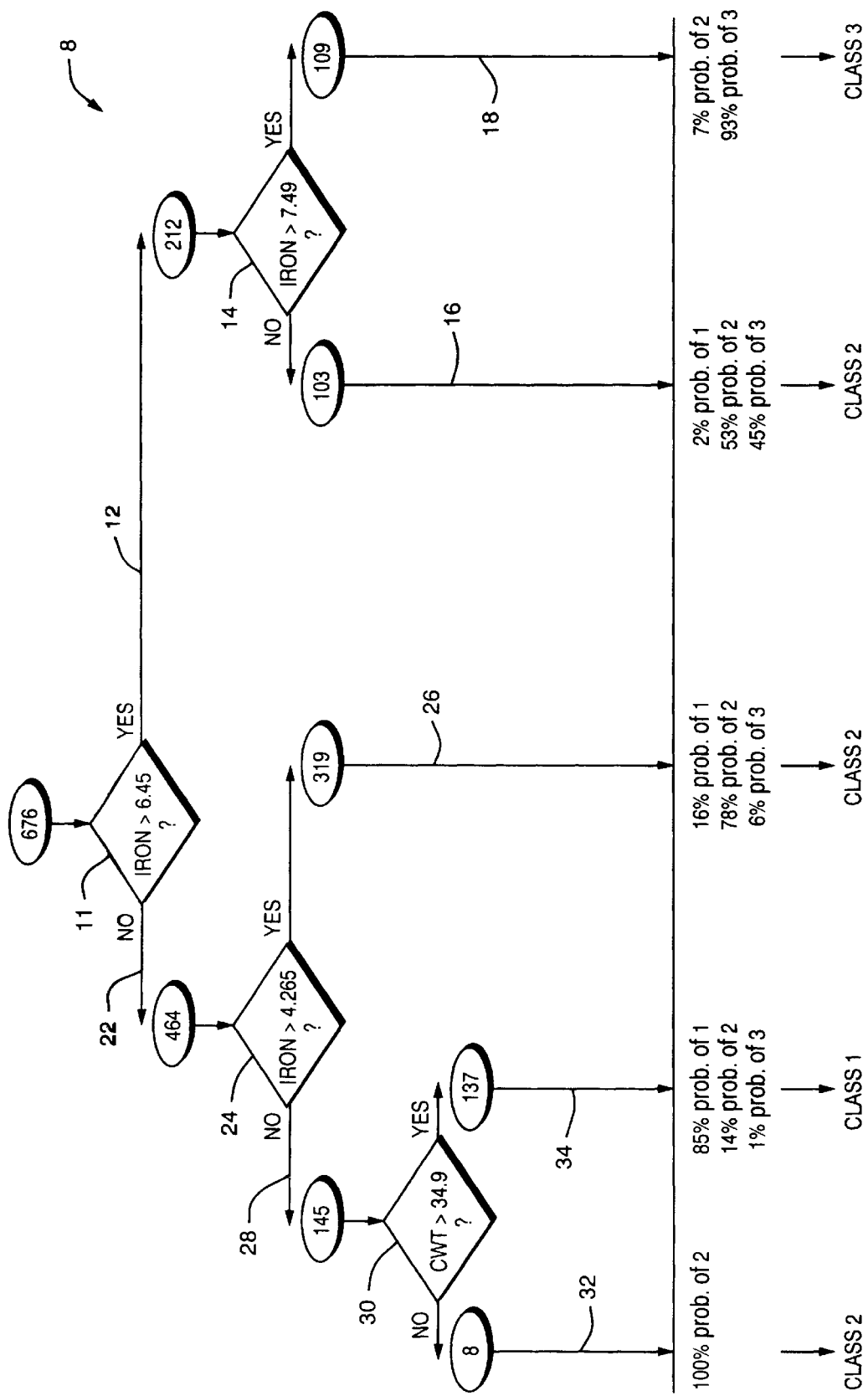
FIG. 2A is a binary decision tree according to a first implementation of the present invention.

An exemplary binary decision tree is shown in FIG. 2A. The binary decision tree 8 was generated based on test results from V-bend powdering tests that were performed on 676 samples of galvanneal-coated steel. The test result data was gathered using a mass loss rating scheme, whereby the amount of powdering was measured based on a reduction in the mass of the coating.

The number of sample products in each branch of the tree 8 is indicated by a number contained in an oval. The test result data was divided into groups of "good", "marginal", and "poor" test results. A mass loss less than or equal to 3.3 milligrams was deemed to constitute a "good" test result, a mass loss between 3.3 milligrams and 8.1 milligrams was deemed to constitute a "marginal" test result, and a mass loss greater than 8.1 milligrams was deemed to constitute a "poor" test result.

Based on the classification and regression tree analysis, the largest differences between the probability of achieving "good" test results and the probability of achieving "poor" test results was provided by distinguishing the product samples with an iron content greater than 6.45 grams/meter$^2$ from those with an iron content less than or equal to 6.45 grams/meter$^2$. Accordingly, the first binary decision 11 in the binary decision tree 8 of FIG. 2A is whether the iron content exceeds 6.45 grams/meter$^2$.

As shown in FIG. 2A, two-hundred and twelve (212) of the sample products have an iron content exceeding 6.45 grams/meter$^2$. Those sample products define an intermediate branch 12 of the binary tree 8. The number of products in each branch 12 is designated by a number within a circle.

The intermediate branch 12 leads to another binary decision 14. The binary decision 14 also is based on the iron content of the samples. In particular, it was determined by the classification and regression tree analysis that the largest difference between the probability of achieving "good" or "marginal" test results and achieving "poor" test results using products which fall into the intermediate branch 12, was provided by distinguishing the products with an iron content greater than 7.49 grams/meter$^2$ from those having an iron content less than or equal to 7.49 grams/meter$^2$.

The two branches which logically follow the binary decision 14 are terminal branches 16,18. Terminal branch 16 represents 103 samples having an iron content less than or equal to 7.45 grams/meter$^2$. Terminal branch 18, by contrast, represents 109 samples having an iron content greater than 7.49 grams/meter$^2$.

Each of the terminal branches 16,18 is associated with first, second, and third probabilities that a product qualifying for that particular terminal branch will exhibit "good", "marginal", or "poor" testing results, respectively. Based on which of these probabilities is highest, each terminal branch 16,18 is classified as a class 1, class 2, or class 3 terminal branch. In a class 1 terminal branch, the probability of achieving "good" test results is higher than the probability of achieving "marginal" test results and also is higher than the probability of achieving "poor" test results. Class 2 and 3 terminal branches, by contrast, are those in which the probability of achieving "marginal" test results and "poor" test results, respectively, are the highest.

As shown in FIG. 2A, the terminal branches 16,18 are class 2 and class 3 terminal branches, respectively. Thus, according to the binary decision tree 8, the probability of achieving "good" test results from a galvanneal coating with an iron content greater than 6.45 grams/meter$^2$ is not as high as that of achieving "marginal" or "poor" test results. The probability of achieving "good" test results is even less when the iron content is greater than 7.49 grams/meter$^2$. Thus, based on the binary decision tree 8, product development efforts on products which will be subjected to a mass loss rating scheme in a V-bend powdering test, should be directed to products with iron contents that do not exceed 6.45 grams/meter$^2$.

When the iron content is less than or equal to 6.45 grams/meter$^2$, as it was for 464 of the sample products, those products follow an intermediate branch 22. The intermediate branch 22 leads to another binary decision 24. The other binary decision 22 also is based on the iron content of the product.

An iron content greater than 4.265 grams/meter$^2$ leads to a terminal branch 26, while an iron content less than or equal to 4.265 grams/meter$^2$ leads to an intermediate branch 28. The terminal branch 26 is deemed a class 2 terminal branch because its first, second, and third probabilities are 16%, 78%, and 6%, respectively. Notably, there is only a 16% probability that products with an iron content between 4.265 grams/meter$^2$ and 6.45 grams/meter$^2$ will achieve "good" test results.

The intermediate branch 28 applies to 145 of the samples and leads to another binary decision 30. In the case of the binary decision 30, it was determined by the classification and regression tree analysis that the largest difference between the probability of achieving "good" test results and that of achieving "poor" or "marginal" test results from samples in the intermediate branch 28, was provided by distinguishing the samples with a coating weight greater than 34.9 grams/meter$^2$ from those having a coating weight less than or equal to 34.9 grams/meter$^2$. The binary decision 30 therefore is whether the coating weight exceeds 34.9 grams/meter$^2$.

The results of the binary decision 30 are represented by two terminal branches 32,34. The terminal branch 32 is a class 2 terminal branch because all (100%) of the samples provide only "marginal" test results. Terminal branch 32 applies to only eight of the samples.

The terminal branch 34, by contrast, applies to 137 of the samples. The first, second, and third probabilities associated with terminal branch 34 are 85%, 14%, and 1%, respectively. Terminal branch 34 therefore is a class 1 terminal branch.

Thus, according to the binary decision tree 8, galvanneal-coated samples having an iron content less than or equal to 4.265 grams/meter$^2$ (a first range) and a coating weight greater than 34.9 grams/meter$^2$ (a second range) have an 85% probability of providing favorable test results when subjected to a mass loss rating scheme in a V-bend test. Product development efforts therefore should be directed to products which have their product parameter values within those ranges dictated by the path through intermediate branches 22 and 28 and terminal branch 34.

A particular consumer, however, may insist on product parameter values which are not consistent with such ranges, that is, values which deviate from the path through branches 22, 28 and 34. In that case, all paths which are inconsistent with the consumers requirements are eliminated for consideration. The remaining paths then are evaluated and one is selected based on its probability of achieving a favorable response to testing.

If, for example, the consumer insists on having a product with an iron content greater than 7 grams/meter, then all of the paths which include intermediate branch 22 are eliminated from consideration. The only remaining paths are a first path through intermediate branch 12 and terminal branch 16 and a second path through intermediate branch 12 and terminal branch 18. Terminal branch 16 is a class 2 terminal branch, while terminal branch 18 is a class 3 terminal branch. Of the paths which are consistent with the consumer's desired values in this example, the path through terminal branch 16 tends to suggest better test results. Thus, product development efforts for that particular consumer should be directed to products with an iron content ranging between 7 grams/meter$^2$ and 7.49 grams/meter$^2$.

Figure 2B:
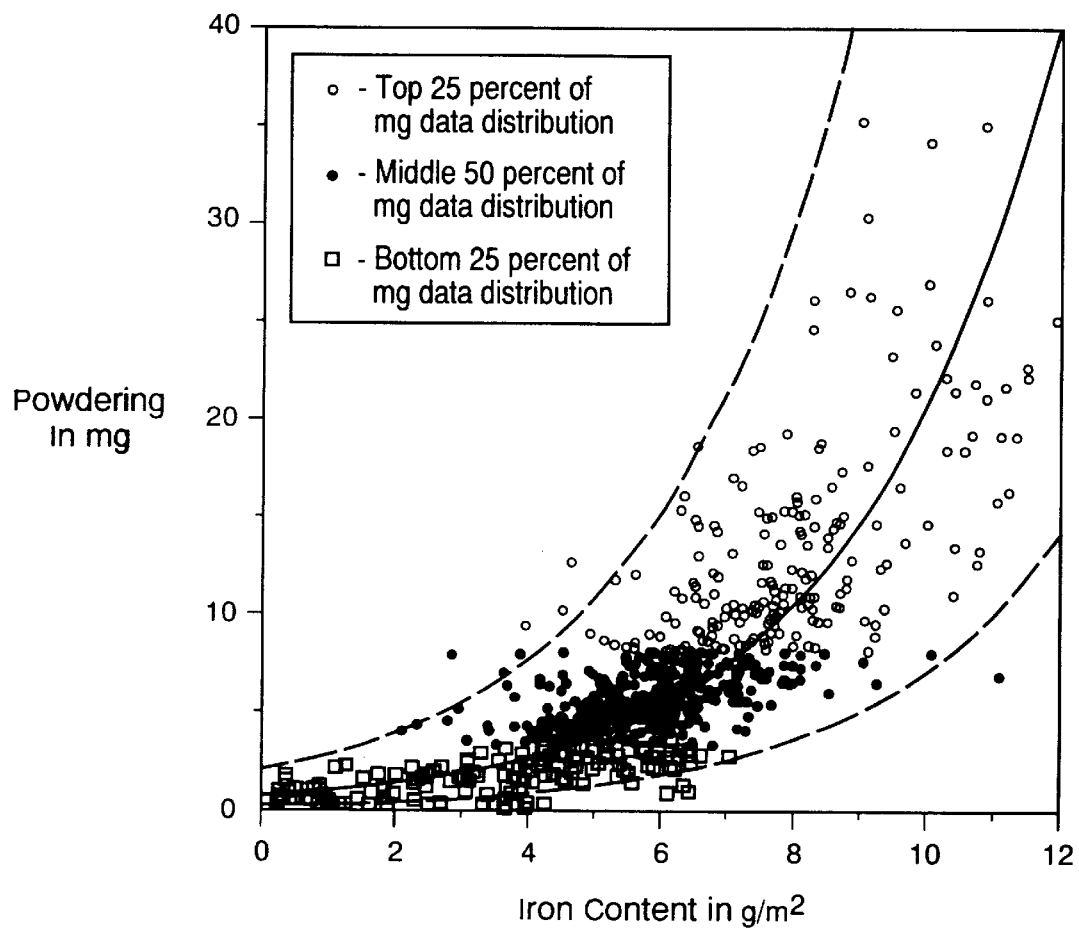
FIG. 2B is a graph of data used in the first implementation.

FIG. 2B is a graph of the test result data (powdering in milligrams) plotted as a function of iron content (in grams/meter$^2$). The broken lines in the graph represent the 95% prediction band for the mass loss measurement. The bottom 25%, middle 50%, and top 25% of the test result data in the graph represent the test results which are classified as "good", "marginal", and "poor", respectively. In this graph, as well as some of the other graphs which follow, the "good", "marginal", and "poor" test result data is represented by green, blue, and red data points, respectively. It can be appreciated from FIG. 2B that analysis based solely upon iron content will not permit accurate prediction of acceptable powdering, because, at 6% iron content, for example, good, marginal, and poor results are attained. Thus, a development program or process control correction could not be reliably based upon iron content analysis.

Figure 2C:
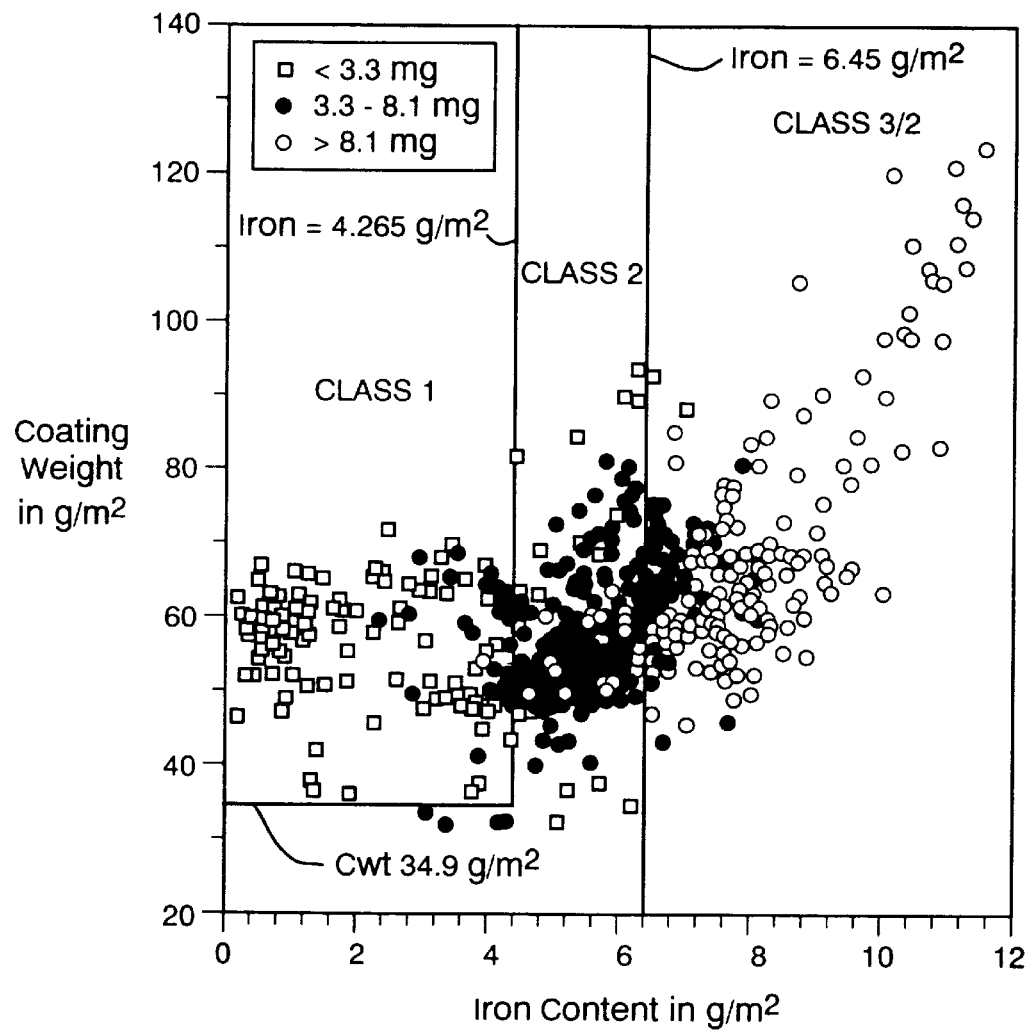
FIG. 2C is another graph of the data used in the first implementation.

FIG. 2C is a graph of the test result data (powdering in milligrams) plotted as a function of coating weight (in grams/meter$^2$) and iron content (in grams/meter$^2$). This graph visually demonstrates how well the binary decision tree 8 predicts whether the test result data will be "good", "marginal", or "poor" based on the ranges of product parameter values which, according to the binary decision tree 8, place the products into classes 1, 2, or 3/2. It can be seen in FIG. 2C that relatively few "marginal" results are located in the class 1 results, and that few "good" results are in the class 3/2 data. Hence, product development efforts or process control corrections may be relatively reliably based upon FIG. 2C and its results.

Figure 2D:
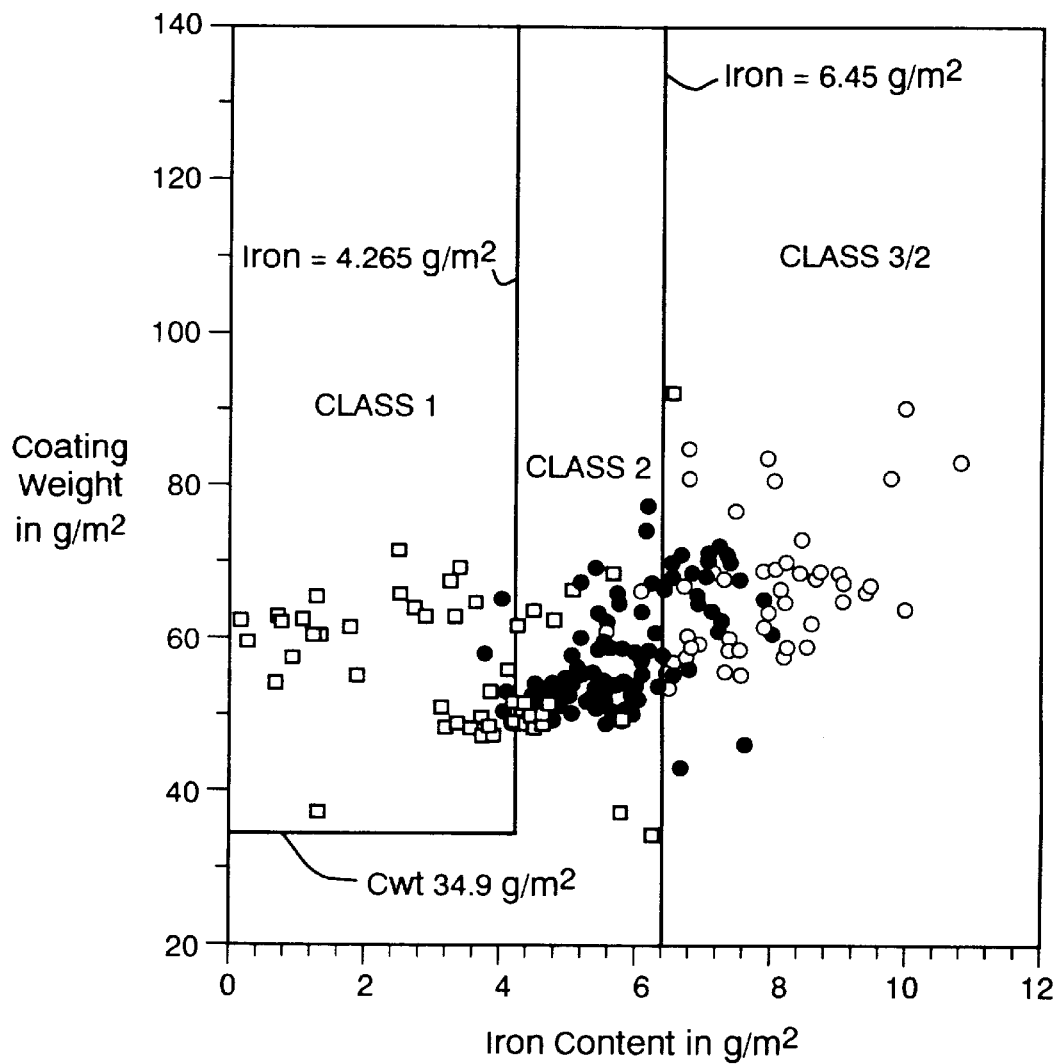
FIG. 2D is yet another graph of the data used in the first implementation.

FIG. 2D also is a graph of test result data (powdering in milligrams) plotted as a function of coating weight (in grams/meter$^2$) and iron content (in grams/meter$^2$). The test result data in FIG. 2D, however, is taken only with respect to a single grade of galvanneal-coated steel, namely, grade "A107". This graph also visually demonstrates how well the binary decision tree 8 predicts whether the test result data will be "good", "marginal", or "poor" based on the ranges of product parameter values which, according to the binary decision tree 8, place the products into classes 1, 2, or 3/2.

Figure 2E:
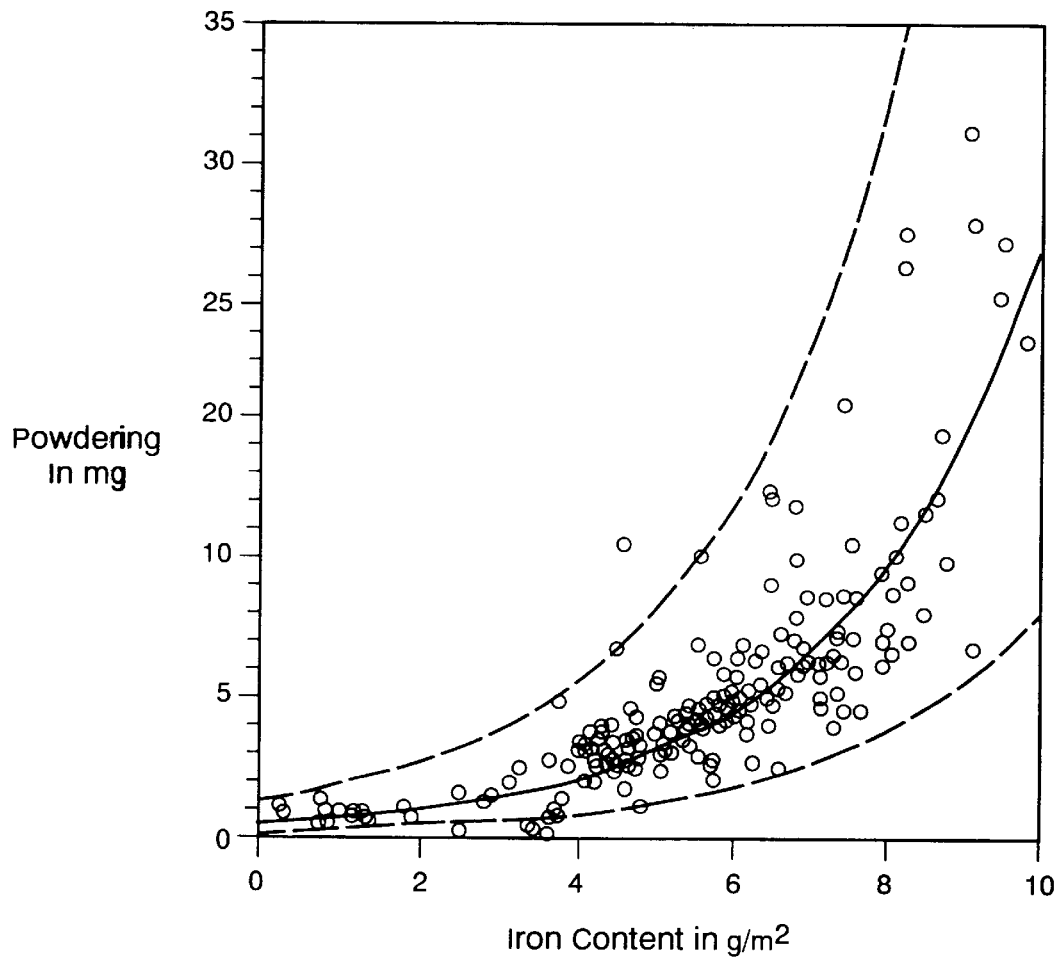
FIG. 2E is a graph of a regression curve fitting generated by conducting a traditional regression analysis on the test result data which was used in connection with FIG. 2D.

For purposes of contrast, FIG. 2E is a graph showing a regression curve fitting generated by conducting a traditional regression analysis on the same test result data which was used in connection with FIG. 2D. In FIG. 2E, the powdering mass loss (in milligrams) is plotted as a function of iron content (in grams/meter$^2$). As with FIG. 2A, the data is not able to provide accurate prediction of results.

Figure 2F:
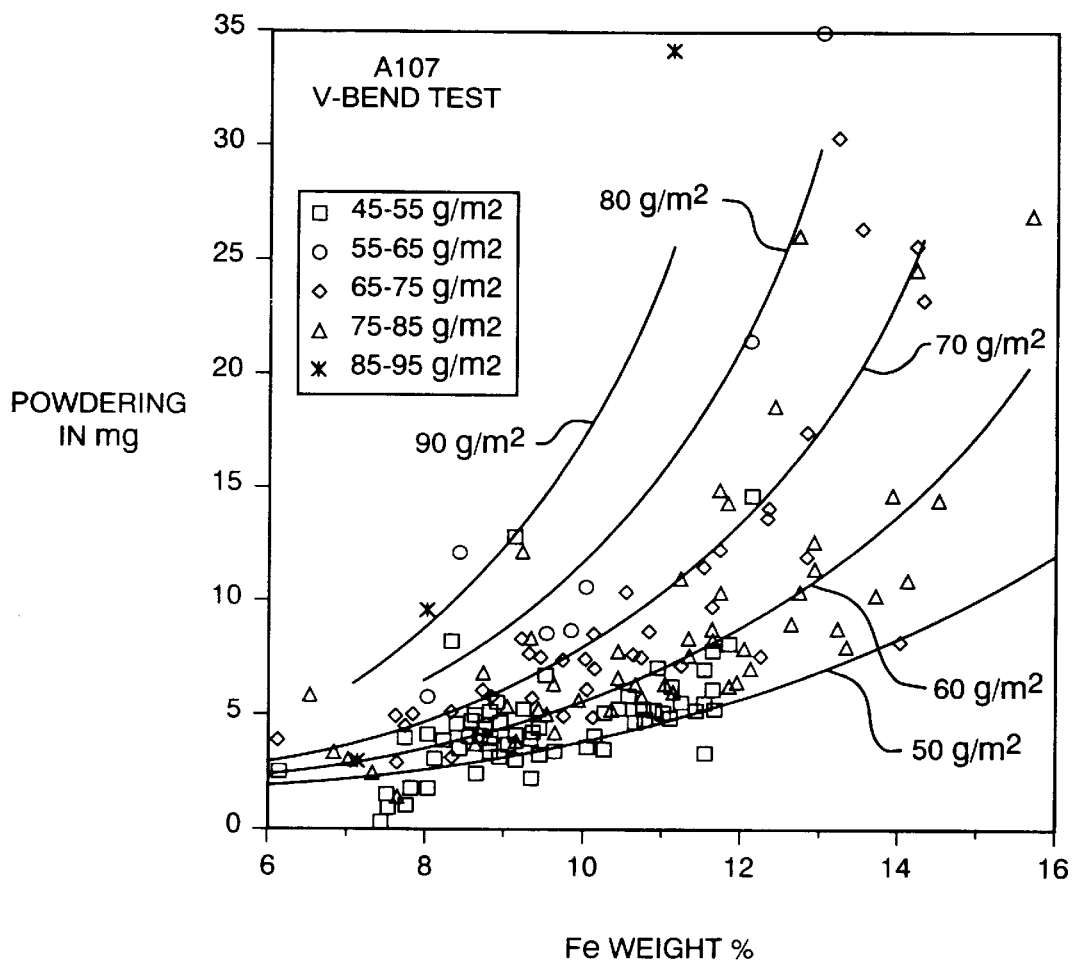
FIG. 2F is a graph showing the regression prediction curves which were generated using the regression analysis as was used in FIG. 2E.

FIG. 2F is a graph showing the regression prediction curves which were generated using the same regression analysis. In FIG. 2F, however, the powdering mass loss (in milligrams) is plotted as a function of iron weight percentage (Fe %) of the coating. FIG. 2F demonstrates one of the problems associated with traditional regression analysis in the context of manufacturing galvanneal-coated products. The product data for products having an iron weight percentage (Fe %) of the coating between 55 and 65 grams/meter$^2$ exhibit widely varying powdering behavior and do not obey the prediction curves.

The binary decision tree 8 of the present invention, by contrast, provides more accurate predictions, as demonstrated by FIGS. 2C and 2D. The improvement in accuracy provided by the present invention is further demonstrated by FIGS. 2G and 2H.

Figure 2G:
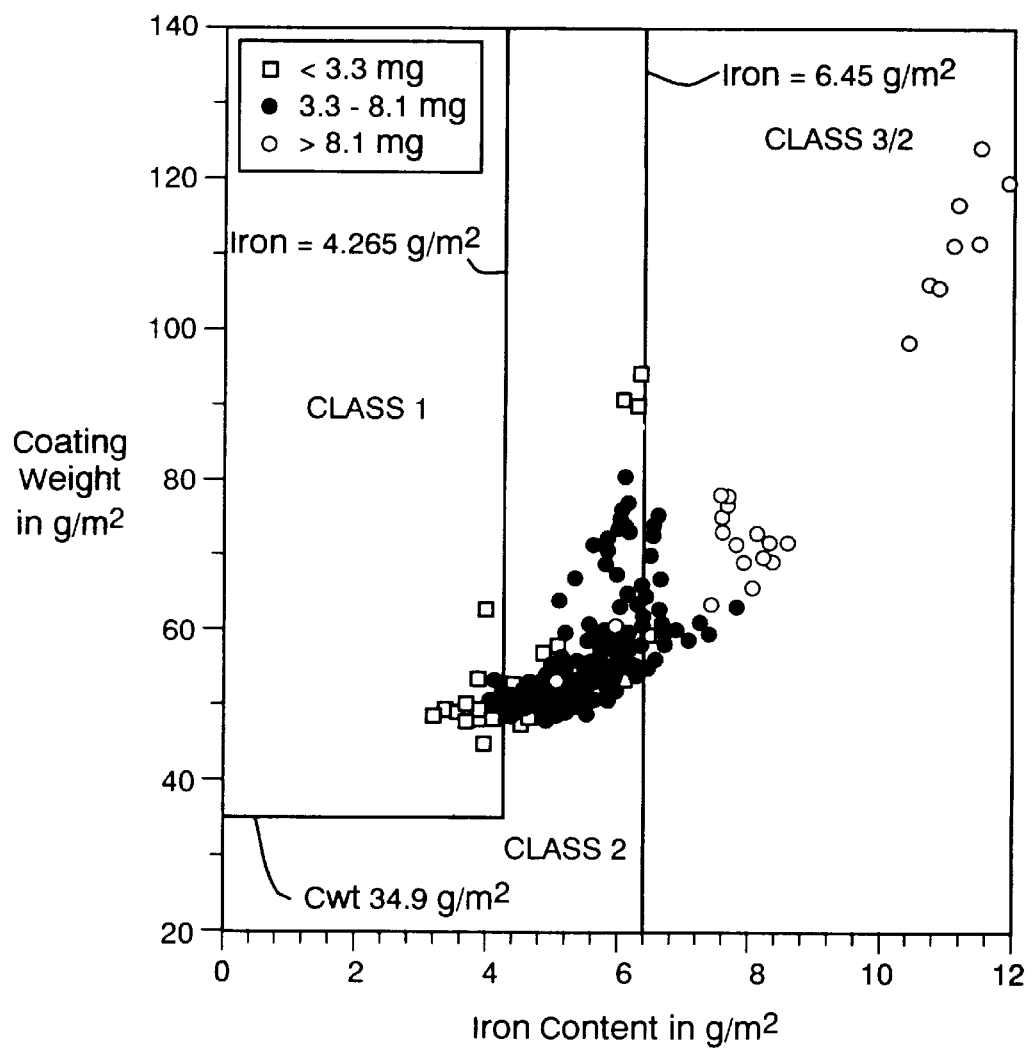
FIG. 2G is a graph of test result data generated using the same testing procedure which was used to gather the data of FIGS. 2C and 2D.

FIG. 2G is a graph of test result data generated using the testing procedure which was used to gather the data of FIGS. 2C and 2D. The product data and test result data in FIG. 2G, however, is limited to that which was gathered at Bethlehem Steel's Bums Harbor facility. The product data includes different grades and gages of the galvanneal-coated steel. The test result data, in FIG. 2G, is plotted as a function coating weight (in grams/meter$^2$) and iron content (in grams/meter$^2$), as suggested by the binary decision tree 8.

Figure 2H:
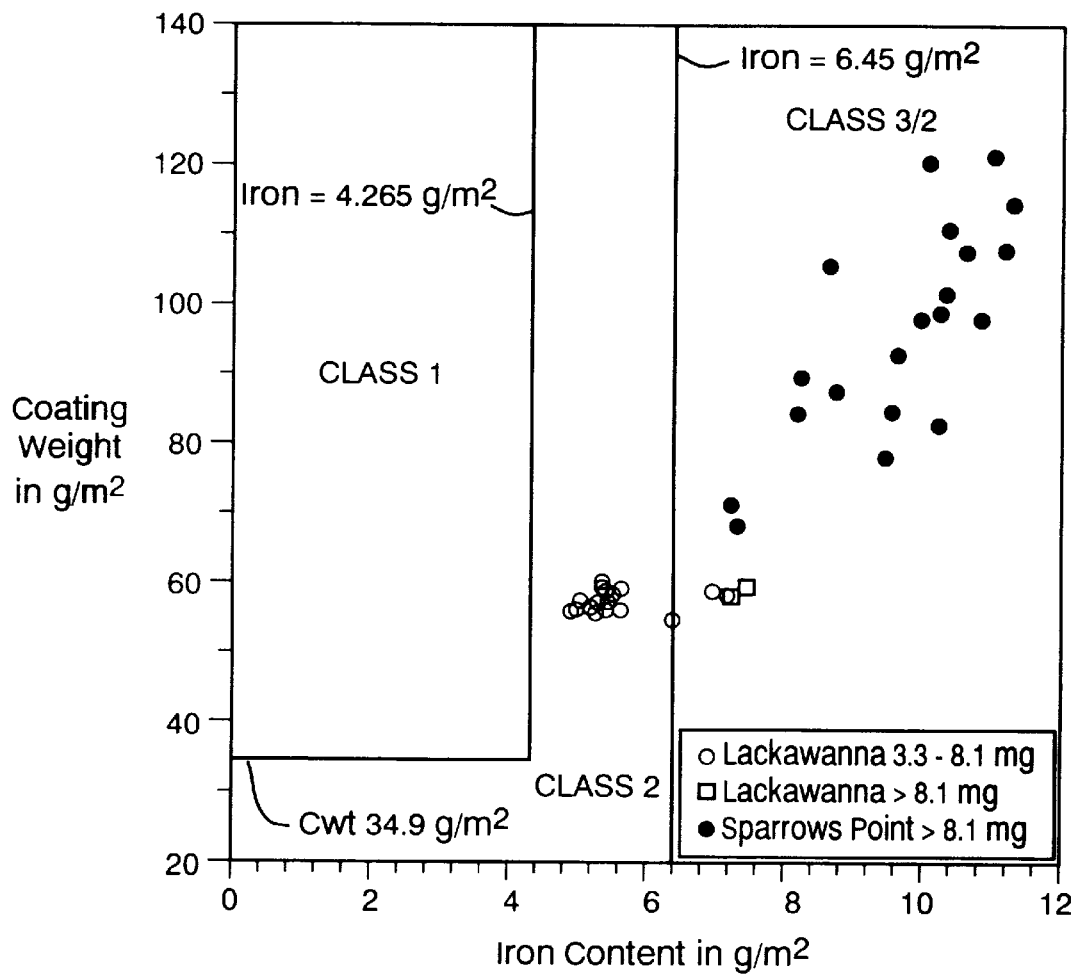
FIG. 2H is a graph of test result data generated using the testing procedure which was used to gather the data of FIGS. 2C and 2D.

FIG. 2H is a graph of test result data generated using the testing procedure which was used to gather the data of FIGS. 2C and 2D. The samples data and test result data in FIG. 2H, however, is limited to that which was gathered at Bethlehem Steel's Lackawanna and Sparrows Point facilities. The product data includes only non-IF grades of the galvanneal-coated steel. The test result data, in FIG. 2H, is plotted as a function coating weight (in grams/meter$^2$) and iron content (in grams/meter$^2$), as suggested by the binary decision tree 8. The test result data derived from the Lackawanna facility is shown using hollow circles, while that which was taken from the Sparrows Point facility is plotted using solid circles.

Despite the differences among the sources of the data in FIGS. 2G and 2H, the method of the present invention is able to reliably predict, based on the values of parameters along the axes of the graphs (i.e., coating weight and iron content), whether the test result data will be "good", "marginal", or "poor". This also represents a significant advance over traditional regression-based analyses.

Since different consumers apply different testing procedures, the method of the present invention can be implemented using different sets of test result data to generate respective binary decision trees for the different testing procedures.

Even each of the general categories of tests (e.g, V-bend tests, 90-bend tests, and the like) can be practiced using different rating schemes. V-bend tests, for example, can be implemented using a powdering width rating scheme. Alternatively, a mass loss rating scheme can be used when implementing the V-bend test. Each rating scheme represents a different testing procedure and provides different test result data.

Analysis of V-Bend Testing Based on Powdering Width Rating Scheme

Figure 3:
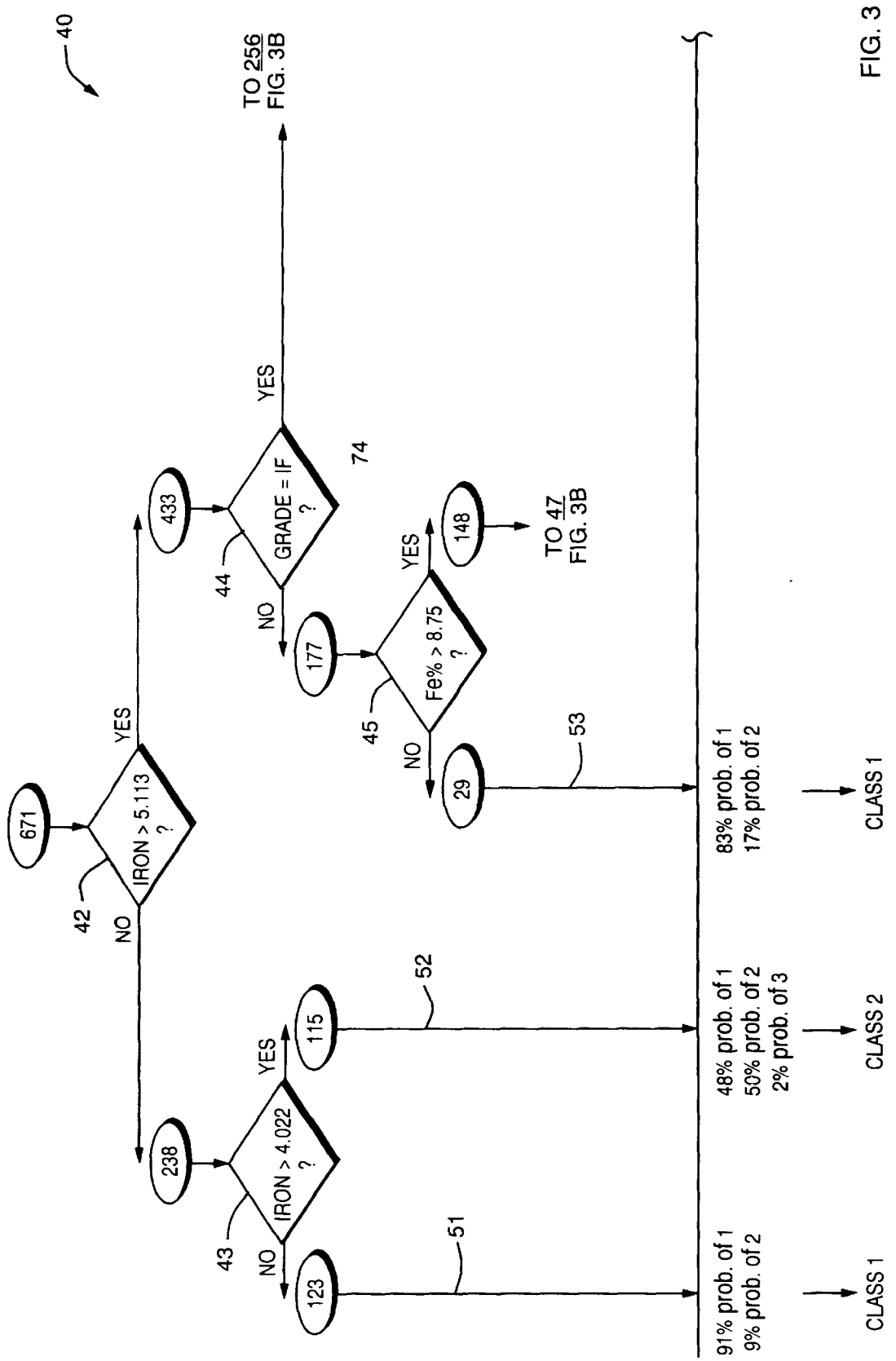
FIGS. 3 and 3A is a binary decision tree generated according to a second implementation of the present invention.
Figure 3A:
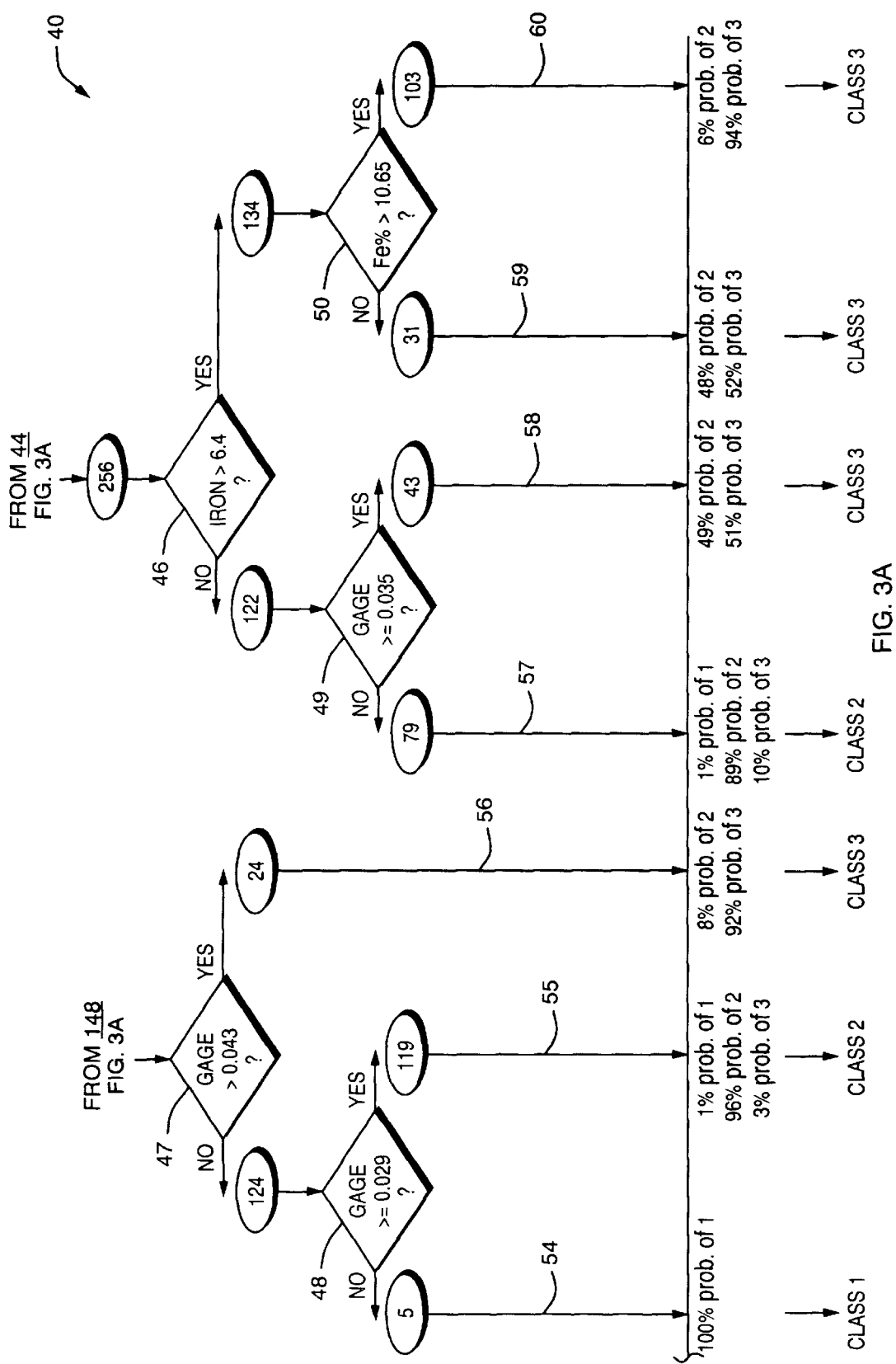

The V-bend tests which resulted in the binary decision tree 8 of FIG. 2A were conducted using the mass loss rating scheme. FIGS. 3–3A by contrast, shows a binary decision tree 40 which was developed by applying the method shown in FIG. 1 to test result data which was gathered using a powdering width rating scheme.

From a comparison of FIGS. 2A and 3–3A, it becomes readily apparent that differences between the two testing procedures cause the binary decision trees 8 and 40 to be significantly different. Thus, the test result data used to generate each binary decision tree 8 or 40 should be limited to that test result data which was gathered using the same test and the same rating scheme that the expected consumer will be using.

When the powdering width rating scheme was used, powdering to a width of 3.5 millimeters or less was deemed to constitute a "good" test result; powdering to a width between 3.5 millimeters and 5.67 millimeters was deemed to be a "marginal" test result; and powdering to a width greater than 5.67 millimeters was deemed to be a "poor" test result.

In FIGS. 3–3A, the binary decision tree 40 includes a total of nine (9) binary decisions 42–50. The binary decisions 42–50 are made on a total of four different product parameters, namely, iron content (in grams/meter$^2$), iron percentage (Fe %), gage, and grade (IF or non-IF). Ten (10) terminal branches 51–60 are present in the binary decision tree 40. Of the ten terminal branches 51–60, three terminal branches 51, 53 and 54 are class 1 terminal branches because of the high probabilities (91%, 83%, and 100%) that products in those branches will provide favorable responses to V-bend testing using the powdering width rating scheme. Product development efforts for consumers who execute V-bend testing using the powdering width rating scheme, therefore, should be directed to products which contain product parameters in the ranges dictated by the paths through terminal branches 51, 53 and 54, especially terminal branch 54.

If the optimum paths are eliminated from consideration by some other requirement of the consumer (e.g., the consumer requires an iron content greater than 5.113 grams/meter$^2$ and an IF grade), then product development efforts should be directed to products which contain product parameters in the ranges dictated by the path through terminal branch 57. At terminal branch 57, there is a one percent (1%) probability of achieving "good" test results, and also an eighty-nine percent (89%) probability of achieving "marginal" test results. Notably, the path through terminal branch 57 has only a ten percent (10%) chance of yielding "poor" test results. This compares to the 51%, 52%, and 94% probabilities of achieving "poor" test results when the product parameters fall within the other remaining terminal branches 58, 59, and 60, respectively. Thus, branch 57 provides a probability more favorable to satisfactory performance than the other available branches. Pursuing branch 57 is more likely to prove successful, although the other branches may ultimately prove able to develop at least a marginal product. That a product is marginal does not mean it is totally unacceptable, but may instead require more frequent inspection than is required for a good product.

Figure 3B:
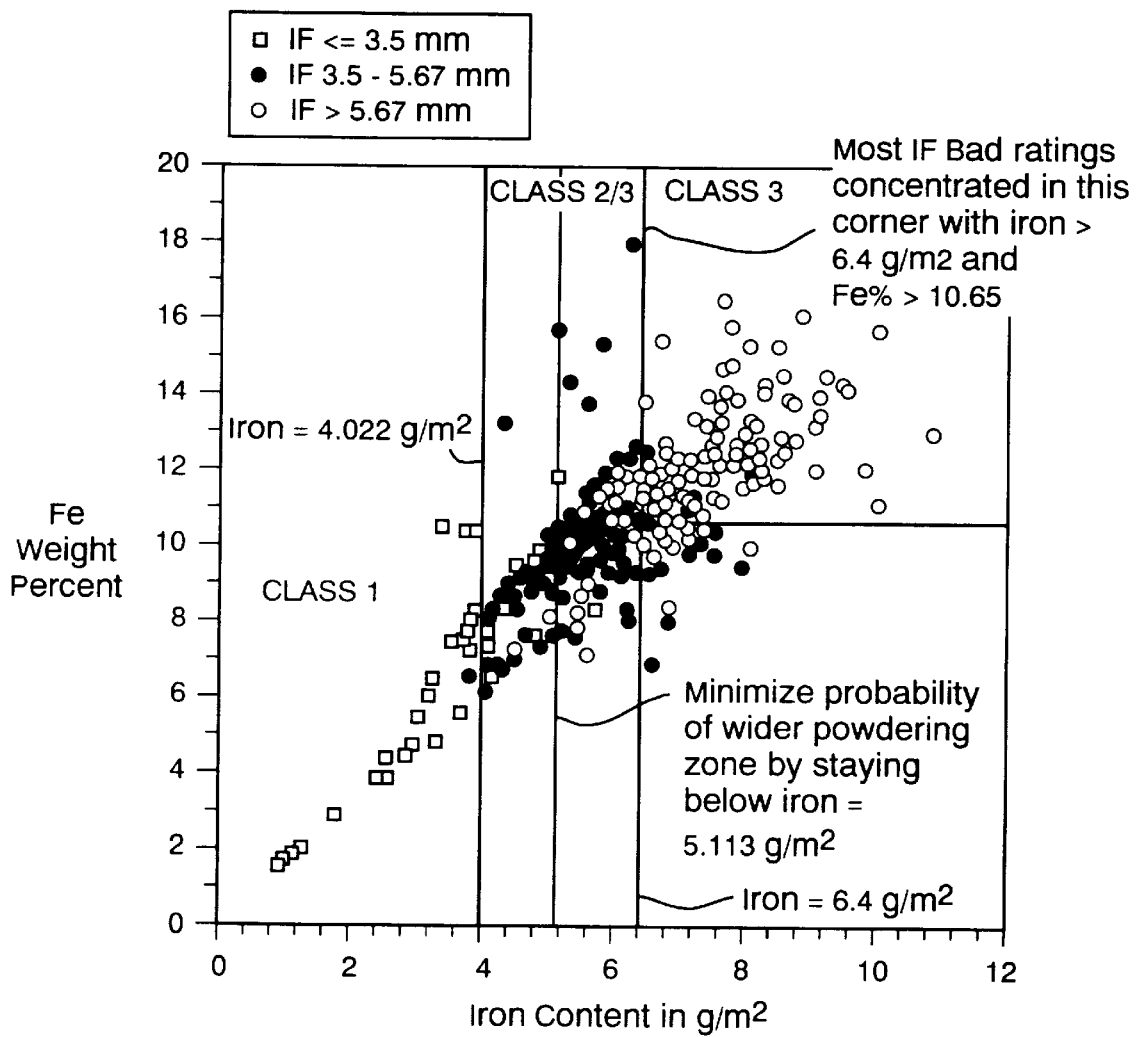
FIG. 3B is a graph of the test result data which was used in connection with the second implementation.

FIG. 3B is a graph of the test result data derived from the IF grade products only. In FIG. 3B, the test result data (powdering width in millimeter ranges) is plotted as a function of iron content (in grams/meter$^2$) and iron weight percent (Fe %). The "good", "marginal", and "poor" test results are represented by green, blue, and red circles, respectively. This graph visually demonstrates how well the binary decision tree 40 predicts whether the test result data of the IF grade products will be "good", "marginal", or "poor" based on the ranges of product parameter values which, according to the binary decision tree 40, place the samples into class 1, 2, or 3/2. Since the product's gage is not represented by either of the axes in the graph, there is some overlap between classes 2 and 3 in the middle of the graph.

Figure 3C:
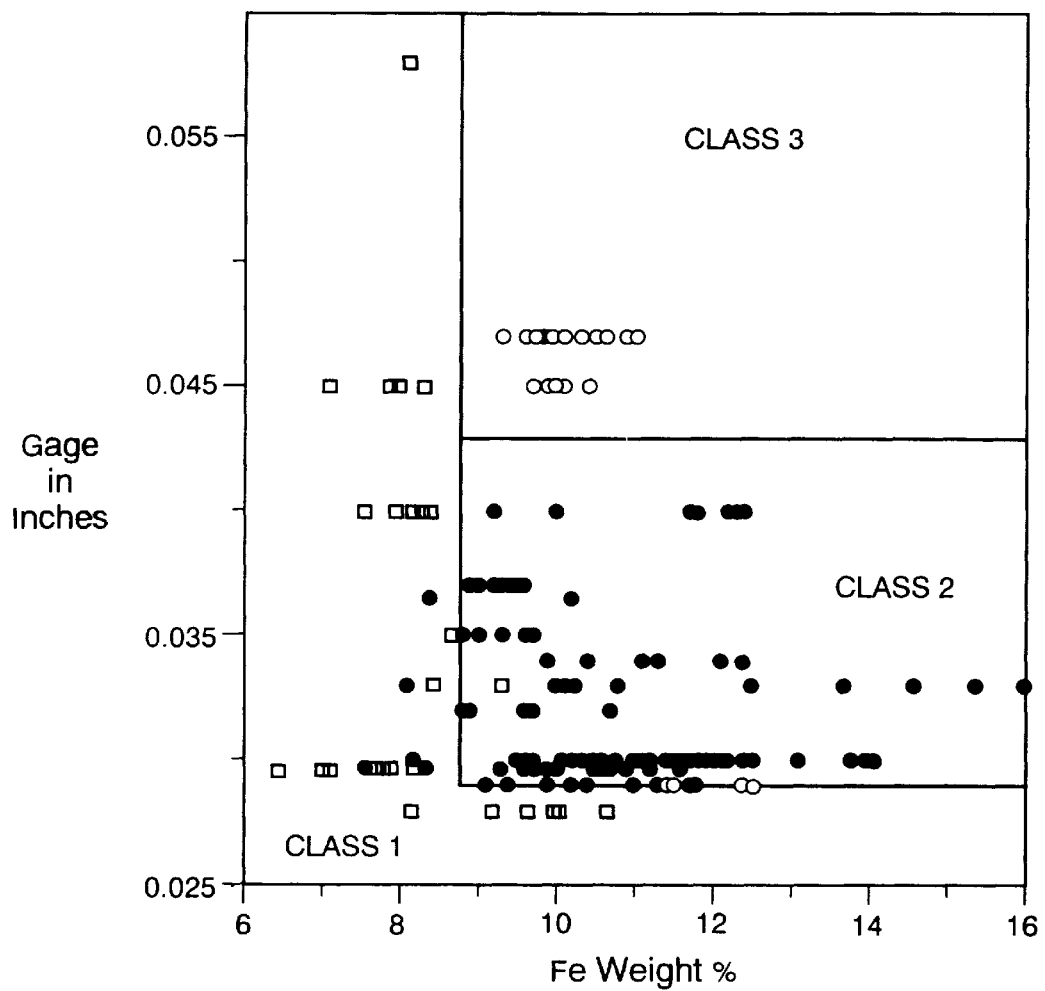
FIG. 3C is a graph of the test result data derived from the non-IF grade products with an iron content of more than 5.113 grams/meter$^2$, which was used in connection with the second implementation.

FIG. 3C is a graph of the test result data derived from the non-IF grade products with an iron content of more than 5.113 grams/meter$^2$. In FIG. 3C, the test result data (powdering width in millimeter ranges) is plotted as a function of iron weight percent (Fe %) and gage (in inches). The "good", "marginal", and "poor" test results are represented by green, blue, and red circles, respectively. This graph visually demonstrates how well the binary decision tree 40 predicts whether the test result data of the non-IF grade products will be "good", "marginal", or "poor" based on the ranges of product parameter values which, according to the binary decision tree 40, place the samples into class 1, 2, or 3.

Figure 3D:
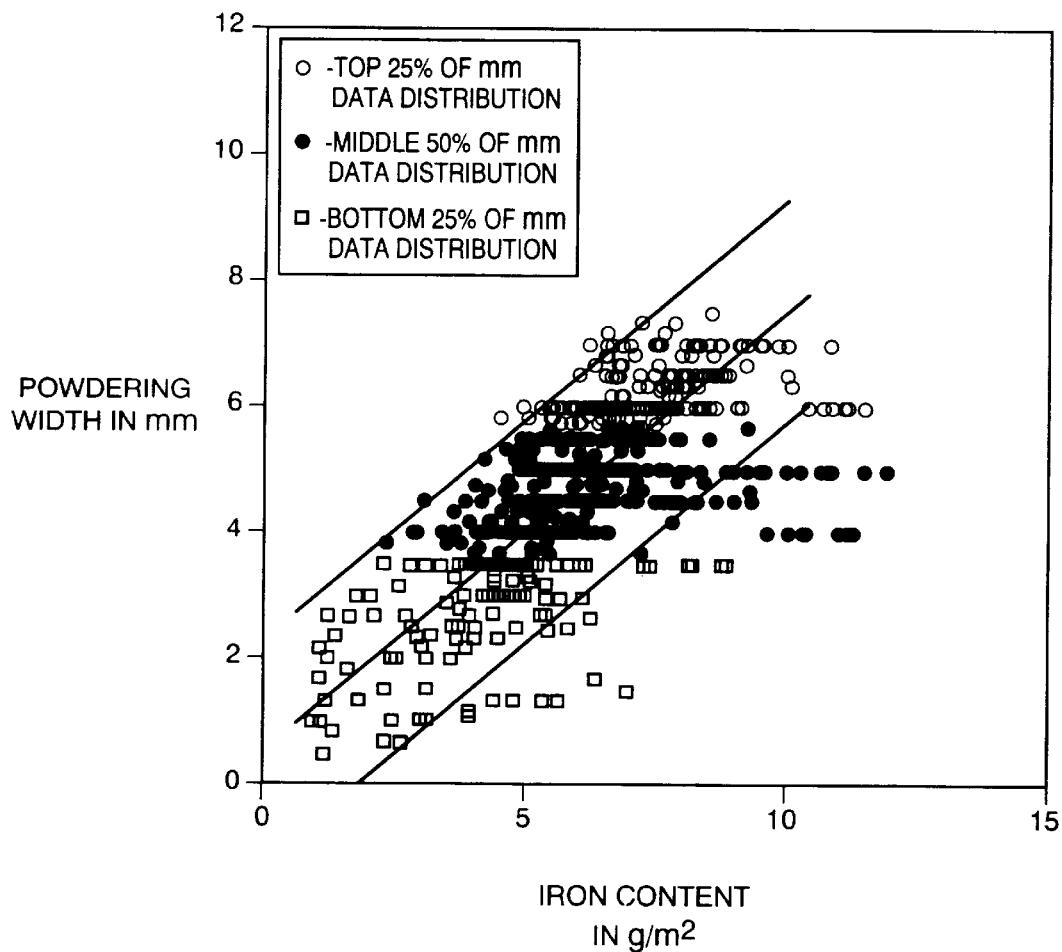
FIG. 3D is a graph showing a regression curve fitting generated by conducting a traditional regression analysis on the same test result data which was used in connection with FIGS. 3B and 3C.

For purposes of contrast, FIG. 3D is a graph showing a regression curve fitting generated by conducting a traditional regression analysis on the test result data which was used in connection with FIGS. 3B and 3C. FIG. 3D includes data from all grades and all gages of product. In FIG. 3D, the powdering width (in millimeters) is plotted as a function of iron content (in grams/meter$^2$). The solid lines in the graph represent the prediction bands for an average coating having a 61.24 grams/meter$^2$ coating weight, 9.28% iron weight percentage (Fe %), and a 0.0326 inch gage of steel. The bottom 25%, middle 50%, and top 25% of the test result data in the graph represent the test results which are classified as "good", "marginal", and "poor", respectively.

From a comparison of FIGS. 3B and 3C to FIG. 3D, it becomes readily apparent that the binary decision tree 40 more accurately predicts which ranges of product parameters will respond favorably to testing. The traditional analysis, by contrast, provides a predicted value for powdering width which is of little value since powdering width can vary significantly at any given iron content.

Analysis of 90-Bend Test Based on a Mass Loss Rating Scheme

Figure 4A:
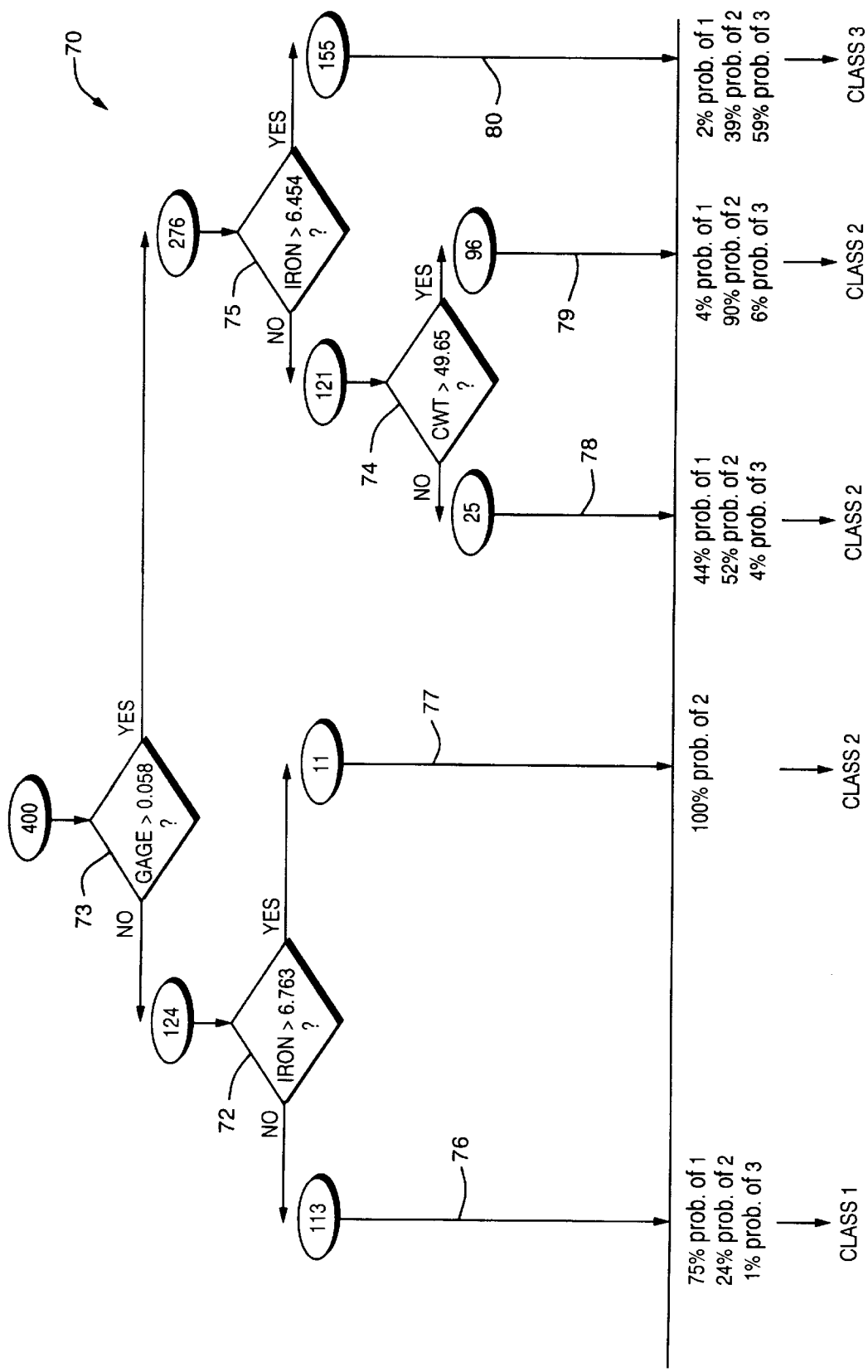
FIG. 4A is a binary decision tree which was generated based on a third implementation of the present invention.

FIG. 4A shows a binary decision tree 70 which was developed by applying the method shown in FIG. 1 to test result data on mass loss ratings taken from several iterations of a "90 bend" testing procedure. The method was applied in substantially the same way as it was applied in generating the binary decision tree 8 shown in FIG. 2A.

In applying the method shown in FIG. 1 to the mass loss ratings provided by a "90 bend" testing procedure, it was determined that mass losses of less than 5.3 milligrams constituted "good" test results; mass losses between 5.3 milligrams and 13.3 milligrams constituted "marginal" test results; and mass losses greater than 13.3 milligrams constituted "poor" test results.

In FIG. 4A, the binary decision tree 70 includes a total of four (4) binary decisions 72–75. The binary decisions 72–75 are made on a total of three different product parameters, namely, iron content (in grams/meter$^2$), gage, and coating weight (in grams/meter$^2$).

The first binary decision 73 in the binary decision tree 70 is made based on the gage of the steel. This was expected since strain increases with gage for a given tool radius.

Five (5) terminal branches 76–80 are present in the binary decision tree 70. The terminal branches 76–80 are categorized as class 1, class 2, or class 3 terminal branches based upon which probability is the highest among the probabilities of achieving "good", "marginal", and "poor" test results, respectively, for that particular terminal branch.

Of the five terminal branches 76–80, only terminal branch 76 is a class 1 terminal branch because of the high probability (75%) that products in that terminal branch 76 will provide favorable ("good") responses to 90-bend testing using the mass loss rating scheme. Product development efforts for consumers who execute 90-bend testing using the mass loss rating scheme, therefore, should be directed to products which contain product parameters in the ranges (i.e., iron content not greater than 6.763 grams/meter$^2$ and gauge no greater than 0.058) dictated by the path through terminal branch 76.

If the consumer's requirements preclude the use of product parameters having values in those ranges, then ranges corresponding to an alternative path through the terminal branch with the next best probabilities and which is consistent with the consumer's requirements is where product development efforts will be directed.

When a consumer requires a product with, for example, a heavy gage (e.g., a gage greater than 0.058), the product will, at best, qualify as a class 2 product under the mass loss testing scheme in a 90-bend test. This is so because terminal branches 78, 79, and 80 are class 2, class 2, and class 3 terminal branches, respectively. The class 2 designation, however, will not apply to the heavy gage products unless the iron content is less than or equal to 6.454 grams/meter$^2$. The class 2 designation means that those particular heavy gage products exhibit a higher probability of achieving marginal test results (i.e., a mass loss between 5.3 milligrams and 13.3 milligrams) than they do of achieving "good" or "poor" test results.

If, however, the iron content of a heavy gage product exceeds 6.454 grams/meter$^2$, there is almost a 60% probability that the mass loss will exceed 13.3 milligrams in a 90-bend test.

Figure 4B:
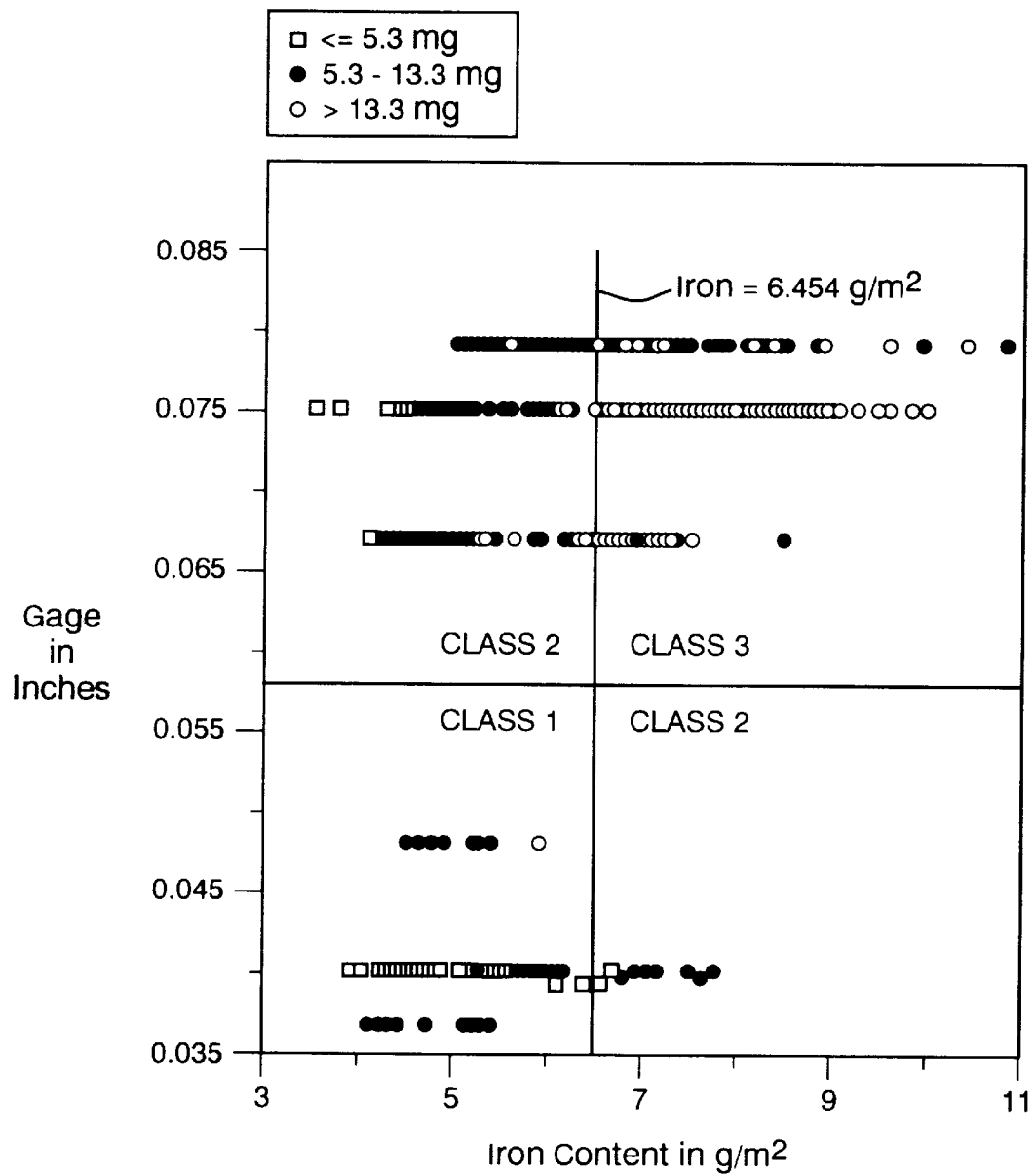
FIG. 4B is a graph of the test result data (powdering in milligrams) plotted as a function of iron content (in grams/meter$^2$) and gage (in inches), according to the third implementation.

FIG. 4B is a graph of the test result data (powdering in milligrams) plotted as a function of iron content (in grams/meter$^2$) and gage (in inches). This graph visually demonstrates how well the binary decision tree 70 predicts whether the test result data will be "good", "marginal", or "poor" based on the ranges of product parameter values which, according to the binary decision tree 70, place the products into class 1, 2, or 3.

Figure 4C:
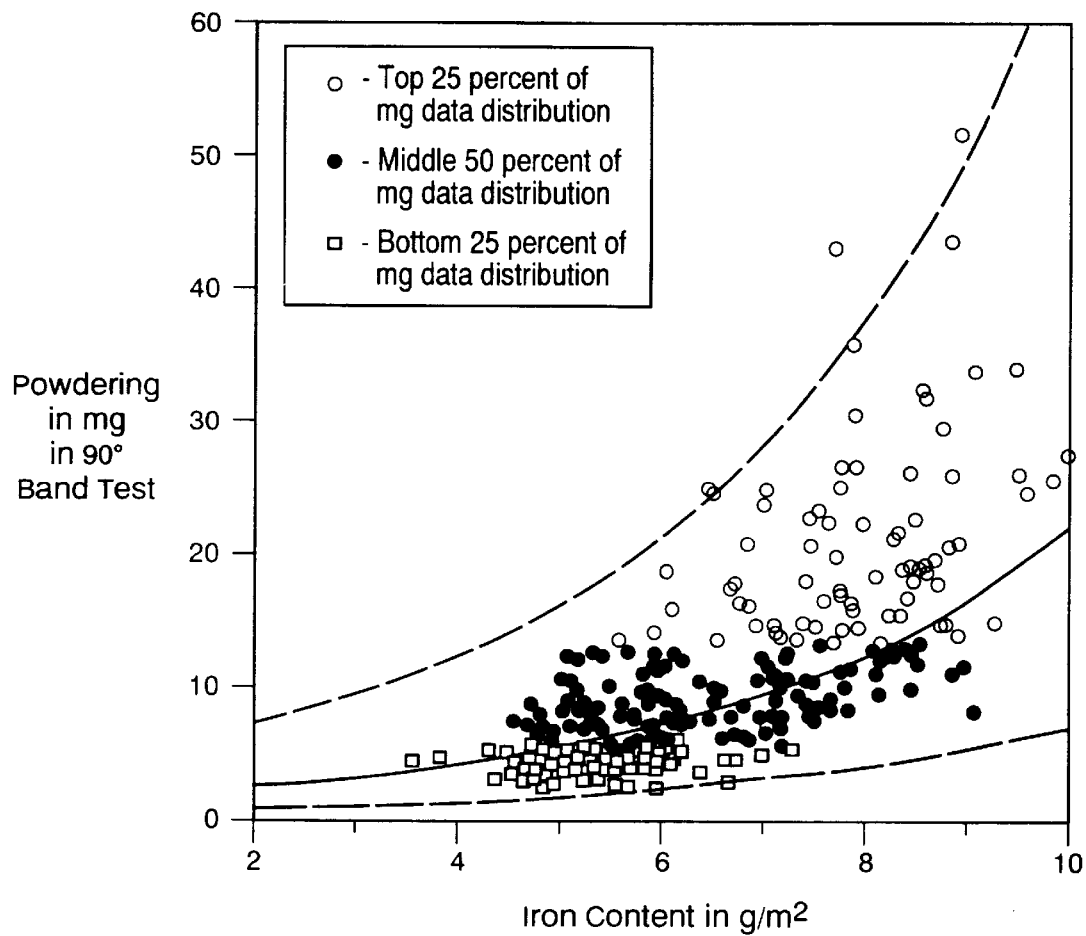
FIG. 4C is a graph showing a regression curve fitting generated by conducting a traditional regression analysis on the same test result data which was used in connection with FIG. 4B.

For purposes of contrast, FIG. 4C is a graph showing a regression curve fitting generated by conducting a traditional regression analysis on the same test result data which was used in connection with FIG. 4B. FIG. 4C includes data from all grades and all gages of product. In FIG. 4C, the powdering mass loss (in milligrams) is plotted as a function of iron content (in grams/meter$^2$). The broken lines in the graph represent the 95% prediction bands based on a regression fit to the test result data. The bottom 25%, middle 50%, and top 25% of the test result data in the graph represent the test results which are classified as "good", "marginal", and "poor", respectively.

From a comparison of FIG. 4B to FIG. 4C, it becomes readily apparent that the binary decision tree 70 more accurately predicts which ranges of product parameters will respond favorably to testing. The traditional analysis, by contrast, provides a predicted value for powdering width which is of little value since powdering width can vary significantly at any given iron content.

In the test result data from the 90 bend tests, information on coating microstructure was available and was included in the classification and regression tree analysis. It was difficult, however, to establish direct relationships between coating microstructure (as characterized by Zn—Fe intermetallic phase distributions determined in optical metallography), and powdering test results in the 90 bend tests. This was true for both the mass loss scheme described herein and the visual rating scheme which will be described hereinafter. While the reasons for this are not clear, it is possible that, since commercial galvanneal coatings are mostly made up of delta phase (which exists over a range of iron weight percents (Fe %)), the critical variable is the iron content within the delta phase. This may explain why the chemistry is identified by the classification and regression tree analysis as having the most significant effect on the powdering response.

Analysis of 90-Bend Test Based on a Visual Rating Scheme

Figure 5A:
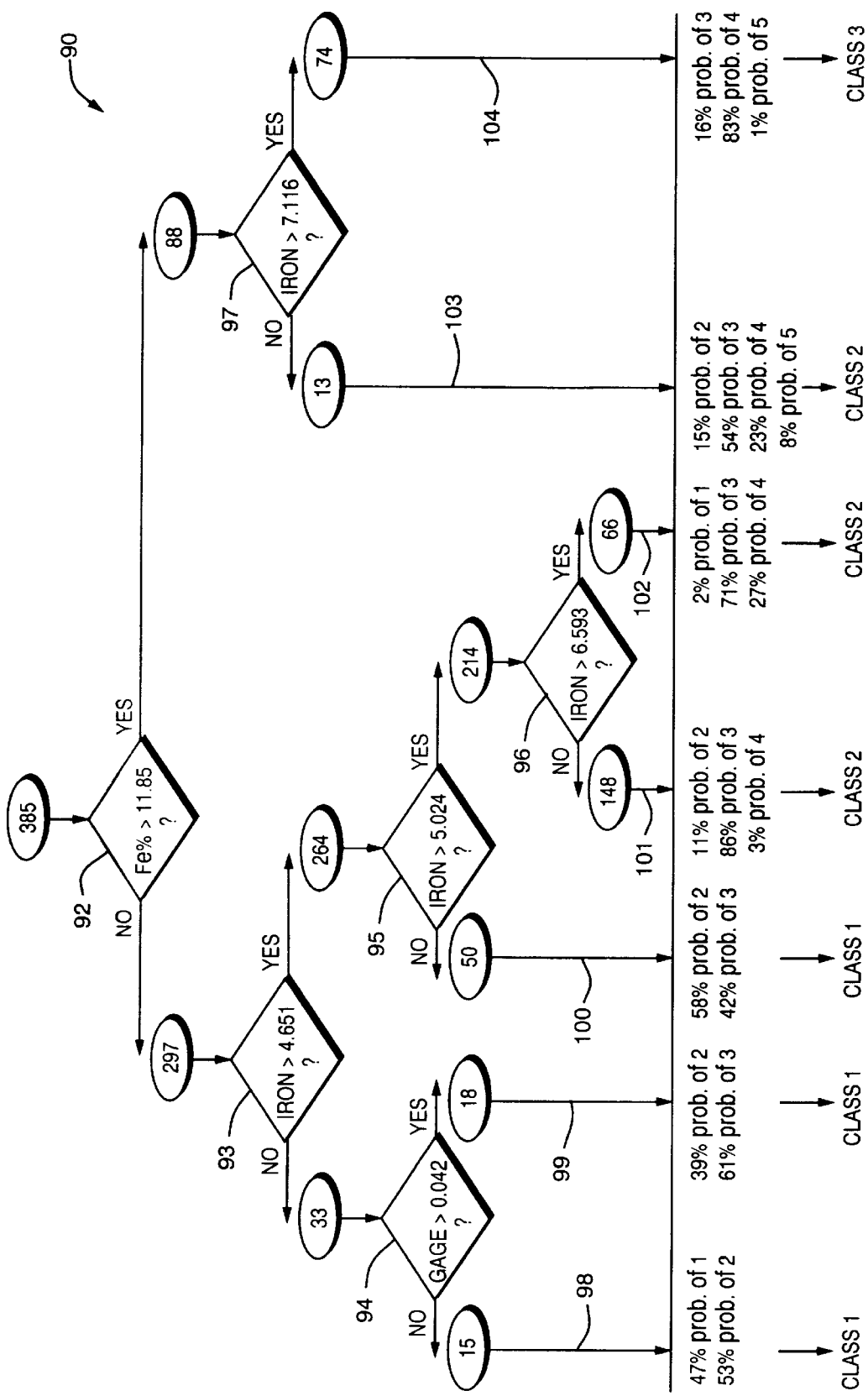
FIG. 5A is a binary decision tree which was generated according to a fourth implementation of the present invention.

FIG. 5A shows a binary decision tree 90 which was developed by applying the method shown in FIG. 1 to test result data on visual ratings taken from several iterations of a "90 bend" testing procedure. The method was applied in substantially the same way as it was applied in generating the binary decision tree 8 shown in FIG. 2A.

According to the visual rating scheme in a "90 bend" test, a scale of 1 to 5 is used, 1 being good and 5 being bad. A rating of 3 or less is typically acceptable. A rating of 4, however, is sometimes tolerated in products with heavier gages (e.g., about 0.07 inch) because those products tend to produce a rating of 4.

In applying the method shown in FIG. 1 to the visual ratings provided by a "90 bend" testing procedure, it was determined that a class 1 terminal branch is one which exhibits a negligible probability of obtaining a visual rating as high as 4. A class 2 terminal branch, by contrast, exhibits some probability of achieving a rating of 4 or 5. A class 3 terminal branch exhibits a high probabilty of achieving a rating greater than or equal to 4.

In FIG. 5A, the binary decision tree 90 includes a total of six (6) binary decisions 92–97. The binary decisions 92–97 are made on a total of three different product parameters, namely, iron content (in grams/meter$^2$), gage, and iron percentage (Fe %). Seven (7) terminal branches 98–104 are present in the binary decision tree 90. Of the seven terminal branches 98–104, only three terminal branches 98, 99, and 100 are class 1 terminal branches. Product development efforts for consumers who execute 90-bend testing using the visual rating scheme, therefore, should be directed to products which contain product parameters in the ranges dictated by the paths through terminal branches 98, 99, and 100, especially terminal branch 98. In this regard, such product development efforts should be directed to products having an iron weight percentage (Fe %) below 11.85% and an iron content below 5.024 grams/meter$^2$. Surprisingly, the classification and regression tree analysis did not consider gage to be a product parameter which has the most significant effect on powdering response. This is noticeably different from the results obtained when a mass loss rating scheme is used in conducting the 90 Bend test.

If the consumer's requirements preclude the use of product parameters having values in the ranges dictated by the paths through terminal branches 98, 99, and 100, then ranges corresponding to an alternative path through the terminal branch with the next best probabilities and which is consistent with the consumer's requirements, is where product development efforts will be directed. In this regard, even if the iron content exceeds 5.024 grams/meter$^2$ but remains below 6.593 grams/meter$^2$, there is a 97% probability of obtaining an acceptable rating of 2 or 3.

If, however, the iron weight percent (Fe %) exceeds 11.85% and the iron content exceeds 7.116 grams/meter$^2$, then the probability of obtaining a rating of 4 is very high, and there is a negligible probability of obtaining a rating of 1 or 2.

Figure 5B:
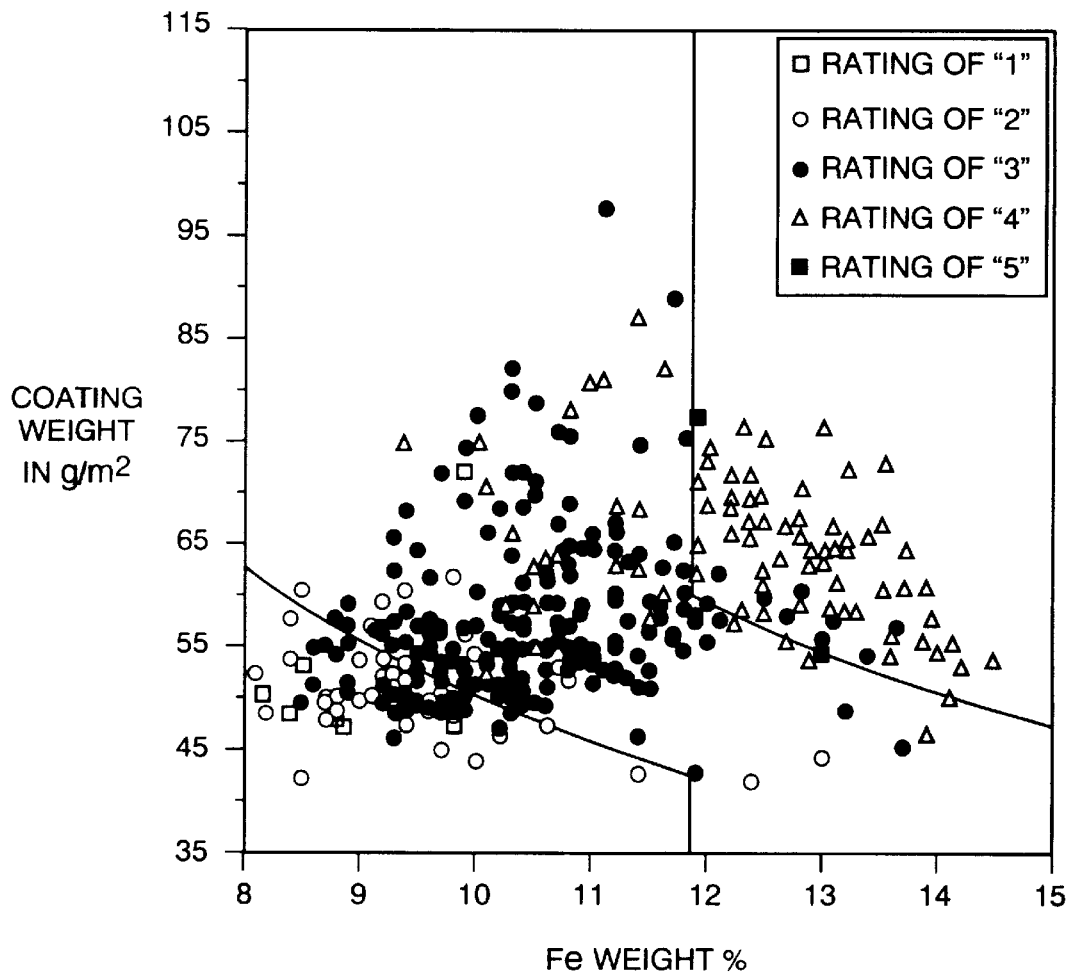
FIG. 5B is a graph of the test result data (powdering in milligrams) plotted as a function of coating weight (in grams/meter$^2$) and iron weight percentage (Fe %), according to the fourth implementation.

FIG. 5B is a graph of the test result data (powdering in milligrams) plotted as a function of coating weight (in grams/meter$^2$) and iron weight percentage (Fe %). This graph visually demonstrates how well the binary decision tree 90 predicts whether the test result data will be "good", "marginal", or "poor" based on the ranges of product parameter values which, according to the binary decision tree 90, place the products into class 1, 2, or 3.

Figure 5C:
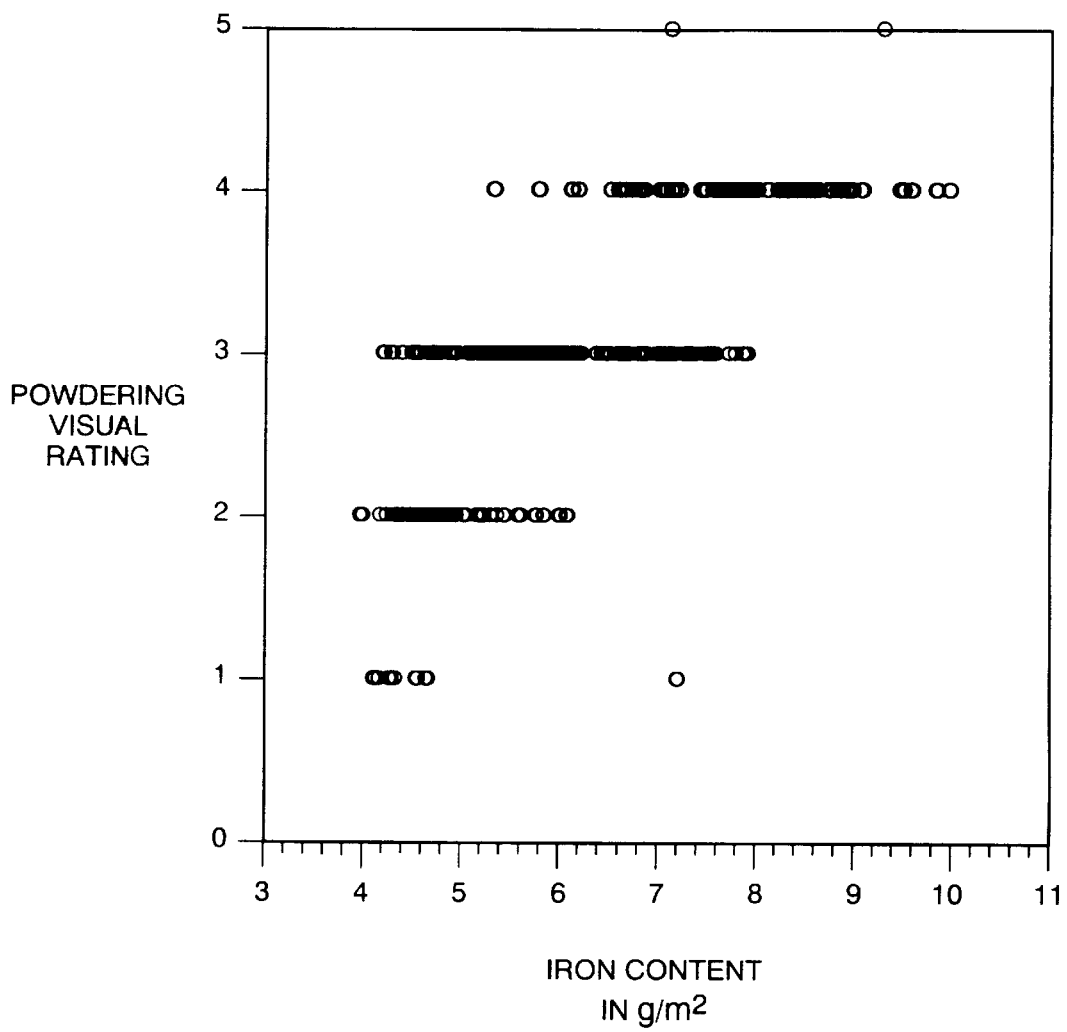
FIG. 5C is a graph showing data on visual ratings for all grades and gages plotted as a function of the iron content in the coatings, according to the fourth implementation.

For purposes of contrast, FIG. 5C is a graph showing data on visual ratings for all grades and gages plotted as a function of the iron content in the coatings. The data suggests that the visual ratings increase with iron content in the coating. Since the visual rating is already classified from 1 to 5, no other classification method was used, nor were there any regression lines generated based on this data.

From a comparison of FIG. 5B to FIG. 5C, it becomes readily apparent that the binary decision tree 90 more accurately predicts which ranges of product parameters will respond favorably to testing.

Analysis of Reverse Olsen Test Based on a Chrysler Mass Loss Rating Scheme

Figure 6A:
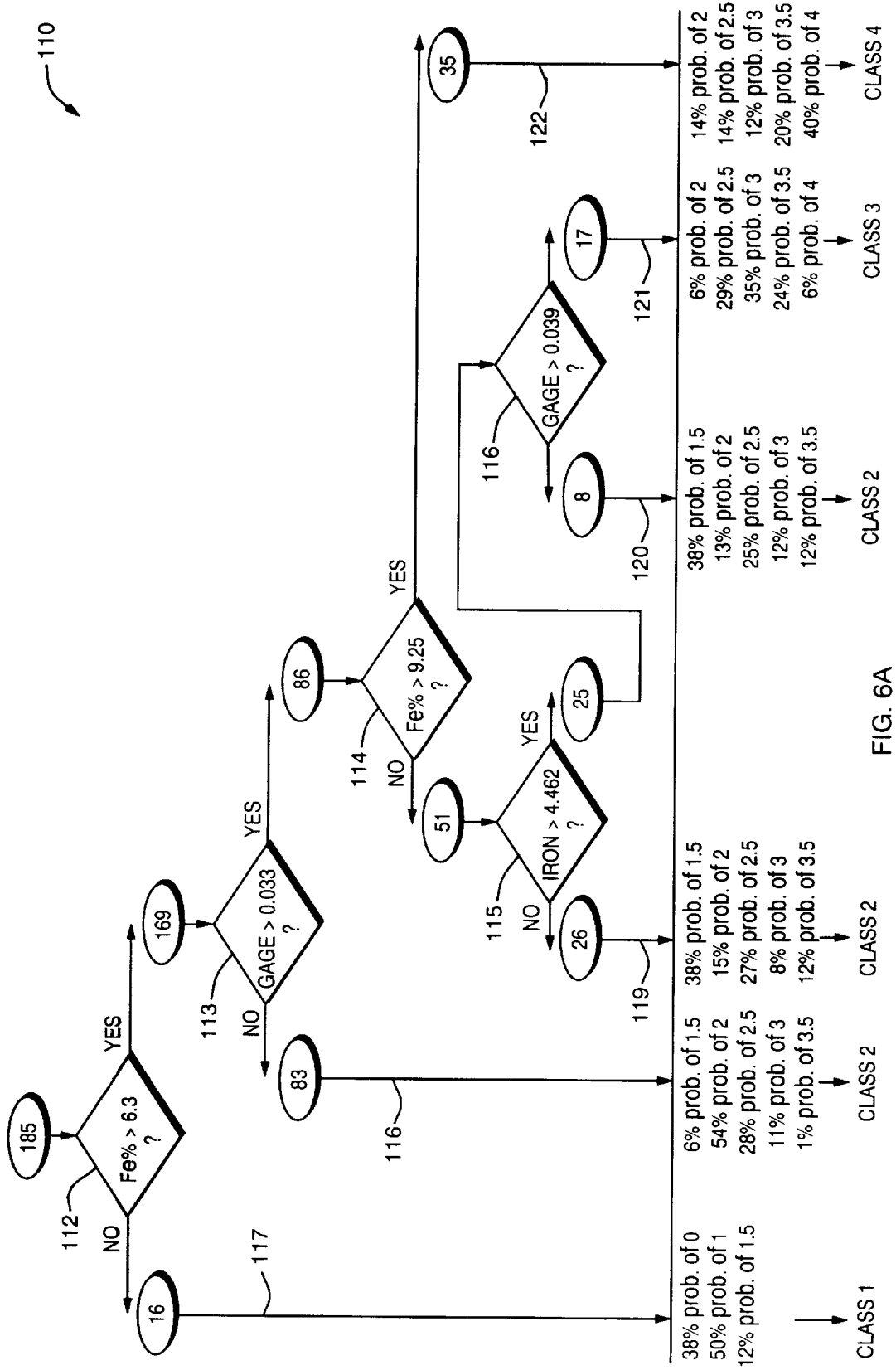
FIG. 6A is a binary decision tree which was generated according to a fifth implementation of the present invention.

FIG. 6A shows a binary decision tree 110 which was developed by applying the method shown in FIG. 1 to test result data on Chrysler mass loss ratings taken from several iterations of a reverse Olsen testing procedure. Mass loss measurements were originally implemented in reverse Olsen tests for the purpose of eliminating the lack of precision associated with the traditional approach of taking visual ratings. The mass losses are converted to Chrysler ratings based on a Chrysler specification ("Double Olsen Coating Adhesion Test", Chrysler Motors Corporation, Vehicle Engineering Office, Specification #LP-461H-120). According to information from Chrysler, the relationship between the Chrysler rating and mass loss was developed by initially selecting samples with different visual ratings and measuring the mass losses on those product samples. A Chrysler rating of 3.5 or less is acceptable to Chrysler.

The method shown in FIG. 1 was applied in substantially the same way as it was applied in generating the binary decision tree 8 shown in FIG. 2A, except that the test result data was classified into four (4) different classes, as opposed to three (3). In applying the method shown in FIG. 1 to the Chrysler mass loss ratings provided by a reverse Olsen testing procedure, it was determined that class 1 contains products having a Chrysler rating equal to or less than 1.5. Class 2 contains products which have a Chrysler rating between 1.5 and 3.5. In class 3, there is some probability that the products will have a Chrysler rating of 4. In class 4, there is a high probability that products having the indicated ranges of product parameters will have a Chrysler rating of 4.

When using this classification technique, the test results which fall within class 3, and especially class 4, are generally undesirable because each of these classes is associated with a chance of obtaining a product with a Chrysler rating of 4.

In FIG. 6A, the binary decision tree 110 includes a total of five (5) binary decisions 112–116. The binary decisions 112–116 are made on a total of three different product parameters, namely, iron content (in grams/meter$^2$), gage, and iron percentage (Fe %). Six (6) terminal branches 117–122 are present in the binary decision tree 110. Of the six terminal branches 117–122, only one term branch 117, however, requires that the iron weight percentage (Fe %) be less than 6.3%, as dictated by the binary decision 112. An iron weight percentage (Fe %) lower than 6.3%, however, is not practical for commercial galvanneal coatings because it may cause incomplete alloying of the coating(s).

Product development efforts for consumers who execute reverse Olsen tests using a Chrysler mass loss rating scheme, therefore, should be directed, not to products which contain product parameters in the range (Fe % less than 6.3%) dictated by the path through terminal branch 117, but rather to products which contain parameters in the range(s) dictated by an alternative path through the terminal branch 118, 119, 120, 121, or 122 with the next best probabilities and which also is consistent with the consumer's requirements.

In this regard, the path through terminal branch 118 indicates that products with an iron weight percentage (Fe %) greater than 6.3% and with a gage equal to or less than 0.033 inch, exhibit a strong probability of obtaining a rating below 3.5. This is so at least for samples having iron weight percentages (Fe %) up to 12% and coating weights up to 64 grams/meter$^2$ which, according to the above table of product data and test result data, correspond to the tested ranges.

Product development efforts, therefore, should be directed to products having an iron weight percentage (Fe %) greater than 6.3% and a gage equal to or less than 0.033 inch, so long as those parameters are consistent with the specifications supplied by the consumer. If they are not consistent with the consumer's specification, then an alternative path which is consistent and which terminates in the next best probabilities, will be used to determine the ranges of product parameter values where product development efforts will be directed.

For gages heavier than 0.033 inch, the chances of obtaining a rating of 4 increases if the iron weight percentage (Fe %) exceeds 9.25%. For iron weight percentages below 9.25%, the chances of obtaining a rating of 4 exists if the gage exceeds 0.039 inch.

Based upon the classification and regression tree analysis, for a galveanneal coating with a 9% iron weight percentage (Fe %) and 0.035 inch gage, a rating of 4 is not expected. This represents a significant improvement over the traditional regression analysis of data.

Figure 6B:
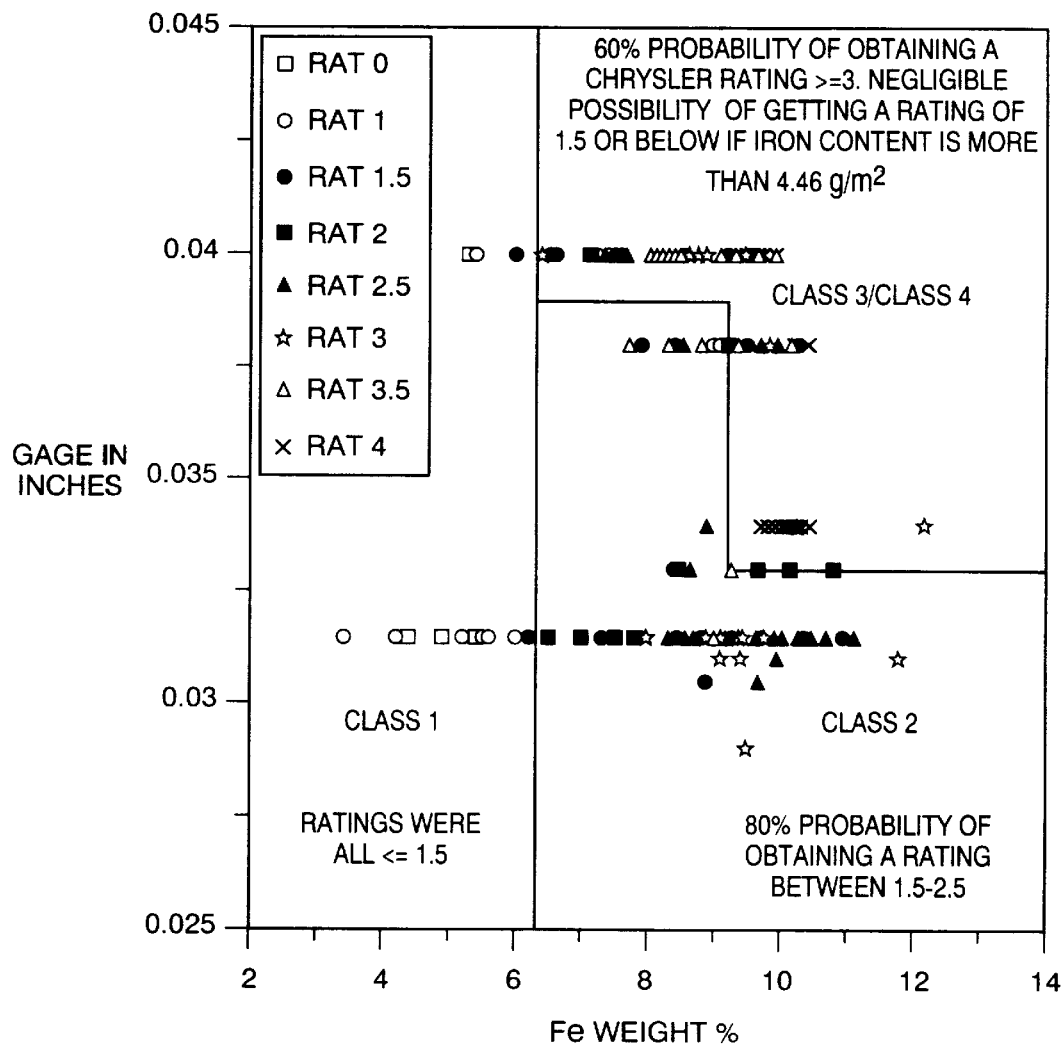
FIG. 6B is a graph of the test result data (powdering represented by the Chrysler rating) plotted as a function of iron weight percentage (Fe %) and gage (in inches), according to the fifth implementation.

FIG. 6B is a graph of the test result data (powdering represented by the Chrysler rating) plotted as a function of iron weight percentage (Fe %) and gage (in inches). This graph visually demonstrates how well the binary decision tree 110 predicts whether the test result data will have a Chrysler rating of 0 to 1.5, 1.5 to 2.5, or 3 to 4 based on the ranges of product parameter values which, according to the binary decision tree 110, place the products into class 1,2, 3, or 4.

Figure 6C:
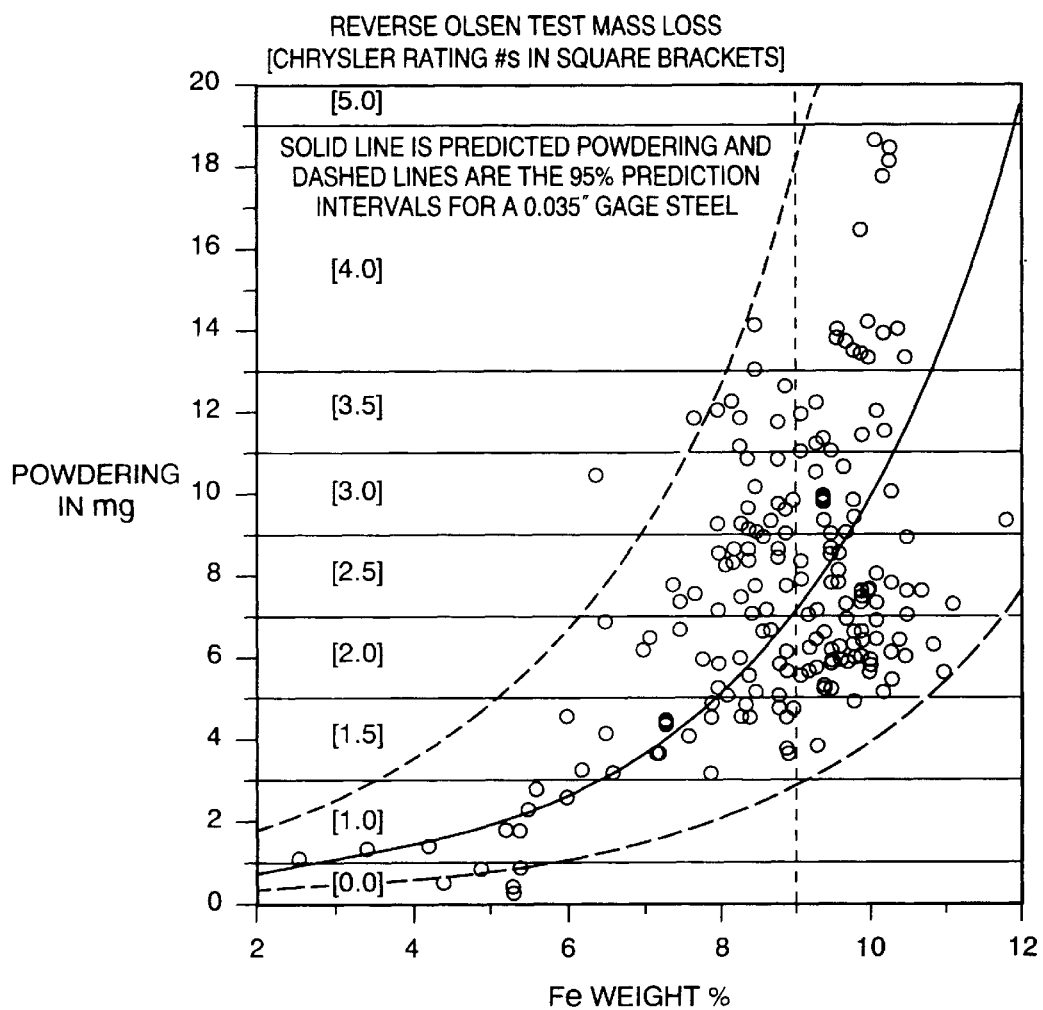
FIG. 6C is a graph showing a regression curve fitting generated by conducting a traditional regression analysis on the test result data which was used in connection with FIG. 6B.

For purposes of contrast, FIG. 6C is a graph showing a regression curve fitting generated by conducting a traditional regression analysis on the same test result data which was used in connection with FIG. 6B. FIG. 6C includes data from all grades and all gages of product. In FIG. 6C, the powdering mass loss (in milligrams and Chrysler rating) is plotted as a function of iron weight percent (Fe %). The broken lines in the graph represent the 95% prediction bands based on a regression fit to the test result data. It is clear from FIG. 6C that, at any given iron weight percentage (Fe %), the range in predicted powdering based on standard regression is large. At an iron weight percentage (Fe %) of 9%, for example, expected ratings can range anywhere between 1.5 and 4 for a 0.035 inch gage galvanneal-coated sheet of steel.

From a comparison of FIG. 6B to FIG. 6C, it becomes readily apparent that the binary decision tree 110 more accurately predicts which ranges of product parameters will respond favorably to testing. This accuracy is particularly impressive in view of the significantly smaller collection of product data and test result data upon which the classification and regression tree analysis was based. As more data becomes available, variations in that data may affect the binary decision tree 110.

Figure 6D:
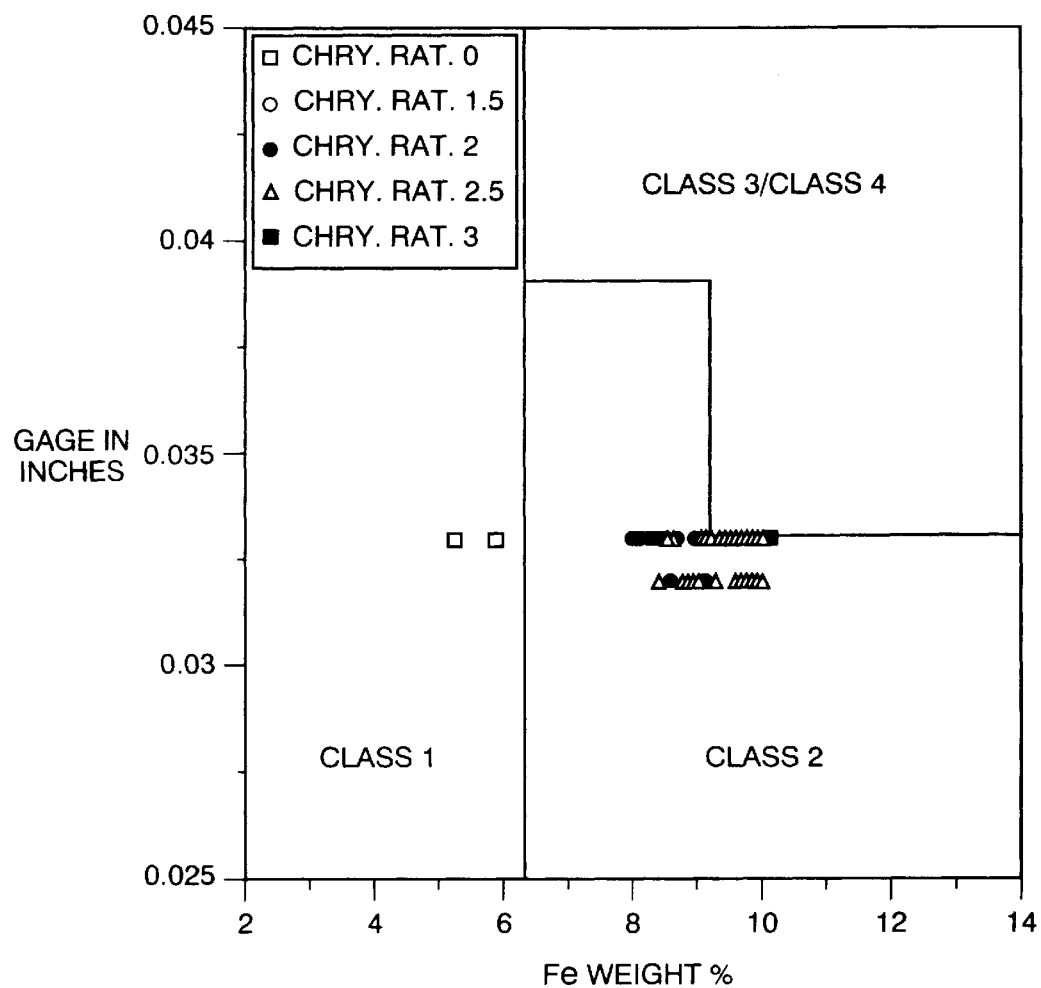
FIG. 6D is a graph of some recently acquired Chrysler ratings of galvanneal-coated steel manufactured at Bethlehem Steel Corporation's Burns Harbor facility, according to the fifth implementation.

As a further example of the accuracy of the binary decision tree 110, FIG. 6D is a graph of Chrysler ratings of galvanneal-coated steel manufactured at Bethlehem Steel Corporation's Burns Harbor facility. The subject galvanneal-coated steel is grade A 111, and its product parameter values were not used during generation of the binary decision tree 110. Nevertheless, the Chrysler ratings as a function of iron weight percentage (Fe %) and gage (in inches) are accurately predicted by the binary decision tree 110.

Analysis of Reverse Olsen Test Based on a Chrysler Visual Rating Scheme

Figure 7A:
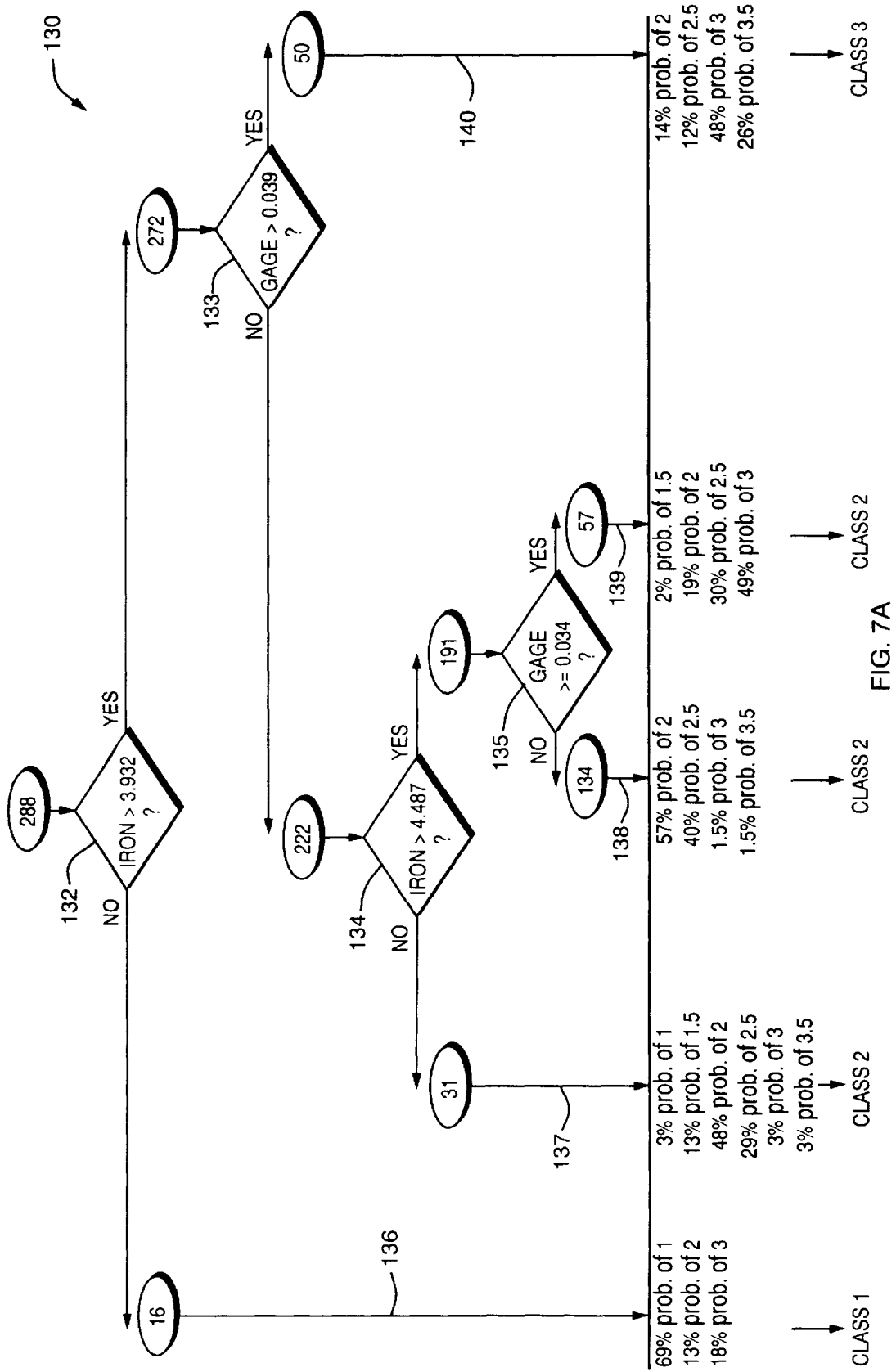
FIG. 7A is a binary decision tree which was generated according to a sixth implementation of the present invention.

FIG. 7A shows a binary decision tree 130 which was developed by applying the method shown in FIG. 1 to test result data on Chrysler visual ratings taken from several iterations of a reverse Olsen testing procedure.

The method shown in FIG. 1 was applied in substantially the same way as it was applied in generating the binary decision tree 110 shown in FIG. 7A.

In FIG. 7A, the binary decision tree 130 includes a total of four (4) binary decisions 132–135. The binary decisions 132–135 are made on two different product parameters, namely, iron content (in grams/meter$^2$) and gage. Five (5) terminal branches 136–140 are present in the binary decision tree 130. Of the five terminal branches 136–140, only one terminal branch 136 is a class 1 terminal branch. Thus, for products with an iron content below 3.932 grams/meter$^2$, there is only a small probability (18%) of achieving a rating higher than 2.

Notably, gage again provides a strong influence on the powdering rating. For gages less than 0.034 inch, the probability of obtaining a rating less than or equal to 2.5 is high. In contrast, for gages greater than or equal to 0.034 inch but less than 0.039 inch, the probability of obtaining a rating greater than 2.5 is about 50%. When the gage exceeds 0.039 inch, the probability of obtaining a rating greater than 2.5 is about 75%. In the visual rating data set, there were no rating 4 products. Some of the rating 4 samples determined by the mass loss scheme must have been rated as 3.5 in visual observations. Furthermore, the 16 data points at low iron content (i.e., less than 3.392 grams/meter$^2$) correspond to the 16 data points at low Fe % in the mass loss binary decision tree 110. While there may be some discrepancies in rating obtained by mass loss versus visual observation, it appears that the general trends toward achieving good powdering results are similar in both schemes (as expected, since the underlying classification criteria is the same in both).

Galvannealed sheet steel samples with gage less than or equal to 0.033 inch can consistently exhibit good ratings in reverse Olsen tests, as long as other coating properties are within the data set range given in the above table for these tests. The sensitivity of the reverse Olsen test to gage is surprising considering the narrow range of gages available in the data set used for the classification and regression tree analysis.

Figure 7B:
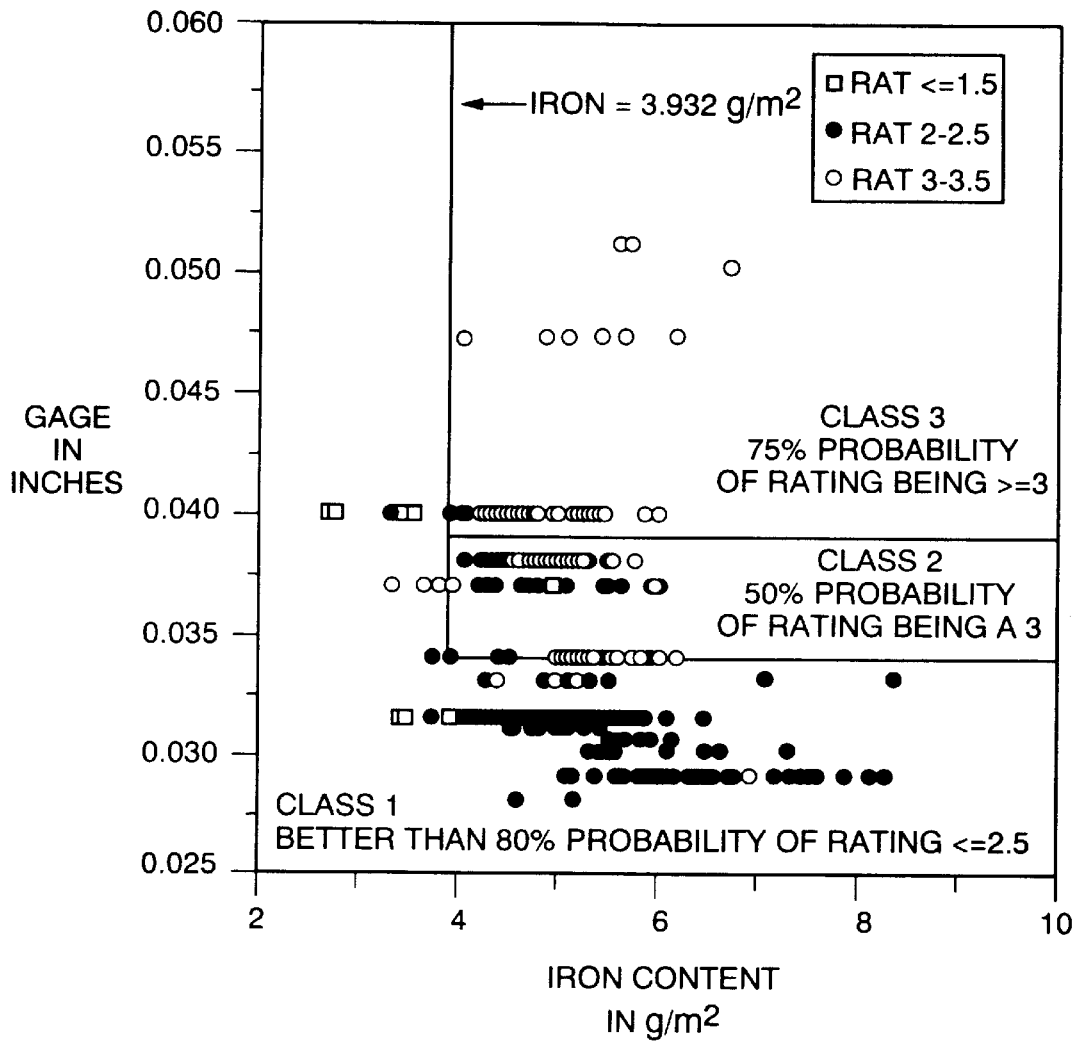
FIG. 7B is a graph of the data points and results of the classification and regression tree analysis on visual ratings in reverse Olsen tests, according to the sixth implementation.
Figure 7C:
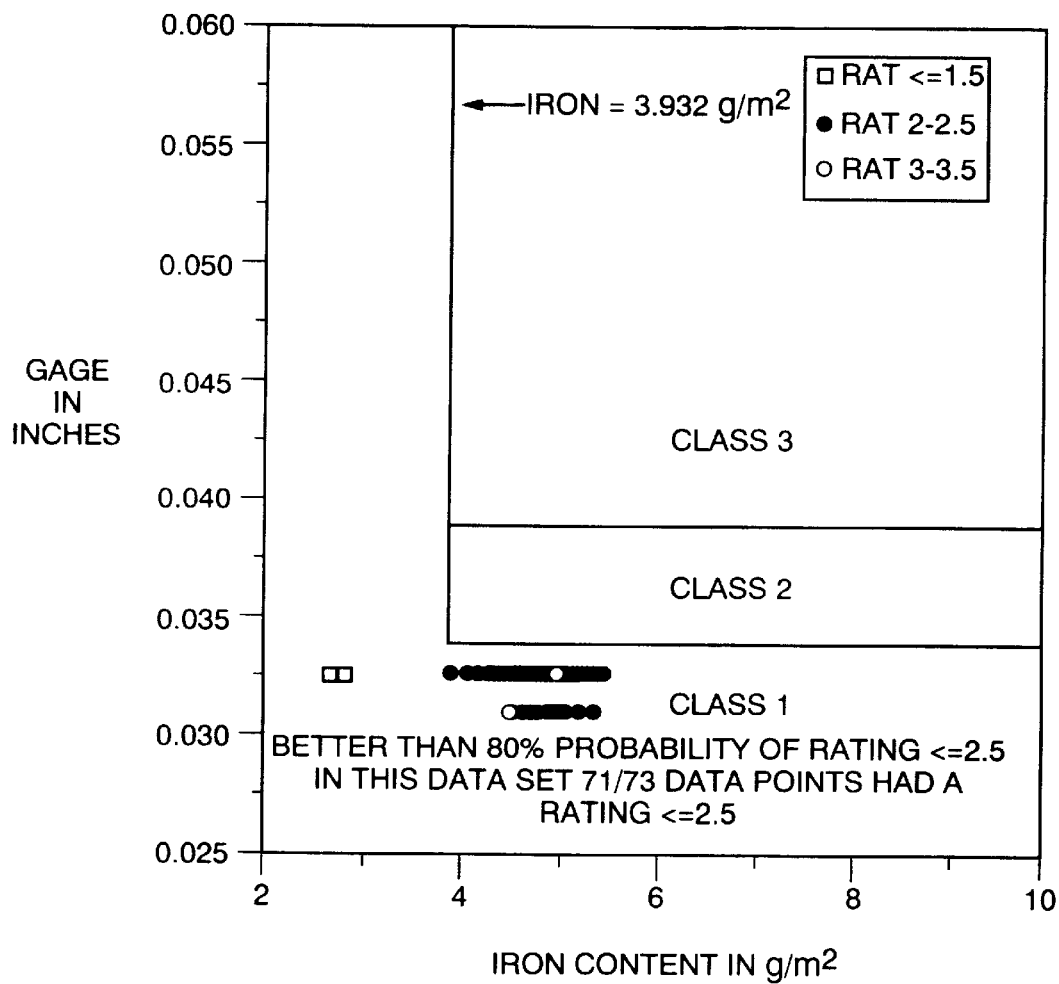
FIG. 7C is a graph of some recently acquired visual ratings in reverse Olsen tests, according to the sixth implementation.

The results of the classification and regression tree analysis on visual ratings in reverse Olsen tests are summarized in the graph of FIG. 7B, along with the data points. The effects of gage and iron content on visual ratings are clearly seen on a data set which otherwise would appear very scattered and without clear trends. FIG. 7C plots some recently acquired visual ratings in reverse Olsen tests onto a graph similar to that of FIG. 7B, which data was not used in generating the binary decision tree 130. The recently acquired data fits the graph classifications quite well and therefore supports the accuracy and effectiveness of the binary decision tree 130.

The following chart ranks the product parameters according to their respective effects on the powdering response, for each of the different tests, as determined by the classification and regression tree analyses:

| Test Method | Iron Content (coating weight x Fe %) | Fe % | Gage | Coating Weight | Grade | Galvanneal Phase Composition |
|---|---|---|---|---|---|---|
| 90-Bend Mass Loss | 1 | 3 | 2 | 4 | 5 | 6 |
| 90-Bend Visual Rating | 1 | 2 | 3 | 2 | 4 | 5 |
| V-Bend Mass Loss | 1 | 2 | 4 | 3 | 5 | Not Applicable |
| V-Bend Powdering Width | 2 | 1 | 4 | 3 | 4 | Not Applicable |
| Reverse Olsen Mass Loss | 1 | 1 | 2 | 3 | Not Clear | Not Applicable |
| Reverse Olsen Visual Rating | 1 | 2 | 3 | 4 | Not Clear | Not Applicable |
| Average ranking for all tests combined | 1.2 | 1.8 | 3 | 3.2 | Not Applicable | Not Applicable |

In order to implement the method of the present invention on one or a combination of the product development efforts described above, the present invention also provides a computer system for use in determining product parameters.

Computer System for Product Development

Figure 8:
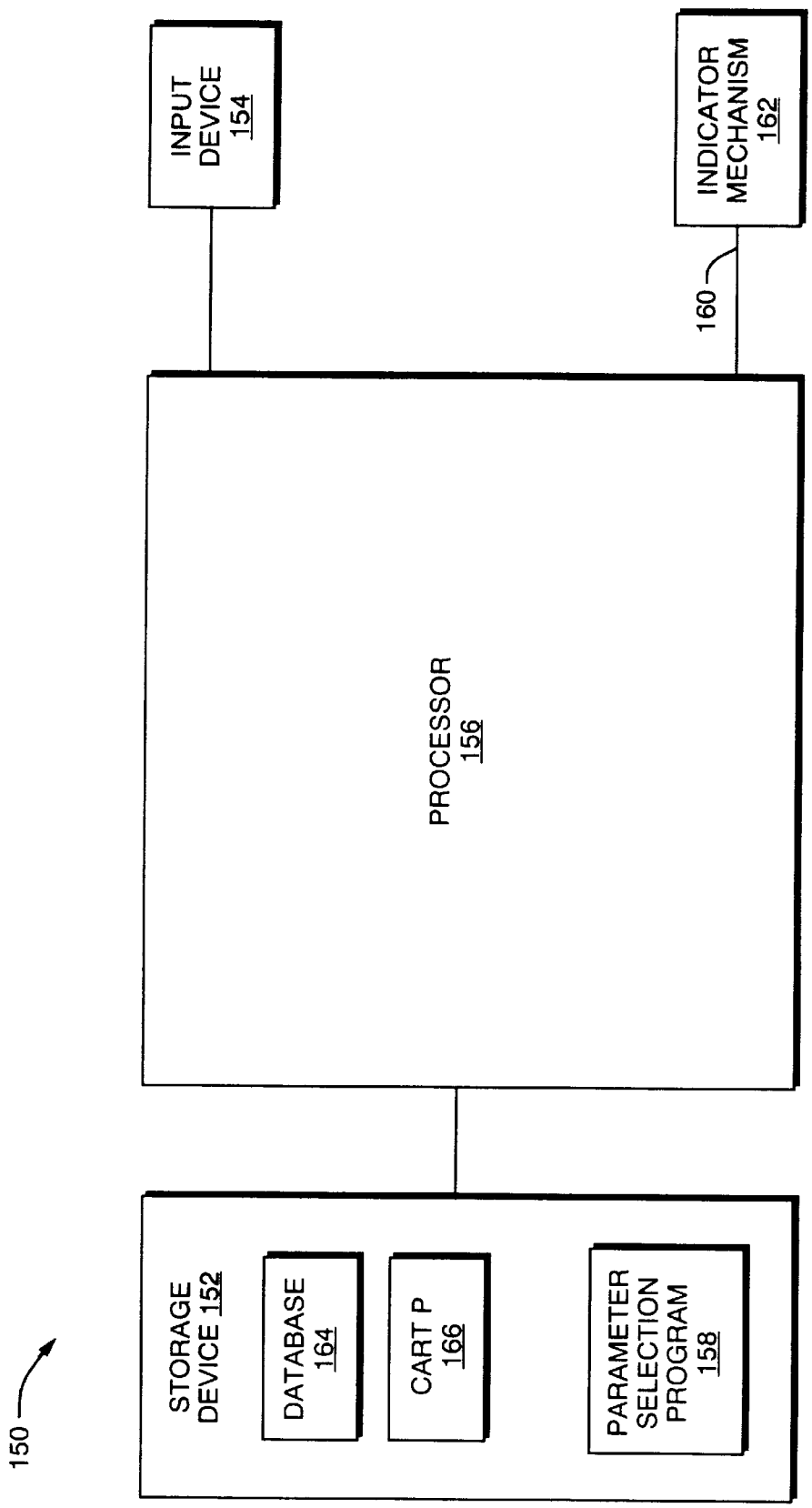
FIG. 8 is a block diagram of a computer system according to a preferred embodiment of the present invention.

FIG. 8 illustrates a preferred embodiment of the computer system 150. The computer system 150 comprises a storage device 152, an input device 154, and a processor 156. The storage device 152 contains a parameter selection program 158 based on at least one binary decision tree which, in turn, is derived from a classification and regression tree analysis of a) product data on previously manufactured products, and b) test data on how such previously manufactured products respond to at least one testing procedure. Preferably, the classification and regression tree analysis is the same or similar to that which is used in the method of FIG. 1.

The input device 154 receives information indicative of at least one desired value of product parameter (e.g., values specified by the consumer) and converts this information to a format which is detectable by the processor 156. The input device 154 may be implemented using a keypad, a keyboard, a digitizer, a touch pad, a magnetic or optical medium reader, a proximity-sensitive surface, or any other known input device.

The processor 156 is connected at least indirectly to the storage device 152 and to the input device 154. The processor 156 is adapted, through suitable programming or otherwise, to perform the parameter selection program 158 by applying the information obtained by the input device 154 to the binary decision tree. Based on this application of the information to the binary decision tree, the processor 156 generates an output signal 160 indicative of at least one range of at least one other product parameter which, according to the binary decision tree(s), contains values of the other product parameter(s) which enhance a probability that a product with the desired value(s) of product parameter will respond favorably to the testing procedure(s). The range(s) thus provided represent a good starting point for product development efforts.

In applying the information from the input device 154, the processor 156 preferably eliminates from consideration any decision result branches of binary decision tree(s) which are inconsistent with that information. The ranges which represent a good starting point thus are determined by the processor 156 based on which path through the decision result branches which were not eliminated from consideration, terminates in the best probability that a product with the desired value of product parameter will respond favorably to the testing procedure(s).

The computer system 150 preferably also includes an indicator mechanism 162 connected at least indirectly to the processor 156 and adapted to express the foregoing range(s) in a humanly perceivable manner. The indicator mechanism 162 may include a visual display device, such as a computer screen (e.g., a cathode ray tube or LCD display), an LED display, a printer, and/or the like, or it may include an audible device which audibly communicates such ranges.

The indicator mechanism 162 also can be used by the processor 156 to generate prompting messages which direct a user of the computer system 150 to enter desired values of product parameters (e.g., those specified by an end user of the product). A combination of audible prompting devices and visual display devices also can be used to generate such prompting messages.

The processor 156 preferably is adapted to generate the output signal 160 so that the output signal 160 also contains probability information indicative of how probable it is that products which are manufactured within the aforementioned range(s) and with the desired value of product parameter will respond favorably to the testing procedure(s). This probability information, examples of which are shown at the terminal branches of the binary decision trees in FIGS. 2A, 3–3A, 4A, 5A, 6A and 7A, can be presented to the user via the indicator mechanism 162.

Preferably, the product parameter selection program 158 is based on, not just one, but a plurality of binary decision trees derived from classification and regression tree analysis of product data on the previously manufactured products and test data on how such previously manufactured products respond to, not just one, but a plurality of testing procedures. Each of the binary decision trees corresponds to a respective one of the testing procedures. Examples of different binary decision trees which can be used include those which are illustrated in FIGS. 2A, 3–3A, 4A, 5A, 6A, and 7A. It is understood, however, that the invention is not limited to the exemplary binary decision trees.

The processor 156 is adapted, through suitable programming or otherwise, to perform the parameter selection program 158 by applying the information provided via the input device 154 to the binary decision trees. The processor 156 then generates the output signal 160 so that it indicates ranges of at least one other product parameter which, according to the binary decision trees, contain values of the other product parameter which enhance probabilities that a product with the desired value(s) will respond favorably to the testing procedures. The ranges then can be conveyed to the user via the indicator mechanism 162.

Preferably, the indicator mechanism 162 displays or otherwise conveys the ranges to the user in a format which makes apparent the correlation between each range and the testing procedure(s) which is favorably affected by that range.

The processor 156 preferably is further adapted to execute the classification and regression tree analysis and to generate, based on the classification and regression tree analysis, the binary decision tree(s) upon which the parameter selection program is based. In this regard, the storage device 152 can include a computer-readable database 164. The database 164 contains the sample data and test result data. Test data of preferably at least 500 tests is included in the database 164.

The storage device 152 also contains a classification and regression tree analysis program (CARTP) 166 in the form of hardware, software, and/or firmware, which is accessed by the processor 156 and which enables the processor 156 to perform classification and regression tree analysis on the product data and test result data. An example of software which can be used in this regard is the aforementioned CART™ program which is commercially available from Salford Systems of San Diego, Calif.

According to a preferred embodiment of the present invention, the computer system 150 is implemented using a conventional desk-top computer which is programmed to execute the computer-implemented methods described above. Such programming can be achieved using commercially available programming software, and is not limited to a particular computer operating system.

Alternatively, a specially designed version of the computer system 150 can be made using commercially available microprocessor technology, as well as commercially available input devices, storage devices, and indicator mechanisms.

Notably, the exemplary CART™ software is compatible with several commercially available computer operating systems, including Windows 3.X, Windows 95, Windows NT, Mac OS, UNIX, IBM MVS and CMS. The CART™ software also is supported by several commercially available hardware systems, including Intel PCS, Sun, SGI, HP, Digital Alpha, VAX, and IBM S6000 machines. The CART™ software also includes a data-translation engine capable of providing data conversion from more than seventy file formats, including conventional statistical-analysis packages, such as SASH and SPSS; conventional databases, such as Oracle and Informix; and conventional spreadsheets, such as Microsoft Excel and Lotus.

The computer-implemented classification and regression tree analysis therefore can be performed using the CART software and any one of several combinations of commercially available hardware, software, and/or firmware elements which can be configured to define the computer system 150 shown in FIG. 8.

The processor 156 preferably is further adapted, by suitable programming or otherwise, to classify the test result data into at least first, second, and third classes, as directed by the user. The determination of number of classes, and what qualities are used to define each class, can be made on a case-by-case basis, either automatically by the processor 156 or by the user with or without computer assistance.

According to an exemplary classification scheme, the first class contains test results indicative of favorable performance under the particular testing procedure. The second class contains test results indicative of marginal performance under the testing procedure, and the third class contains test results indicative of poor performance under the testing procedure.

The multiple decision result branches of each binary decision tree include terminal branches and intermediate branches. Each intermediate branch is logically defined between two binary decisions. Preferably, the processor 156 is adapted, through suitable programming or otherwise, to determine, for each of the terminal branches, a first probability of the sample being in the first class, a second probability of the sample being in the second class, and a third probability of the sample being in the third class. The processor 156 preferably is adapted to select the range for each binary decision, based on which product parameter causes the largest differences between the first and third probabilities. Alternatively, the range can be selected based on the largest differences between any other combination of the first, second, and/or third probabilities.

As demonstrated by the various examples of binary decision trees in FIGS. 2A, 3A, 4A, 5A, 6A and 7A, the present invention is particularly useful in the context of manufacturing coated steel products. In this regard, the binary decision tree(s) is (are) derived from a classification and regression tree analysis of a) sample data on previously manufactured coated steel products, and b) test result data on how such previously manufactured coated steel products respond to one or more testing procedures.

When the computer system 150 is adapted for use in connection with coated steel products, the ranges correspond to ranges of coating weight, iron content, gage, grade, and/or a coating phase composition. Preferably, the coated steel products and previously manufactured steel products are galvanneal-coated steel products.

The parameter selection program 158 preferably has portions based on each of the binary decision trees shown in FIGS. 2A, 3A, 4A, 5A, 6A and 7A. When a user of the computer system 150 is assigned a product development task, the user typically receives product specification information from the consumer requesting the product. This specification information (e.g., values of gage and the grade) constitutes the desired values described above. These desired values are provided to the processor 156 via the input device 154. The specification information also may include information indicative of a particular testing procedure or combination thereof which will be implemented by the consumer (e.g., V-Bend test with a visual rating scheme). Such testing procedures typically are invoked by consumers of semi-finished products to determine whether the products can withstand subsequent processing by the consumer.

The processor 156 then executes the portions of the parameter selection program 158 which are relevant to the specified testing procedure(s) (i.e., the portions associated with the relevant binary decision tree(s)), and in doing so, eliminates from consideration any paths through decision result branches which are inconsistent with the desired values. Of the remaining paths, the processor 156 selects one path in each binary decision tree which has the best probability of achieving a favorable test result. The ranges associated with each such path then are communicated to the user via the indicator mechanism, for use in his product development efforts.

Alternatively, the ranges corresponding to all of the binary decision trees (i.e, all of the testing procedures), not just those corresponding to the testing procedures selected by the consumer, can be determined by the processor 156 and communicated to the user. Each of the ranges is communicated with an indication of which testing procedure is associated with that range. The user of the computer system 150 then selects the range(s) pertaining to his consumer's particular testing procedure and uses those ranges in his product development efforts.

Method of Performing Process Control

Figure 9:
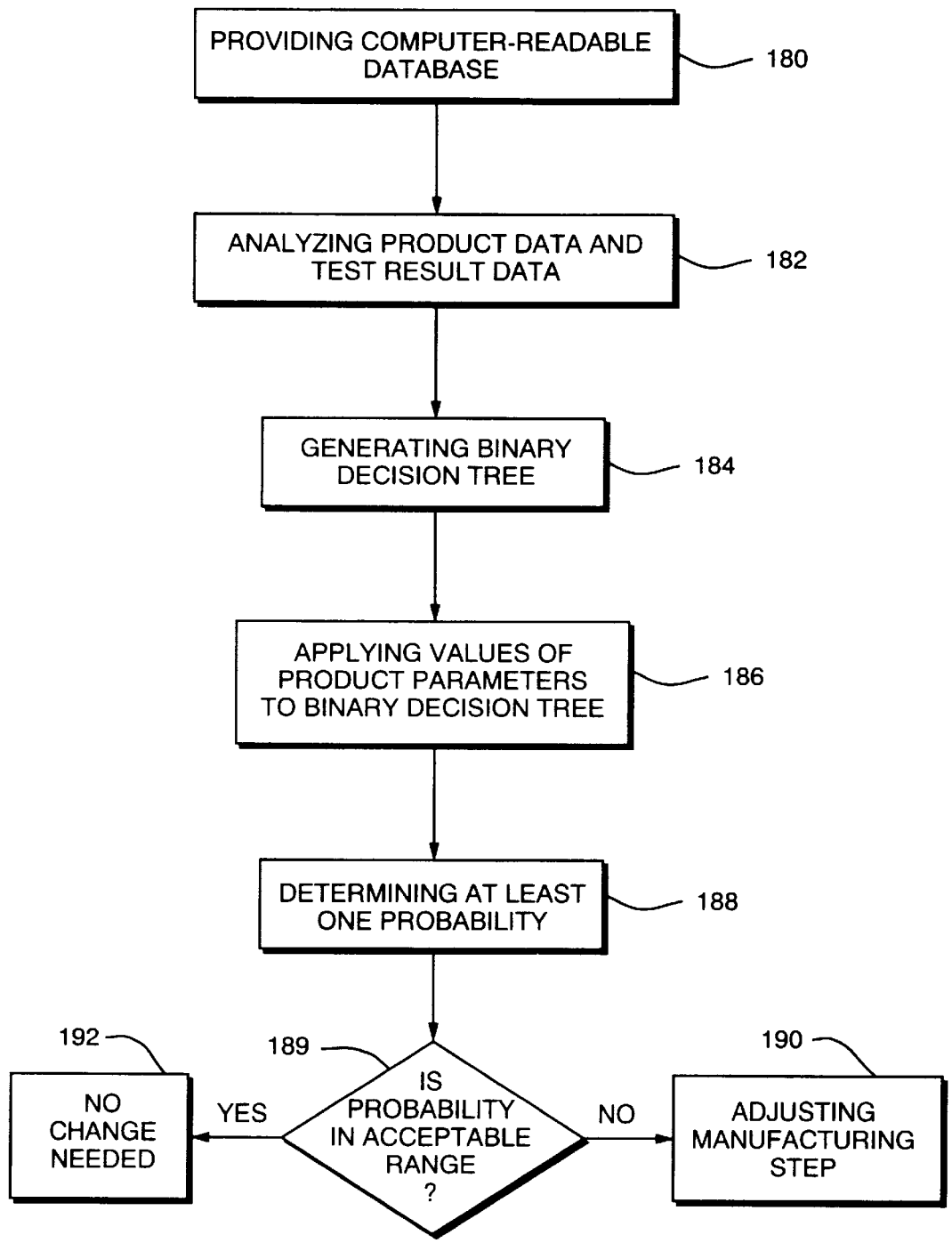
FIG. 9 is a flow chart of a preferred implementation of a method for performing process control.

The present invention also provides a method of performing process control in a manufacturing process. As shown in FIG. 9, a preferred implementation of the method includes the step (Step 180) of providing a computer-readable database. This database contains product data on several previously manufactured products, as well as test result data for each of the previously manufactured products. The test result data includes information on how the previously manufactured products performed when subjected to a first testing procedure.

The product data and the test result data are analyzed (Step 182) using a computer-implemented classification and regression tree analysis. Based on this computer-implemented analysis, a binary decision tree is generated (Step 184). The binary decision tree has multiple decision result branches. Each decision result branch is defined by a result of a binary decision on one of a plurality of parameters. Examples of the binary decision tree appear in FIGS. 2A, 3A, 4A, 5A, 6A, and 7A.

Values of sample parameters then are applied (Step 186) to the binary decision tree to eliminate from consideration any decision result branches which are inconsistent with such values. A determination then is made (Step 188) of at least one probability that a sample with those values of product parameters will respond favorably to the testing procedure.

If the probability(ies) is (are) outside of an acceptable range (Step 189), at least one step in the manufacturing process is adjusted (Step 190). Otherwise, it is determined than no change or adjustment is required in the manufacturing process (Step 192).

Preferably, the step (Step 182) of analyzing the sample data and the test result data includes the step of classifying the test result data into first, second, and third classes. The user either classifies the data, or provides parameters permitting computer classification. The first class contains test results indicative of favorable responses to the first testing procedure. The second class contains test results indicative of marginal responses to the first testing procedure. And, the third class contains test results indicative of poor responses to the first testing procedure.

As shown in FIGS. 2A, 3A, 4A, 5A, 6A, and 7A, the multiple decision result branches include terminal branches and intermediate branches. Each intermediate branch is logically defined between two of the binary decisions.

Preferably, the step (Step 184) of generating a binary decision tree includes the step of determining, for each of the terminal branches, a first probability of the sample being in the first class, a second probability of the sample being in the second class, and a third probability of the sample being in the third class.

The step (Step 190) of adjusting a step in the manufacturing process preferably includes the step of changing, based on the first, second, and third probabilities in an applicable one of the terminal branches, a rate at which the sample is tested for compliance with at least one manufacturing specification. The manufacturing specification might include, for example, the product's ability to respond favorably to the first testing procedure.

If there is a high probability of obtaining poor test results, the frequency of product testing can be increased. Likewise, the frequency of product testing can be decreased when there is a high probability of achieving favorable test results. Since testing in many manufacturing environments is expensive and time-consuming, the ability to intelligently adjust testing frequency using the method of the present invention provides a significant advantage over traditional trial-and-error techniques of determining testing frequency.

While the forgoing method is useful in other contexts, it is particularly useful in the context of manufacturing galvanneal-coated steel products. The plurality of parameters, in this regard, preferably include coating weight, iron content, gage, grade, and/or coating phase composition, and the test result data includes data derived from powdering tests on previously manufactured galvanneal-coated steel products.

The techniques, systems, and binary decision trees described in connection with the method of determining product parameters also can be applied to the method of conducting process control. The details of those techniques, systems, and binary decision trees therefore will not be repeated.

Computer System for Performing Process Control

Figure 10:
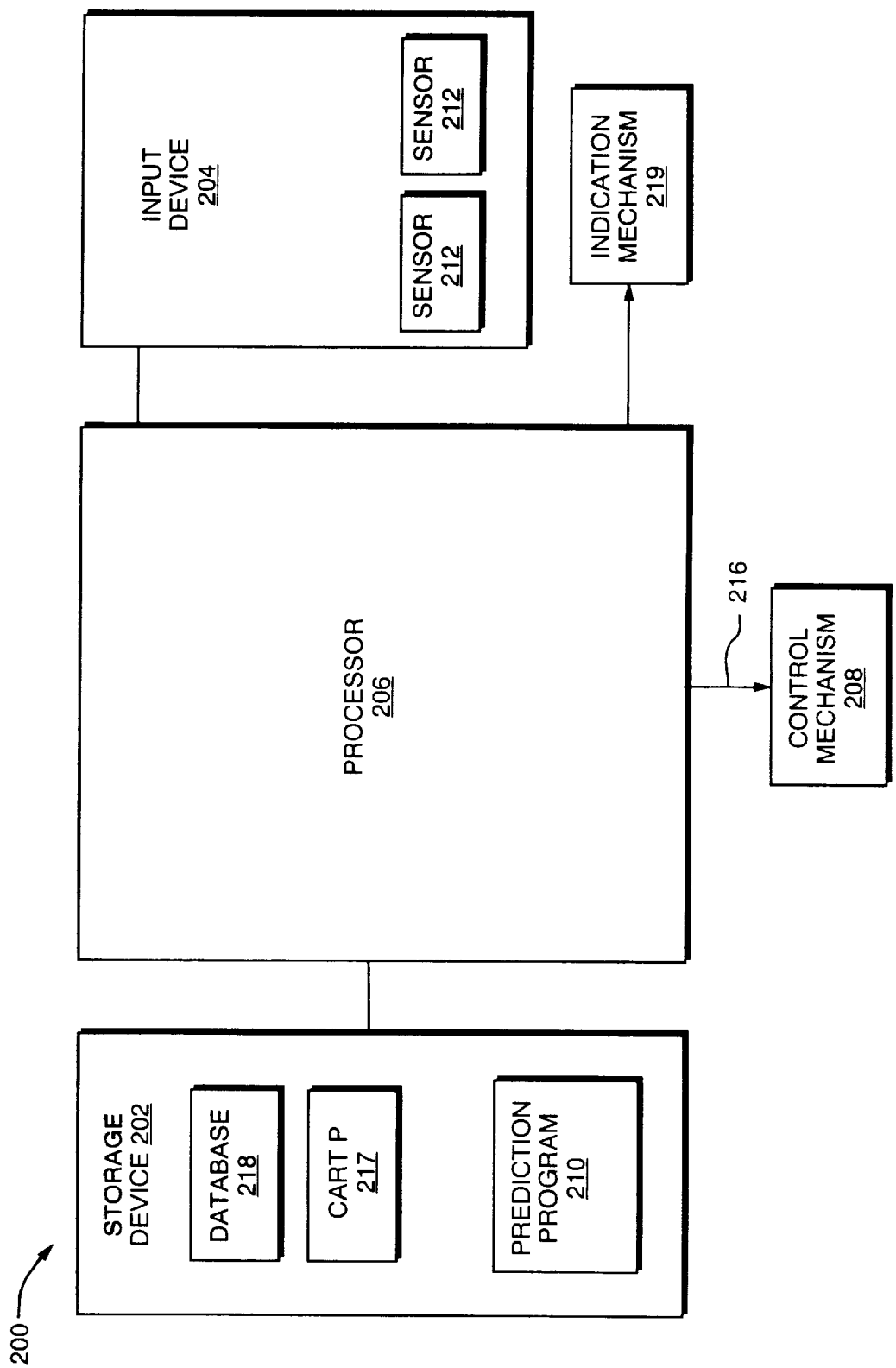
FIG. 10 is a block diagram of a computer system according to another preferred embodiment of the present invention.

FIG. 10 shows a preferred computer system 200 for use in performing process control, according to the present invention. The computer system 200 includes a storage device 202, an input device 204, a processor 206, and a control mechanism 208.

The storage device 202 contains a prediction program 210 based on at least one binary decision tree. The binary decision tree is derived from a classification and regression tree analysis of a) sample data on previously manufactured products, and b) test data on how such previously manufactured products respond to at least one testing procedure. Preferably, the classification and regression tree analysis is the same or similar to that which is used in the method of FIG. 1.

The input device 204 receives information indicative of at least one product parameter and converts this information to a format which is detectable by the processor 206. The input device 204 may be implemented using a keypad, a keyboard, a digitizer, a touch pad, a magnetic or optical medium reader, a proximity-sensitive surface, or any other known input device. The input device 204 may be manually actuated. Alternatively, it can be configured so as to automatically apply the requisite parameter values to the processor 206. The input device 204, in this regard, preferably includes one or more sensors 212 which are adapted to detect the product parameter(s) and to provide the aforementioned information indicative of the parameter(s) to the input device 204.

The processor 206 is connected at least indirectly to the storage device 202 and the input device 204. The processor 206 is adapted to perform the prediction program 210 by applying the information from the input device 204 to the binary decision tree(s). Based on this application of the information to the binary decision tree(s), the processor 206 generates an output signal 216. The output signal 216 is indicative of at least one probability that a favorable response to the testing procedure will be achieved by a sample with the product parameters indicated by the information from the input device 204.

In applying this information, the processor 206 preferably eliminates from consideration any decision result branches of binary decision tree(s) which are inconsistent with the product parameters contained in that information.

Preferably, the prediction program 210 is based, not on just one binary decision tree, but rather on a plurality of binary decision trees. Each binary decision tree corresponds to a respective one of several testing procedures. Each binary decision tree is derived from classification and regression tree analysis of sample data on the previously manufactured products and test data on how such previously manufactured products respond to the testing procedures. The processor 206 preferably is adapted to selectively apply the binary decision trees, as represented by respective portions of the prediction program 210, in a manner dependent upon which of the testing procedures is going to be applied to the product.

The prediction program 210 can be preloaded into the storage device 202, without having the processor 206 of each computer system 200 conduct the actual classification and regression tree analysis. Alternatively, the processor 206 may be adapted, through suitable programming or otherwise, to execute the classification and regression tree analysis and to generate, based on the classification and regression tree analysis, the binary decision tree(s) and/or aspects of the prediction program associated therewith. In this regard, the storage device 202 may also contain classification and regression tree analysis program (CARTP) 217 and a computer-readable database 218. The database 218 contains the product data and the test data which the processor 206 accesses during execution of the CARTP 217.

The processor 206 preferably is further adapted, by suitable programming or otherwise, to classify the test result data into first, second, and third classes. The first class contains test results indicative of favorable performance under the particular testing procedure. The second class contains test results indicative of marginal performance under the testing procedure, and the third class contains test results indicative of poor performance under the testing procedure.

The multiple decision result branches of each binary decision tree include terminal branches and intermediate branches. Each intermediate branch is logically defined between two binary decisions. Preferably, the processor 206 is adapted, through suitable programming or otherwise, to determine, for each of the terminal branches, a first probability of the sample being in the first class, a second probability of the sample being in the second class, and a third probability of the sample being in the third class.

If the processor 206 generates the binary decision tree or generates aspects of the prediction program based thereon, then it preferably is adapted to select the range for each binary decision in a manner dependent upon which product parameter causes the largest differences between the first and third probabilities. Alternatively, the range can be selected based on the largest differences between any other combination of the first, second, and/or third probabilities.

The control mechanism 208 is connected at least indirectly to the processor 206 and is responsive to the output signal 216. The control mechanism 208 is adapted to adjust at least one step in the manufacturing process. The control mechanism 208 performs this adjustment, however, only when the output signal 216 indicates that at least one of the probabilities is outside of an acceptable range.

The control mechanism 208 can be implemented using a plurality of different devices, including actuators, valves, electronic control devices, or the like. The operator may be able to adjust only certain parameters, such as coating weight. Other parameters, such as gage, are not operator adjustable, so the control mechanism adjusts only those parameters that the operator may adjust. The control mechanism 206 can be configured to change processing temperatures, times, pressures, compounds, and any other process variable which affects the relevant product parameter(s). In addition, it can be configured to adjust a frequency or rate at which the product is tested for compliance with a manufacturing specification (e.g., resistance to powdering). The adjustment(s) provided by the control mechanism 206 preferably is based on the aforementioned first, second, and third probabilities in an applicable one of the terminal branches. The "applicable one of the terminal branches" is understood to mean the particular terminal branch at the end of a path through the relevant binary decision tree, which path is dictated by the binary decisions on the product parameters.

As demonstrated by the various examples of binary decision trees in FIGS. 2A, 3A, 4A, 5A, 6A and 7A, the present invention is particularly useful in the context of manufacturing coated steel products. In this regard, the binary decision tree(s) used in connection with the computer system 200 can be derived from a classification and regression tree analysis of a) sample data on previously manufactured coated steel products, and b) test result data on how such previously manufactured coated steel products respond to one or more testing procedures. Exemplary testing procedures are those which are associated with each of the binary decision trees shown in FIGS. 2A, 3A, 4A, 5A, 6A and 7A.

When the computer system 200 is adapted for use in connection with coated steel products, the values of product parameters may include values of coating weight, iron content, gage, grade, and/or a coating phase composition. Preferably, the coated steel products and previously manufactured steel products are galvanneal-coated steel products.

The prediction program 210 preferably has portions based on each of the binary decision trees shown in FIGS. 2A, 3A, 4A, 5A, 6A and 7A. When product parameter values are applied, via the sensor(s) 212 and/or input device 204, to the processor 206 and the processor 206 is informed, via the input device 204 or otherwise, of which testing procedure(s) will be applied to the product, the processor 206 executes the portions of the prediction program 210 which are relevant to the specified testing procedure(s) (i.e., the portions associated with the relevant binary decision tree(s)). In doing so, the processor 206 eliminates from consideration any paths through decision result branches which are inconsistent with the product parameter values and testing procedures to be implemented.

Each remaining path will be associated with a probability of achieving a favorable test result in a corresponding one of the testing procedures. Preferably, the processor 206 is adapted, through suitable programming or otherwise, to compare this probability to one or more predetermined probability thresholds. Based upon the results of this comparison, the processor 206 supplies variations of the output signal 216. The variations may include command signals directing the control mechanism 208 to modify the manufacturing process. The control mechanism 208 responds to the output signal 216 and variations thereof by doing nothing, by changing a rate at which the product parameter is tested for compliance with one or more manufacturing specifications (e.g., resistance to powdering), or by modifying the manufacturing process so that, according to the binary decision tree(s), the probability of a favorable response to testing is enhanced.

In this regard, the control mechanism 206 can be adapted to change a rate at which the galvanneal-coated steel product is tested for compliance with powdering tests and/or for compliance with at least one manufacturing specification. The control mechanism 206 also can be adapted to modify the manufacturing process so that the probability of favorable test results is enhanced. In modifying the manufacturing process, the method and computer system for determining product parameters described above can be used in whole or in part.

The computer system 200 also may include an indication mechanism 219 similar or the same as the indication mechanism 162 shown in FIG. 8. The indication mechanism 219 can be driven by the processor 206 to convey information to the user on how the manufacturing process should be modified, how frequently testing should be conducted, and/or the like. This is especially desirable in situations where automatic modification of the manufacturing process and testing protocol is not possible or advisable.

The storage device 202, input device 204, and processor 206 can be implemented using some or all of the hardware, software, and/or firmware described above in connection with the computer system 150.

Method of Classifying a Product

Figure 11:
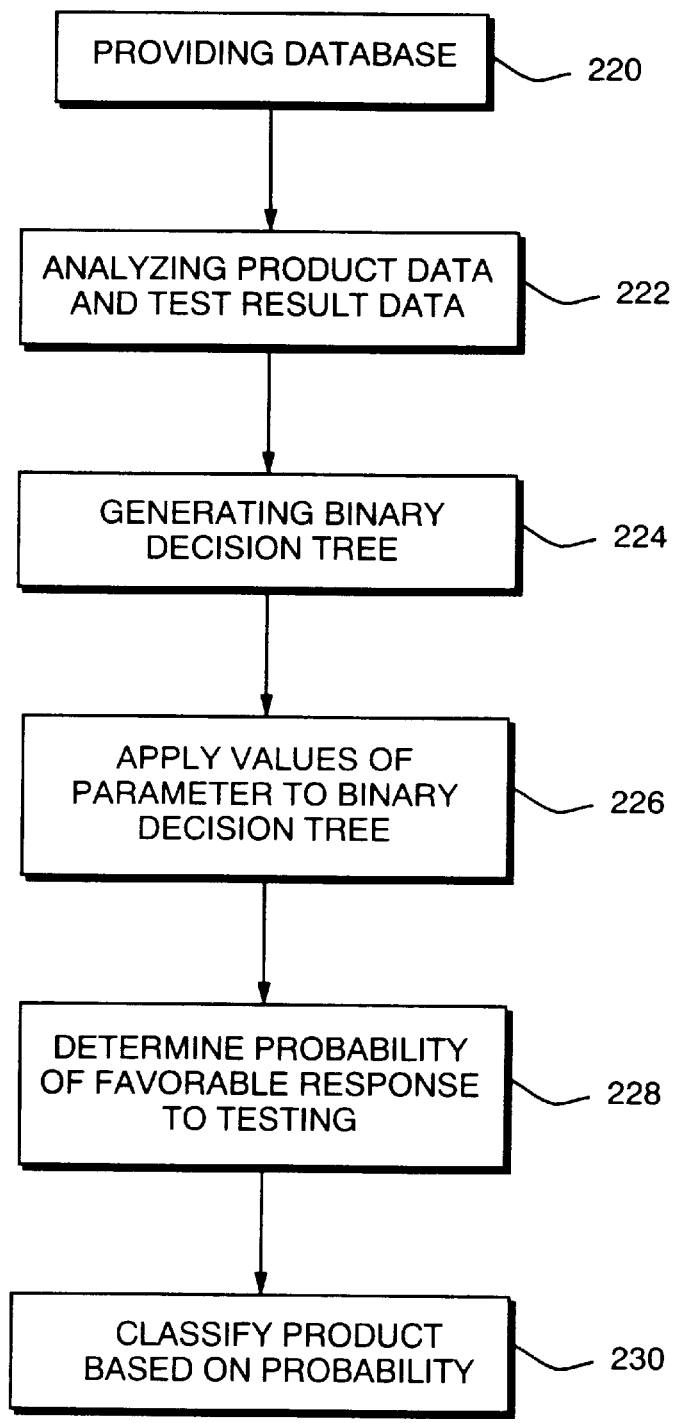
FIG. 11 is a flow chart of a preferred implementation of a method for use in classifying products.

The present invention also provides a method of classifying a product. FIG. 11 shows a preferred implementation of the method.

Initially, a computer readable database is provided (Step 220). The database contains sample data on several previously manufactured products, as well as test result data for each of the previously manufactured products. The test result data includes information on how the previously manufactured products performed when subjected to a first testing procedure;

The product data and test result data are analyzed (Step 222) using a computer-implemented classification and regression tree analysis. Preferably, this analysis is performed using the same or a similar classification and regression tree analysis to that which is described in connection with the process control and parameter determination aspects of the present invention.

A binary decision tree is generated (Step 224) based on the computer-implemented classification and regression tree analysis. The binary decision tree has multiple decision result branches, each of which is defined by a result of a binary decision on one of a plurality of parameters.

Values of parameters associated with the product (i.e., product parameters) then are applied (Step 226) to the binary decision tree. Based on these values of product parameters and the path they define through the binary decision tree, a determination is made (Step 228) of at least one probability that the sample will respond favorably to the first testing procedure. The sample then is classified (Step 230) as being good, marginal or poor, based on the resulting probability (ies).

Preferably, the step (222) of analyzing the product data and test result data includes the step of classifying the test result data into first, second, and third classes. The first class contains test results indicative of a good response to the first testing procedure. The second class contains test results indicative of marginal response to the first testing procedure. And, the third class contains test results indicative of poor response to the first testing procedure.

Preferably, the step (224) of generating a binary decision tree includes the step of determining, for each of the terminal branches in the tree, a first probability of the sample being in the first class, a second probability of the sample being in the second class, and a third probability of the sample being in the third class.

Based on these probabilities, the product can be scrapped, distributed to different end-users, stored in different locations, or subjected to different testing frequencies and/or testing procedures. Notably, the decision on which action to take is based, not upon trial-and-error, but rather upon an intelligently made and relatively accurate prediction.

The method shown in FIG. 11 preferably is implemented on coated steel and the manufacturing processes associated therewith. It is understood, however, that the invention is not limited to such use. The product and previously manufactured products preferably are coated steel, and most preferably, galvanneal-coated steel products. In this regard, the plurality of parameters can include coating weight, iron content, gage, grade, and/or coating phase composition, and the first testing procedure may comprise a test of resistance to powdering. Examples of such testing procedures and the binary trees associated therewith have already been described and need not be repeated.

Preferably, the test result data not only includes information on how the previously manufactured samples performed under the first testing procedure, but also information on how at least some of the previously manufactured products performed when subjected to at least a second testing procedure. A binary decision tree is generated for each of the different testing procedures, and values of product parameters are applied to each binary decision tree.

Based on the values of product parameters as applied to each binary decision tree, a determination is made of probabilities that the product will respond favorably when subjected to the first powdering test and the second powdering test(s). Preferably, the step of generating each binary decision tree includes the step of determining, for each of the terminal branches, a first probability of the product being in the first class, a second probability of the product being in the second class, and a third probability of the product being in the third class.

Each product then can be classified based on which of the first and at least a second testing procedures the product is most likely to satisfy as determined by the probabilities associated with each binary decision tree. This classification then can be used to determine, among other things, the distribution channels and/or the destination of the product.

Computer System for Use in Classifying Products

Figure 12:
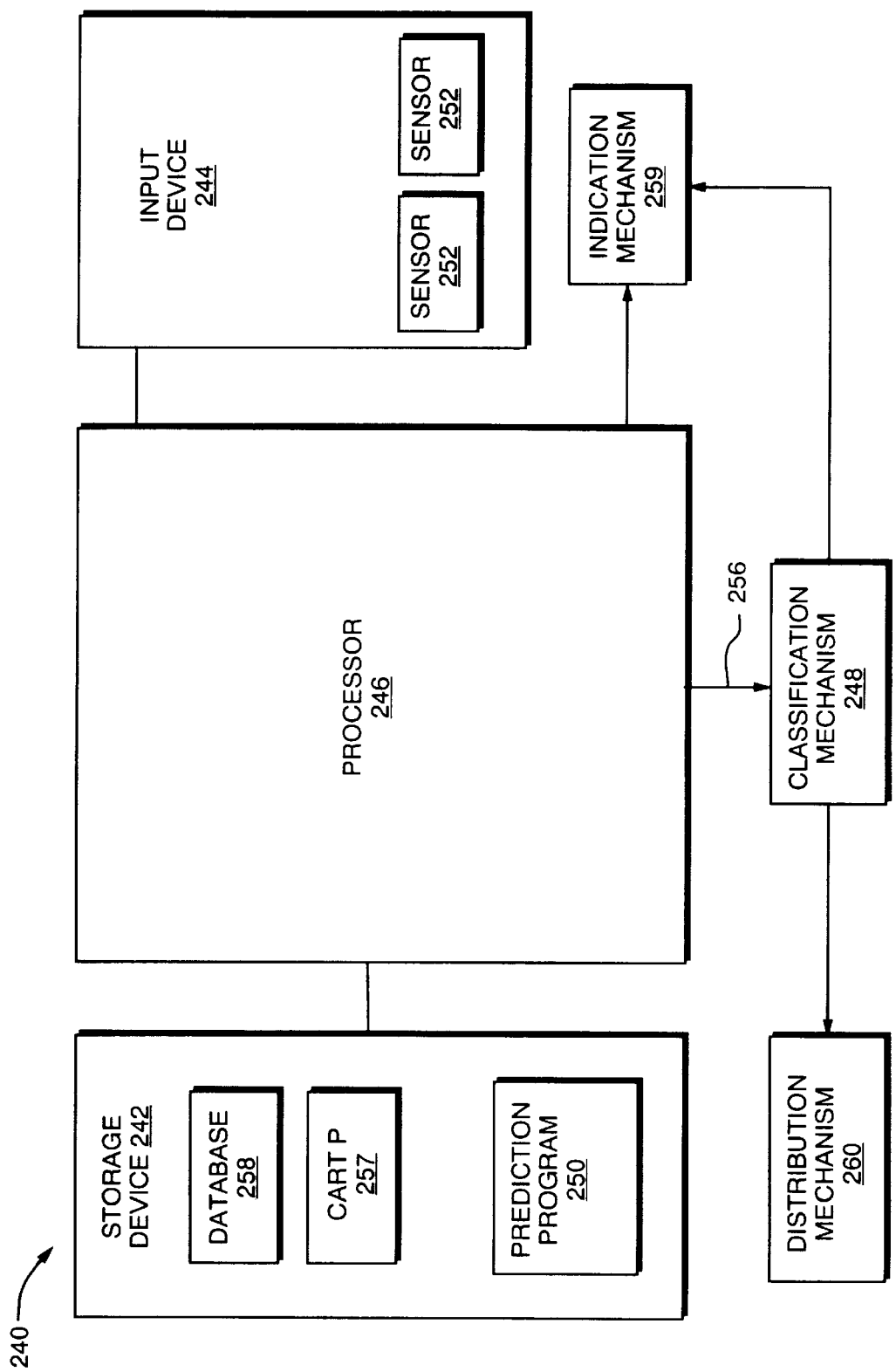
FIG. 12 is a block diagram of a computer system according to yet another preferred embodiment of the present invention.

FIG. 12 shows a preferred computer system 240 for use in classifying products, according to the present invention. The computer system 240 includes a storage device 242, an input device 244, a processor 246, and a classification mechanism 248.

The storage device 242 contains a prediction program 250 based on at least one binary decision tree. The storage device 242 and prediction program 250 may be implemented using elements similar or the same as those which are described in connection with the storage device 202 and prediction program 210.

The binary decision tree, in this regard, is derived from a classification and regression tree analysis of a) sample data on previously manufactured products, and b) test data on how such previously manufactured products respond to at least one testing procedure. The classification and regression tree analysis preferably is the same or similar to that which is used in the method of FIG. 1.

The input device 244 receives information indicative of at least one product parameter and converts this information to a format which is detectable by the processor 246. Much like the device 204 in FIG. 10, the input device 244 may be implemented using a keypad, a keyboard, a digitizer, a touch pad, a magnetic or optical medium reader, a proximity-sensitive surface, or any other known input device. The input device 244 may be manually actuated. Alternatively, it can be configured so as to automatically apply the requisite parameter values to the processor 246. The input device 244, in this regard, preferably includes one or more sensors 252 which are adapted to detect the product parameter(s) and to provide the aforementioned information indicative of the parameter(s) to the input device 244.

The processor 246 is connected at least indirectly to the storage device 242 and the input device 244. The processor 246 is adapted to perform the prediction program 250 by applying the information from the input device 244 to the binary decision tree(s). Based on this application of the information to the binary decision tree(s), the processor 246 generates an output signal 256. The output signal 256 is indicative of at least one probability that a favorable response to the testing procedure will be achieved by a product with the product parameters indicated by the information from the input device 244.

In applying this information to the binary decision tree(s), the processor 246 preferably eliminates from consideration any decision result branches which are inconsistent with the product parameters contained in that information.

Preferably, the prediction program 250 is based, not on just one binary decision tree, but rather on a plurality of binary decision trees. Each binary decision tree corresponds to a respective one of several testing procedures. Each binary decision tree is derived from classification and regression tree analysis of product data on the previously manufactured products and test data on how such previously manufactured products respond to the testing procedures. Preferably, the processor 246 can apply the parameter values to all of the binary decision trees. The processor 246 then determines which testing procedure has the highest probability of being satisfied by the product, and can classify the products according to this determination.

The prediction program 250 can be preloaded into the storage device 242, without having the processor 246 of each computer system 240 conduct the actual classification and regression tree analysis. Alternatively, the processor 246 may be adapted, through suitable programming or otherwise, to execute the classification and regression tree analysis and to generate, based on the classification and regression tree analysis, the binary decision tree(s) and/or aspects of the prediction program associated therewith. In this regard, the storage device 242 also may contain a classification and regression tree analysis program (CARTP) 257 and a computer-readable database 258. The database 258 contains the product data and the test data which the processor 246 accesses during execution of the CARTP 257.

The processor 246 preferably is further adapted, by suitable programming or otherwise, to classify the test result data into first, second, and third classes. The first class contains test results indicative of favorable performance under the particular testing procedure. The second class contains test results indicative of marginal performance under the testing procedure, and the third class contains test results indicative of poor performance under the testing procedure. Preferably, the processor 246 is adapted, through suitable programming or otherwise, to determine, for each of the terminal branches, a first probability of the sample being in the first class, a second probability of the sample being in the second class, and a third probability of the sample being in the third class.

If the processor 246 generates the binary decision tree or generates aspects of the prediction program 250 based thereon, then it preferably is adapted to select the ranges of product parameters for each binary decision in a manner dependent upon which product parameter causes the largest differences between the first and third probabilities. Alternatively, the ranges can be selected based on the largest differences between any other combination of the first, second, and/or third probabilities.

The classification mechanism 248 is connected at least indirectly to the processor 246 and is adapted to identify the product as good, marginal, or poor based on the probability (ies) indicated by the output signal 256. This identification can be applied to a distribution mechanism 260. The distribution mechanism 260 selectively distributes the product based on which of the testing procedures the product is most likely to satisfy. This facilitates the distribution of products to an end user or testing facility based on which tests such products are most likely to satisfy. This, in turn, advantageously minimizes test failures. It also conserves resources that otherwise might be spent on further testing and/or shipping of unacceptable products.

Alternatively, the classification of a product as good, marginal, or poor can be conveyed to the user of the system 240 via a suitable indication mechanism 259 similar or the same as the indication mechanisms 162 and 219 shown in FIGS. 8 and 10, respectively. In particular, the indication mechanism 259 is driven by the processor 246 and/or the classification mechanism 248 to convey information about the product's classification to the user, with or without information on the particular probabilities that led to the classification. This is especially desirable in situations where automatic distribution of the product is not possible or advisable.

As demonstrated by the various examples of binary decision trees in FIGS. 2A, 3A, 4A, 5A, 6A and 7A, the present invention is particularly useful in the context of manufacturing coated steel products. In this regard, the binary decision tree(s) used in connection with the computer system 240 can be derived from a classification and regression tree analysis of a) sample data on previously manufactured coated steel products, and b) test result data on how such previously manufactured coated steel products respond to one or more testing procedures. Exemplary testing procedures are those which are associated with each of the binary decision trees shown in FIGS. 2A, 3A, 4A, 5A, 6A and 7A.

When the computer system 240 is adapted for use in connection with coated steel products, the values of product parameters may include values of coating weight, iron content, gage, grade, and/or a coating phase composition. Preferably, the coated steel products and previously manufactured steel products are galvanneal-coated steel products.

The prediction program 250 preferably has portions based on each of the binary decision trees shown in FIGS. 2A, 3A, 4A, 5A, 6A and 7A. When product parameter values are applied, via the sensor(s) 252 and/or input device 244, to the processor 246, the processor 246 eliminates from consideration any paths through decision result branches which are inconsistent with the product parameter values.

Each remaining path will be associated with a probability of achieving a favorable test result in a corresponding one of the testing procedures. Preferably, the processor 246 is adapted, through suitable programming or otherwise, to compare this probability to one or more predetermined probability thresholds. Based upon the results of this comparison, the processor 246 supplies variations of the output signal 256. These variations may include command signals directing the classification mechanism 248 to adjust the product's classification. The control mechanism 248 responds to the output signal 256 and variations thereof by doing nothing, by changing a classification of the product, and/or by directing the distribution mechanism 260 to modify the distribution channels and/or destination of the product.

The sensors 212 and 252 can be implemented using several different sensor techniques, including but not limited to, optical detection techniques, ultrasonic techniques, radiation detection techniques, and any other technique capable of converting a phenomenon associated with one of the product parameters to an electrical signal indicative thereof. Sensors capable of detecting coating weight, iron content, gage, grade, and/or coating phase composition are examples of the type of sensors which can constitute sensors 212 and/or 252.

In the process and computer system for use in classifying products, the aforementioned methods and computer systems for determining product parameters and/or performing process control can be used in whole or in part. The storage device 242, input device 244, and processor 246, for example, can be implemented using some or all of the hardware, software, and/or firmware described above in connection with the computer systems 150 and 200.

The present invention also encompasses combinations of the various methods and computer systems described above. Taken to its logical conclusion, a single computer system can be provided using all or some of the illustrated components, which single computer system provides all three of the general aspects of the present invention, namely, product development, process control, and product classification, or provides a subcombination thereof.

While this invention has been described as having a preferred design, it is understood that the invention is not limited to the illustrated and described features. To the contrary, the invention is capable of further modifications, usages, and/or adaptations following the general principles of the invention and therefore includes such departures from the present disclosure as come within known or customary practice in the art to which the invention pertains, and as may be applied to the central features set forth above, and which fall within the scope of the appended claims.

What is claimed is:

1. A method of determining a range of values for at least one variable product parameter of a galvanneal-coated steel product to be manufactured, said method comprising the steps of:

providing a computer-readable database which contains product data on several previously manufactured galvanneal-coated steel products, as well as powdering test result data for each of said previously manufactured galvanneal-coated steel products, said powdering test result data including information on how the previously manufactured galvanneal-coated steel products performed when subjected to a powdering test procedure, said plurality of parameters including at least one parameter selected from the group of parameters consisting of a galvanneal coating weight, iron content, gage, grade, and coating phase composition;

analyzing said product data and said powdering test result data using a computer-implemented classification and regression tree analysis;

generating, based on said computer-implemented classification and regression tree analysis, a binary decision tree having multiple decision result branches, each decision result branch being defined by a result of a binary decision on one of a plurality of product parameters;

applying at least one desired value of a product parameter to said binary decision tree to eliminate from consideration any decision result branches which are inconsistent with said at least one desired value; and determining said range based upon which path through the decision result branches which were not eliminated from consideration, yields a best probability that a galvanneal-coated steel product with said at least one desired value will respond favorably to said powdering test procedure.

2. A method of determining a range of values for at least one variable product parameter of a product to be manufactured, said method comprising the steps of:

providing a computer-readable database which contains product data on several previously manufactured products, as well as test result data for each of said previously manufactured products, said test result data including information on how the previously manufactured products performed when subjected to a first testing procedure;

analyzing said product data and said test result data using a computer-implemented classification and regression tree analysis;

generating, based on said computer-implemented classification and regression tree analysis, a binary decision tree having multiple decision result branches, each decision result branch being defined by a result of a binary decision on one of a plurality of product parameters;

applying at least one desired value of a product parameter to said binary decision tree to eliminate from consideration any decision result branches which are inconsistent with said at least one desired value; and determining said range based upon which path through the decision result branches which were not eliminated from consideration, yields a best probability that a product with said at least one desired value will respond favorably to said first testing procedure.

3. The method of claim 2, wherein said step of analyzing said product data and said test result data includes the step of classifying said test result data into at least a first, second, and third classes, each class indicative of a performance characteristic;

wherein said multiple decision result branches include terminal branches and intermediate branches, each intermediate branch being logically defined between two of said binary decisions;

wherein said step of generating a binary decision tree includes the step of determining, for each of said terminal branches, probability of said product being in one of said classes.

4. The method of claim 2, wherein said product and said previously manufactured products are coated steel products, and wherein said plurality of parameters includes at least one parameter selected from the group of parameters consisting of a coating weight, iron content, gage, grade, iron weight percent, and coating phase composition.

5. A method of performing process control in a manufacturing process, comprising the steps of:

providing a computer-readable database which contains product data on several previously manufactured products, as well as test result data for each of said previously manufactured products, said test result data including information on how the previously manufactured products performed when subjected to a first testing procedure;

analyzing said product data and said test result data using a computer-implemented classification and regression tree analysis;

generating, based on said computer-implemented classification and regression tree analysis, a binary decision tree having multiple decision result branches, each decision result branch being defined by a result of a binary decision on one of a plurality of parameters;

applying values of product parameters to said binary decision tree to eliminate from consideration any decision result branches which are inconsistent with said values;

determining at least one probability, based on said values of product parameters, that a product with said values of product parameters will respond favorably to said first testing procedure; and adjusting at least one step in said manufacturing process if said at least one probability is outside of an acceptable range.

6. The method of claim 5, wherein said step of analyzing said product data and said test result data includes the step of classifying said test result data into at least first, second, and third classes, said first class containing test results indicative of favorable responses to said first testing procedure, said second class containing test results indicative of marginal responses to said first testing procedure, and said third class containing test results indicative of poor responses to said first testing procedure;

wherein said multiple decision result branches include terminal branches and intermediate branches, each intermediate branch being logically defined between two of said binary decisions; and wherein said step of generating a binary decision tree includes the step of determining, for each of said terminal branches, a first probability of said product being in said first class, a second probability of said product being in said second class, and a third probability of said product being in said third class.

7. The method of claim 6, wherein said step of adjusting a step in said manufacturing process includes the step of changing, based on said first, second, and third probabilities in an applicable one of said terminal branches, a rate at which the product is tested for compliance with at least one manufacturing specification.

8. The method of claim 5, wherein said plurality of parameters include at least one parameter selected from the group of parameters consisting of a coating weight, iron content, gage, grade, iron weight percent, and coating phase composition.

9. The method of claim 5, wherein said product is a galvanneal-coated steel product, and said first testing procedure is a test of powdering resistance.

10. The method of claim 5, wherein said step of adjusting a step in said manufacturing process includes the step of changing a rate at which the product is tested for compliance with at least one manufacturing specification.

11. A method of classifying a product, comprising the steps of:

providing a computer-readable database which contains product data on several previously manufactured products, as well as test result data for each of said previously manufactured products, said test result data including information on how the previously manufactured products performed when subjected to a first testing procedure;

analyzing said product data and said test result data using a computer-implemented classification and regression tree analysis;

generating, based on said computer-implemented classification and regression tree analysis, a binary decision tree having multiple decision result branches, each decision result branch being defined by a result of a binary decision on one of a plurality of parameters;

applying values of product parameters associated with said product to said binary decision tree;

determining at least one probability, based on said values of product parameters, that said product will respond favorably to said first testing procedure; and classifying said product as being good, marginal or poor, based on said at least one probability.

12. The method of claim 11, wherein said step of analyzing said product data and said test result data includes the step of classifying said test result data into at least first, second, and third classes, said first class containing test results indicative of a good response to said first testing procedure, said second class containing test results indicative of marginal response to said first testing procedure, and said third class containing test results indicative of poor response to said first testing procedure;

wherein said multiple decision result branches include terminal branches and intermediate branches, each intermediate branch being logically defined between two of said binary decisions; and wherein said step of generating a binary decision tree includes the step of determining, for each of said terminal branches, a first probability of said product being in said first class, a second probability of said product being in said second class, and a third probability of said product being in said third class.

13. The method of claim 11, wherein said product and said previously manufactured products are coated steel, and wherein said plurality of parameters includes at least one parameter selected from the group of parameters consisting of a coating weight, iron content, gage, grade, iron weight percent, and coating phase composition.

14. The method of claim 11, wherein said product and said previously manufactured product are galvanneal-coated steel products, and wherein said first testing procedure includes a test of resistance to powdering.

15. A method of classifying a product, comprising the steps of:

providing a computer-readable database which contains product data on several previously manufactured products, as well as test result data for each previously manufactured product, said test result data including information on how the previously manufactured products performed when subjected to a first testing procedure and information on how at least some of the previously manufactured products performed when subjected to at least a second testing procedure;

analyzing said product data and said test result data using a computer-implemented classification and regression tree analysis;

generating, for each of said first and at least a second testing procedures, a binary decision tree based on said computer-implemented classification and regression tree analysis, each binary decision tree having multiple decision result branches, each decision result branch being defined by a result of a binary decision on one of a plurality of parameters;

applying values of product parameters associated with said product to each binary decision tree;

determining, based on said values of product parameters as applied to each binary decision tree, probabilities of said product responding favorably when subjected to said first and at least a second powdering tests; and classifying said product based on which of said first and at least a second testing procedures said product is most likely to satisfy as determined by the probabilities associated with each binary decision tree.

16. The method of claim 15, wherein said step of analyzing said product data and said test result data includes the step of classifying said test result data into at least first, second, and third classes, said first class containing test results indicative of a good response to testing, said second class containing test results indicative of marginal response to testing, and said third class containing test results indicative of poor response to testing;

wherein said multiple decision result branches include terminal branches and intermediate branches, each intermediate branch being logically defined between two of said binary decisions; and wherein said step of generating each binary decision tree includes the step of determining, for each of said terminal branches, a first probability of said product being in said first class, a second probability of said product being in said second class, and a third probability of said product being in said third class.

17. The method of claim 15, wherein said product and said previously manufactured products are coated steel products, and wherein said plurality of parameters include at least one parameter selected from the group of parameters consisting of a coating weight, iron content, gage, grade, iron weight percent, and coating phase composition.

18. The method of claim 15, wherein said product and said previously manufactured products are galvanneal-coated steel products.

19. A computer system for use in determining product parameters, said computer system comprising:

a storage device containing a parameter selection program based on at least one binary decision tree derived from a classification and regression tree analysis of:

a) product data on previously manufactured products, and b) test data on how such previously manufactured products respond to at least one testing procedure;

an input device for receiving information indicative of at least one desired value of product parameter; and a processor connected at least indirectly to said storage device and said input device, said processor being adapted to perform said parameter selection program by applying said information to said at least one binary decision tree and generating an output signal indicative of at least one range of at least one other product parameter which, according to said at least one binary decision tree, contains values of said at least one other product parameter which enhance a probability that a product with said at least one desired value of product parameter will respond favorably to said at least one testing procedure.

20. The computer system of claim 19, further comprising an indicator mechanism connected at least indirectly to said processor and adapted to express said at least one range in a humanly perceivable manner.

21. The computer system of claim 19, wherein said processor further is adapted to generate said output signal so that said output signal also contains probability information indicative of how probable it is that products which are manufactured within said at least one range and with said at least one desired value of product parameter will respond favorably to said at least one testing procedure.

22. The computer system of claim 19, wherein said product parameter selection program is based on a plurality of binary decision trees derived from classification and regression tree analysis of product data on said previously manufactured products and test data on how such previously manufactured products respond to a plurality of testing procedures, each of said binary decision trees corresponding to a respective one of said testing procedures; and wherein said processor is adapted to perform said parameter selection program by applying said information to said binary decision trees and generating an output signal indicative of ranges of at least one other product parameter which, according to said binary decision trees, contain values of said other product parameter which enhance probabilities that a product with said at least one desired value of product parameter will respond favorably to said testing procedures.

23. The computer system of claim 19, wherein said processor is further adapted to execute said classification and regression tree analysis and to generate, based on said classification and regression tree analysis, said at least one binary decision tree; and wherein said storage device further contains a computer-readable database of said product data and said test data which said processor accesses during execution of said classification and regression tree analysis.

24. The computer system of claim 23, wherein said processor is connected at least indirectly to said storage device and said input device, said processor being adapted to perform said parameter selection program by applying said information to said at least one binary decision tree and generating an output signal indicative of at least one range of at least one other product parameter which, according to said at least one binary decision tree, contains values of said other product parameter which enhance a probability that a product with said at least one desired value of product parameter will respond favorably to said at least one testing procedure; and wherein said processor is programmed to eliminate from consideration any decision result branches of said at least one binary decision tree which are inconsistent with said information, said ranges being determined based on which path through the decision result branches which were not eliminated from consideration, terminates in the best probability that a product with said at least one desired value of product parameter will respond favorably to said at least one testing procedure.

25. The computer system of claim 23, wherein said processor is adapted to classify said test result data into at least first, second, and third classes, said first class containing test results indicative of favorable performance under said first testing procedure, said second class containing test results indicative of marginal performance under said first testing procedure, and said third class containing test results indicative of poor performance under said first testing procedure;

wherein multiple decision result branches of said at least one binary decision tree include terminal branches and intermediate branches, each intermediate branch being logically defined between two binary decisions;

wherein said processor is adapted to determine, for each of said terminal branches, a first probability of said product being in said first class, a second probability of said product being in said second class, and a third probability of said product being in said third class; and wherein said processor is adapted to select, for each binary decision, said at least one range based on which product parameter causes the largest differences between said first and third probabilities.

26. The computer system of claim 19, wherein said at least one binary decision tree is derived from a classification and regression tree analysis of:

a) product data on previously manufactured coated steel products, and b) test data on how such previously manufactured coated steel products respond to said at least one testing procedure; and wherein said at least one desired value of product parameter and said at least one other product parameter correspond to at least one product parameter selected from the group of product parameters consisting of a coating weight, iron content, gage, grade, iron weight percent, and coating phase composition.

27. The computer system of claim 19, wherein said previously manufactured products are galvanneal-coated steel products.

28. A computer system for use in performing process control, said computer system comprising:

a storage device containing a prediction program based on at least one binary decision tree derived from a classification and regression tree analysis of:

a) product data on previously manufactured products, and b) test data on how such previously manufactured products respond to at least one testing procedure;

an input device for receiving information indicative of at least one product parameter;

a processor connected at least indirectly to said storage device and said input device, said processor being adapted to perform said prediction program by applying said information to said at least one binary decision tree and generating an output signal indicative of at least one probability that a product with said at least one product parameter will respond favorably to said at least one testing procedure; and a control mechanism connected at least indirectly to said processor and responsive to said output signal, said control mechanism being adapted to adjust at least one step in a manufacturing process if said at least one probability is outside of an acceptable range.

29. The computer system of claim 28, further comprising at least one sensor adapted to detect said at least one product parameter, and to provide said information indicative of said at least one product parameter to said input device.

30. The computer system of claim 28, wherein said prediction program is based on a plurality of binary decision trees derived from classification and regression tree analysis of product data on said previously manufactured products and test data on how such previously manufactured products respond to a plurality of testing procedures, each of said binary decision trees corresponding to a respective one of said testing procedures; and wherein said processor is adapted to selectively apply the binary decision trees in a manner dependent upon which of said testing procedures is to be applied to said product.

31. The computer system of claim 28, wherein said processor is further adapted to execute said classification and regression tree analysis and to generate, based on said classification and regression tree analysis, said at least one binary decision tree; and wherein said storage device further contains a computer-readable database of said product data and said test data which said processor accesses during execution of said classification and regression tree analysis.

32. The computer system of claim 31, wherein said processor is adapted to classify said test result data into at least first, second, and third classes, said first class containing test results indicative of favorable performance under said first testing procedure, said second class containing test results indicative of marginal performance under said first testing procedure, and said third class containing test results indicative of poor performance under said first testing procedure;

wherein multiple decision result branches of said at least one binary decision tree include terminal branches and intermediate branches, each intermediate branch being logically defined between two binary decisions;

wherein said processor is adapted to determine, for each of said terminal branches, a first probability of said product being in said first class, a second probability of said product being in said second class, and a third probability of said product being in said third class; and wherein said processor is adapted to determine which product parameter causes the largest differences between said first and third probabilities and to establish said binary decisions based thereon.

33. The computer system of claim 32, wherein said control mechanism is adapted to adjust, based on said first, second, and third probabilities in an applicable one of said terminal branches, a rate at which said product is tested for compliance with at least one manufacturing specification.

34. The computer system of claim 28, wherein said at least one binary decision tree is derived from a classification and regression tree analysis of:

a) product data on previously manufactured coated steel products, and b) test data on how such previously manufactured coated steel products respond to said at least one testing procedure; and wherein said at least one product parameter includes at least one product parameter selected from the group of product parameters consisting of a coating weight, iron content, gage, grade, iron weight percent, and coating phase composition.

35. The computer system of claim 28, wherein said previously manufactured products are galvanneal-coated steel products.

36. The computer system of claim 35, wherein said at least one testing procedure includes testing of the product for resistance to powdering.

37. The computer system of claim 28, wherein said control mechanism is adapted to change a rate at which the product is tested for compliance with at least one manufacturing specification based on said at least one probability.

38. The computer system of claim 28, wherein said processor further is adapted to determine whether said probability is outside of said acceptable range, said processor also being adapted to transmit, when said probability is determined to be outside of said acceptable range, a command signal to said control mechanism which directs said control mechanism to modify said manufacturing process so that, according to said binary decision tree, said at least one probability is enhanced.

39. A computer system for use in classifying products, said computer system comprising:
- a storage device containing a prediction program based on at least one binary decision tree derived from a classification and regression tree analysis of:
  - a) a product data on previously manufactured products, and
  - b) test data on how such previously manufactured products respond to at least one testing procedure;
- an input device for receiving information indicative of at least one product parameter;
- a processor connected at least indirectly to said storage device and said input device, said processor being adapted to perform said prediction program by applying said information to said at least one binary decision tree and generating an output signal indicative of at least one probability that a product with said at least one product parameter will respond favorably to said at least one testing procedure; and
- a classification mechanism responsive to said processor, for identifying said product as good, marginal, or poor based on said at least one probability.

40. The computer system of claim 39, further comprising at least one sensor adapted to detect said at least one product parameter, and to provide said information indicative of said at least one product parameter to said input device.

41. The computer system of claim 39, wherein said prediction program is based on a plurality of binary decision trees derived from classification and regression tree analysis of product data on said previously manufactured products and test data on how such previously manufactured products respond to a plurality of testing procedures, each of said binary decision trees corresponding to a respective one of said testing procedures; and
- wherein said classification mechanism further classifies said product according to which of said testing procedures said product is most likely to satisfy, as determined by said at least one probability.

42. The computer system of claim 39, further comprising a distribution mechanism which distributes said product based on which of said testing procedures said product is most likely to satisfy.

43. The computer system of claim 39, wherein said processor is further adapted to execute said classification and regression tree analysis and to generate, based on said classification and regression tree analysis, said at least one binary decision tree; and
- wherein said storage device further contains a computer-readable database of said product data and said test data which said processor accesses during execution of said classification and regression tree analysis.

44. The computer system of claim 43, wherein said output signal from said processor is indicative of first, second, and third probabilities that a product with said at least one product parameter will respond favorably, marginally well, and poorly, respectively, to said at least one testing procedure;
- wherein said classification mechanism identifies said product as good, marginal, or poor depending upon which of said first, second, and third probabilities dominates;
- wherein said processor is adapted to determine which product parameter and which value thereof, when combined, provide the largest differences between said first and third probabilities; and
- wherein binary decisions of said at least one binary decision tree are defined at said value of product parameter.

45. The computer system of claim 39, wherein said at least one binary decision tree is derived from a classification and regression tree analysis of:
- a) product data on previously manufactured coated steel products, and
- b) test data on how such previously manufactured coated steel products respond to said at least one testing procedure; and
- wherein said at least one product parameter includes at least one product parameter selected from the group of product parameters consisting of a coating weight, iron content, gage, grade, iron weight percent, and coating phase composition.

46. The computer system of claim 39, wherein said previously manufactured products are galvanneal-coated steel products.

47. The computer system of claim 46, wherein said at least one testing procedure includes testing of the product for resistance to powdering.

* * * * *